US009822384B2

(12) United States Patent
Poulos et al.

(10) Patent No.: US 9,822,384 B2
(45) Date of Patent: Nov. 21, 2017

(54) PRODUCTION OF CANNABINOIDS IN YEAST

(71) Applicant: Librede Inc., Sherman Oaks, CA (US)

(72) Inventors: Jason L. Poulos, Los Angeles, CA (US); Anthony N. Farnia, Pasadena, CA (US)

(73) Assignee: Librede Inc., Sherman Oaks, CA (US)

( * ) Notice: Subject to any disclaimer, the term of this patent is extended or adjusted under 35 U.S.C. 154(b) by 43 days.

(21) Appl. No.: 14/795,816

(22) Filed: Jul. 9, 2015

(65) Prior Publication Data

US 2016/0010126 A1 Jan. 14, 2016

Related U.S. Application Data

(60) Provisional application No. 62/024,099, filed on Jul. 14, 2014.

(51) Int. Cl.

| | |
|---|---|
| ***C12P 7/42*** | (2006.01) |
| ***C12N 1/14*** | (2006.01) |
| ***C12N 15/00*** | (2006.01) |
| ***C12N 9/88*** | (2006.01) |
| ***C12N 9/10*** | (2006.01) |
| ***C12N 9/00*** | (2006.01) |
| ***C12N 15/81*** | (2006.01) |

(52) U.S. Cl.

CPC .............. *C12P 7/42* (2013.01); *C12N 9/1029* (2013.01); *C12N 9/1085* (2013.01); *C12N 9/88* (2013.01); *C12N 9/93* (2013.01); *C12N 15/81* (2013.01); *C12Y 203/01206* (2015.07); *C12Y 205/01* (2013.01); *C12Y 504/99* (2013.01); *C12Y 602/01* (2013.01)

(58) Field of Classification Search

CPC .......... C12N 9/93; C12N 9/88; C12N 9/1029; C12N 9/1085; C12N 15/81; C12P 7/42

See application file for complete search history.

(56) References Cited

U.S. PATENT DOCUMENTS

| | | | |
|---|---|---|---|
| 6,630,507 B1 | 10/2003 | Hampson et al. | |
| 7,186,850 B2 | 3/2007 | Silverberg | |
| 8,673,368 B2 | 3/2014 | Guy et al. | |
| 8,884,100 B2 | 11/2014 | Page et al. | |
| 2009/0226991 A1 | 9/2009 | Feldman et al. | |
| 2012/0144523 A1* | 6/2012 | Page .................... | C12N 9/1085 800/278 |
| 2013/0067619 A1* | 3/2013 | Page .................... | C12N 9/1025 800/278 |
| 2013/0210107 A1 | 8/2013 | Akada et al. | |
| 2014/0178954 A1 | 6/2014 | Hitz et al. | |

FOREIGN PATENT DOCUMENTS

| | | |
|---|---|---|
| WO | WO2013006953 | 1/2013 |
| WO | WO2014134281 | 9/2014 |
| WO | WO2016010827 | 1/2016 |

OTHER PUBLICATIONS

Fischer (Biotechnology and Bioengineering, vol. 108, No. 8, Aug. 2011.*

International Search Report and Written Opinion dated Dec. 28, 2015 in Patent Cooperation Treaty Application No. PCT/US2015/039812, filed Jul. 9, 2015.

GenBank entry HQ401270.1 "Recombinase expression vector pSH68, complete sequence" [retrieved on Nov. 18, 2015 from http://www.ncbi.nlm.nih.gov/nuccore/HW401270] Sep. 12, 2011 (Sep. 12, 2011).

Gagne, S.J. et al. Identification of olivetolic acid cyclase from Cannabis sativa reveals a unique catalytic route to plant polyketides. Proceedings of the National Academy of Sciences of the United States of America 109, 12811-12816 (2012).

Stout, J.M., Boubakir, Z., Ambrose, S.J., Purves, R.W. & Page, J.E. The hexanoyl-CoA precursor for cannabinoid biosynthesis is formed by an acyl-activating enzyme in Cannabis sativa trichomes. The Plant Journal 71, 353-365 (2012).

Shoyama, Y. et al. Structure and function of 1-Tetrahydrocannabinolic Acid (THCA) synthase, the enzyme controlling the psychoactivity of cannabis sativa. J. Mol. Biol., 423 (1), 96-105 (2012).

ElSohly et al. Chemical constituents of marijuana: The complex mixture of natural cannabinoids. National Center for Natural Products Research, School of Pharmacy, The University of Mississippi, University, MS 38677. Life Sciences (78), 539-548 (2005).

Ignea et al. Engineering monoterpene production in yeast using a synthetic dominant negative geranyl diphosphate synthase. ACS Synth Biol, May 16, 2014. vol. 3, No. 5. pp. 298-306.

Fonseca et al. The yeast *Kluyveromyces marxianus* and its biotechnological potential. Appl Microbiol Biotechnol, Jun. 2008, vol. 79, No. 3, pp. 339-354.

Written Opinion of the International Preliminary Examining Authority dated Jun. 24, 2016 in Patent Cooperation Treaty Application No. PCT/US2015/039812, filed Jul. 9, 2015, 5 pages.

* cited by examiner

*Primary Examiner* — Yong Pak

(74) *Attorney, Agent, or Firm* — Carr & Ferrell LLP

(57) ABSTRACT

Exemplary embodiments provided herein include genetically engineering microorganisms, such as yeast or bacteria, to produce cannabinoids by inserting genes that produce the appropriate enzymes for the metabolic production of a desired compound.

3 Claims, 8 Drawing Sheets

Librede's Pathway from Glucose to CBD

SEQUENCE LISTING

```
<160> NUMBER OF SEQ ID NOS: 53

<210> SEQ ID NO 1
<211> LENGTH: 7969
<212> TYPE: DNA
<213> ORGANISM: Artificial Sequence
<220> FEATURE:
<223> OTHER INFORMATION: Codon optimized

<400> SEQUENCE: 1

tcgcgcgttt cggtgatgac ggtgaaaacc tctgacacat gcagctcccg gagacggtca      60

cagcttgtct gtaagcggat gccgggagca gacaagcccg tcagggcgcg tcagcgcgtg     120

ttggcgggtg tcggggctgg cttaactatg cggcatcaga gcagattgta ctgagagtgc     180

accataaatt cccgttttaa gagcttggtg agcgctagga gtcactgcca ggtatcgttt     240

gaacacggca ttagtcaggg aagtcataac acagtccttt cccgcaattt tctttttcta     300

ttactcttgg cctcctctag tacactctat attttttat gcctcggtaa tgattttcat     360

ttttttttt cccctagcgg atgactcttt ttttttctta gcgattggca ttatcacata     420

atgaattata cattatataa agtaatgtga tttcttcgaa gaatatacta aaaaatgagc     480

aggcaagata aacgaaggca aagatgacag agcagaaagc cctagtaaag cgtattacaa     540

atgaaaccaa gattcagatt gcgatctctt taaagggtgg tcccctagcg atagagcact     600

cgatcttccc agaaaaagag gcagaagcag tagcagaaca ggccacacaa tcgcaagtga     660

ttaacgtcca cacaggtata gggtttctgg accatatgat acatgctctg gccaagcatt     720

ccggctggtc gctaatcgtt gagtgcattg gtgacttaca catagacgac catcacacca     780

ctgaagactg cgggattgct ctcggtcaag cttttaaaga ggccctactg gcgcgtggag     840

taaaaaggtt tggatcagga tttgcgcctt tggatgaggc actttccaga gcggtggtag     900

atctttcgaa caggccgtac gcagttgtcg aacttggttt gcaaagggag aaagtaggag     960

atctctcttg cgagatgatc ccgcattttc ttgaaagctt tgcagaggct agcagaatta    1020

ccctccacgt tgattgtctg cgaggcaaga atgatcatca ccgtagtgag agtgcgttca    1080

aggctcttgc ggttgccata agagaagcca cctcgcccaa tggtaccaac gatgttccct    1140

ccaccaaagg tgttcttatg tagtgacacc gattatttaa agctgcagca tacgatatat    1200

atacatgtgt atatatgtat acctatgaat gtcagtaagt atgtatacga acagtatgat    1260

actgaagatg acaaggtaat gcatcattct atacgtgtca ttctgaacga ggcgcgcttt    1320
```

-continued cctttttct ttttgctttt tcttttttt tctcttgaac tcgacggatc tatgcggtgt 1380
gaaataccgc acagatgcgt aaggagaaaa taccgcatca ggaaattgta aacgttaata 1440
ttttgttaaa attcgcgtta aatttttgtt aaatcagctc atttttaac caataggccg 1500 aaatcggcaa aatcccttat aaatcaaaag aatagaccga gatagggttg agtgttgttc 1560
cagtttggaa caagagtcca ctattaaaga acgtggactc caacgtcaaa gggcgaaaaa 1620
ccgtctatca gggcgatggc ccactacgtg aaccatcacc ctaatcaagt tttttggggt 1680
cgaggtgccg taaagcacta aatcggaacc ctaaagggag cccccgattt agagcttgac 1740
ggggaaagcc ggcgaacgtg gcgagaaagg aagggaagaa agcgaaagga gcgggcgcta 1800
gggcgctggc aagtgtagcg gtcacgctgc gcgtaaccac cacacccgcc gcgcttaatg 1860
cgccgctaca gggcgcgtcg cgccattcgc cattcaggct gcgcaactgt tgggaagggc 1920
gatcggtgcg ggcctcttcg ctattacgcc agctggcgaa agggggatgt gctgcaaggc 1980
gattaagttg ggtaacgcca gggttttccc agtcacgacg ttgtaaaacg acggccagtg 2040
agcgcgcgta atacgactca ctatagggcg aattgggtac cggccgcaaa ttaaagcctt 2100
cgagcgtccc aaaaccttct caagcaaggt tttcagtata atgttacatg cgtacacgcg 2160
tctgtacaga aaaaaaagaa aaatttgaaa tataaataac gttcttaata ctaacataac 2220
tataaaaaaa taaataggga cctagacttc aggttgtcta actccttcct tttcggttag 2280
agcggatgtg gggggagggc gtgaatgtaa gcgtgacata actaattaca tgactcgagg 2340
tcgactcatt cgaaatgact gaattgttgt ctcaaaactc ttctcatgat cttgtttgtt 2400
gcagttctag gtaaggatga caatgggaca actctagtaa ctttgaataa tgggttcaat 2460
ttcttttgca aacccaagtt aaaggataat ctcaattggt tcaaatcaat ggttgtgtcg 2520
tttgaatcct tcaatacgaa aaatatgacc aattgttctg gaccaccacc caaaggtgga 2580
acaccaatag cagtggtttc aaaaactctg tcatctactt cattacagac tctttcgatt 2640
tcgatagaac taattttgat accaccgatg ttcatagtgt catcggctct accgtgtgca 2700
tggtagtaac cgttagaggt caattcgaaa atgtcaccat gtcttctcaa tacttcacca 2760
ttcaaggttg gcataccctt gaaatagaca tcgtgatgat taccgtttaa caatgttttt 2820
gaggcaccaa acataacagg acctaatgcc aattcaccga tacctggctt atttttaggc 2880
attgggtaac cgttcttatc taatatgtac aaggtgcaac ccatacattg ggatgaaaaa 2940
gaacttaaag attgagcttg caaaaatgaa ccagcagaaa aagcaccacc gatttctgta 3000
ccaccacaca tttctataac tggcttgtag ttagctctac ccattaacca caaatattcg 3060
tctacattag aggcttcacc ggatgaagaa aagcatctta tggtggacca atcgtaacct 3120
gaaacacaat ttgtggattt ccatgatctt acaatagatg gtacgacacc caacattgtg 3180
acctttgcat cttgaacaaa tttagcgaaa ccagagacta aaggactacc gttgtacaag 3240
gcaatagatg caccatttaa caaactagca taaaccaacc aaggacccat catccaaccc 3300
aaattagttg gccatactat aacgtcacct tttctaatat ccaaatgaga ccaaccatca 3360
gcagcagcct tcaatggggt ggcttgtgtc caaggaattg cttttggttc acctgtagta 3420
ccactggaga ataagatgtt agtataagca tcaacaggtt gttctctggc agtaaactcg 3480
cagtttttaa actccttggc tctttctaaa aagtaatccc aagatatgtc accatctctc 3540
aattctgcac caatgttaga accactacaa gggataacta ttgccattgg ggatttagct 3600
tcaactactc ttgaatacaa tggtattctc tttttacctc tgatgatgtg atcttgtgtg 3660

-continued

```
aaaattgcct tagctttgga taatctcaat ctagttgaga tttcaggggc ggaaaatgaa   3720
tctgctatag agacaactac gtaaccagcc aatactatgg ccaaatatat aacaacagca   3780
tcaacatgca ttggcatatc gatggctatt gcacaacctt tttctaaacc catttcttcc   3840
aatgcataac caaccaacca aactctcttt ctcaattgat ctaatgtcaa cttattcaaa   3900
ggcaagtcat cgttaccctc gtctctccaa acgatcatag tatcgttcaa tttcttattg   3960
gagtttacgt tcaagcaatt tttagctgag ttcaagtaac caccaggtaa ccattcagaa   4020
ccacctgggt tgttgatgtc atctcttctc aagatacatt ctgggtcctt agagaaacta   4080
attttcattt catccatcaa tactgttctc caatagactt cagggtttct aacagaaaat   4140
tcttggaagt gagaaaaaga agaaattgga tctttgtact ttacacccaa aaattcttta   4200
cctctctttt ccaacaaagc acccaaatta gttgacttga ctttttcagg gtctggaatc   4260
caagcaggtg gggctggacc gaaatccttg tagcaaccat aaaacaacat ttggtgtaag   4320
gagaaaggca aatctggtga caagatatgg ttagcgatgt tgatccaagt ttgaggggtt   4380
gcagcaccat aattacaaac gatttctgcc aatctaccat gtaatgtttc tgctacttct   4440
gaggtgatac ccaatgcgat gaaatctgag gcaacgactg aatccaagga cttatagttt   4500
ttacccatac tagttctaga tccgtcgaaa ctaagttctt ggtgttttaa aactaaaaaa   4560
aagactaact ataaaagtag aatttaagaa gtttaagaaa tagatttaca gaattacaat   4620
caatacctac cgtctttata tacttattag tcaagtaggg gaataatttc agggaactgg   4680
tttaaacctt ttttttcagc tttttccaaa tcagagagag cagaaggtaa tagaaggtgt   4740
aagaaaatga gatagataca tgcgtgggtc aattgccttg tgtcatcatt tactccaggc   4800
aggttgcatc actccattga ggttgtgccc gtttttttgcc tgtttgtgcc ctgttctctg   4860
tagttgcgct aagagaatgg acctatgaac tgatggttgg tgaagaaaac aatattttgg   4920
tgctgggatt cttttttttt ctggatgcca gcttaaaaag cgggctccat tatatttagt   4980
ggatgccagg aataaacctg ttcacccaag caccatcagt gttatatatt ctgtgtaacc   5040
cgccccctat tttggcatgt acgggttaca gcagaattaa aaggctaatt ttttgactaa   5100
ataaagttag gaaaatcact actattaatt atttacgtat tctttgaaat ggcagtattg   5160
ataatgataa actcgagagc tccagctttt gttcccttta gtgagggtta attgcgcgct   5220
tggcgtaatc atggtcatag ctgtttcctg tgtgaaattg ttatccgctc acaattccac   5280
acaacatagg agccggaagc ataaagtgta aagcctgggg tgcctaatga gtgaggtaac   5340
tcacattaat tgcgttgcgc tcactgcccg ctttccagtc gggaaacctg tcgtgccagc   5400
tgcattaatg aatcggccaa cgcgcgggga gaggcggttt gcgtattggg cgctcttccg   5460
cttcctcgct cactgactcg ctgcgctcgg tcgttcggct gcggcgagcg gtatcagctc   5520
actcaaaggc ggtaatacgg ttatccacag aatcagggga taacgcagga aagaacatgt   5580
gagcaaaagg ccagcaaaag gccaggaacc gtaaaaaggc cgcgttgctg gcgtttttcc   5640
ataggctccg cccccctgac gagcatcaca aaaatcgacg ctcaagtcag aggtggcgaa   5700
acccgacagg actataaaga taccaggcgt ttccccctgg aagctccctc gtgcgctctc   5760
ctgttccgac cctgccgctt accggatacc tgtccgcctt tctcccttcg ggaagcgtgg   5820
cgctttctca tagctcacgc tgtaggtatc tcagttcggt gtaggtcgtt cgctccaagc   5880
tgggctgtgt gcacgaaccc cccgttcagc ccgaccgctg cgccttatcc ggtaactatc   5940
gtcttgagtc caacccggta agacacgact tatcgccact ggcagcagcc actggtaaca   6000
ggattagcag agcgaggtat gtaggcggtg ctacagagtt cttgaagtgg tggcctaact   6060
```

```
acggctacac tagaaggaca gtatttggta tctgcgctct gctgaagcca gttaccttcg   6120
gaaaaagagt tggtagctct tgatccggca aacaaaccac cgctggtagc ggtggttttt   6180
ttgtttgcaa gcagcagatt acgcgcagaa aaaaaggatc tcaagaagat cctttgatct   6240
tttctacggg gtctgacgct cagtggaacg aaaactcacg ttaagggatt ttggtcatga   6300
gattatcaaa aaggatcttc acctagatcc ttttaaatta aaaatgaagt tttaaatcaa   6360
tctaaagtat atatgagtaa acttggtctg acagttacca atgcttaatc agtgaggcac   6420
ctatctcagc gatctgtcta tttcgttcat ccatagttgc ctgactcccc gtcgtgtaga   6480
taactacgat acgggagggc ttaccatctg gccccagtgc tgcaatgata ccgcgagacc   6540
cacgctcacc ggctccagat ttatcagcaa taaaccagcc agccggaagg gccgagcgca   6600
gaagtggtcc tgcaacttta tccgcctcca tccagtctat taattgttgc cgggaagcta   6660
gagtaagtag ttcgccagtt aatagtttgc gcaacgttgt tgccattgct acaggcatcg   6720
tggtgtcacg ctcgtcgttt ggtatggctt cattcagctc cggttcccaa cgatcaaggc   6780
gagttacatg atcccccatg ttgtgcaaaa aagcggttag ctccttcggt cctccgatcg   6840
ttgtcagaag taagttggcc gcagtgttat cactcatggt tatggcagca ctgcataatt   6900
ctcttactgt catgccatcc gtaagatgct tttctgtgac tggtgagtac tcaaccaagt   6960
cattctgaga atagtgtatg cggcgaccga gttgctcttg cccggcgtca atacgggata   7020
ataccgcgcc acatagcaga actttaaaag tgctcatcat tggaaaacgt tcttcggggc   7080
gaaaactctc aaggatctta ccgctgttga gatccagttc gatgtaaccc actcgtgcac   7140
ccaactgatc ttcagcatct tttactttca ccagcgtttc tgggtgagca aaaacaggaa   7200
ggcaaaatgc cgcaaaaaag ggaataaggg cgacacggaa atgttgaata ctcatactct   7260
tcctttttca atattattga agcatttatc agggttattg tctcatgagc ggatacatat   7320
ttgaatgtat ttagaaaaat aaacaaatag gggttccgcg cacatttccc cgaaaagtgc   7380
cacctgggtc cttttcatca cgtgctataa aaataattat aatttaaatt ttttaatata   7440
aatatataaa ttaaaaatag aaagtaaaaa aagaaattaa agaaaaaata gtttttgttt   7500
tccgaagatg taaaagactc tagggggatc gccaacaaat actacctttt atcttgctct   7560
tcctgctctc aggtattaat gccgaattgt ttcatcttgt ctgtgtagaa gaccacacac   7620
gaaaatcctg tgattttaca ttttacttat cgttaatcga atgtatatct atttaatctg   7680
cttttcttgt ctaataaata tatatgtaaa gtacgctttt tgttgaaatt ttttaaacct   7740
ttgtttattt ttttttcttc attccgtaac tcttctacct tctttattta ctttctaaaa   7800
tccaaataca aaacataaaa ataaataaac acagagtaaa ttcccaaatt attccatcat   7860
taaaagatac gaggcgcgtg taagttacag gcaagcgatc cgtcctaaga aaccattatt   7920
atcatgacat taacctataa aaataggcgt atcacgaggc cctttcgtc              7969
```

<210> SEQ ID NO 2
<211> LENGTH: 10004
<212> TYPE: DNA
<213> ORGANISM: Artificial Sequence
<220> FEATURE:
<223> OTHER INFORMATION: Codon optimized

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
```

-continued

```
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctttca attcatcatt ttttttttat tctttttttt gatttcggtt    360
tctttgaaat ttttttgatt cggtaatctc cgaacagaag gaagaacgaa ggaaggagca    420
cagacttaga ttggtatata tacgcatatg tagtgttgaa gaaacatgaa attgcccagt    480
attcttaacc caactgcaca gaacaaaaac ctgcaggaaa cgaagataaa tcatgtcgaa    540
agctacatat aaggaacgtg ctgctactca tcctagtcct gttgctgcca agctatttaa    600
tatcatgcac gaaaagcaaa caaacttgtg tgcttcattg gatgttcgta ccaccaagga    660
attactggag ttagttgaag cattaggtcc caaaatttgt ttactaaaaa cacatgtgga    720
tatcttgact gatttttcca tggagggcac agttaagccg ctaaaggcat tatccgccaa    780
gtacaatttt ttactcttcg aagacagaaa atttgctgac attggtaata cagtcaaatt    840
gcagtactct gcgggtgtat acagaatagc agaatgggca gacattacga atgcacacgg    900
tgtggtgggc ccaggtattg ttagcggttt gaagcaggcg gcagaagaag taacaaagga    960
acctagaggc cttttgatgt tagcagaatt gtcatgcaag ggctccctat ctactggaga   1020
atatactaag ggtactgttg acattgcgaa gagcgacaaa gattttgtta tcggctttat   1080
tgctcaaaga gacatgggtg gaagagatga aggttacgat tggttgatta tgacacccgg   1140
tgtgggttta gatgacaagg gagacgcatt gggtcaacag tatagaaccg tggatgatgt   1200
ggtctctaca ggatctgaca ttattattgt tggaagagga ctatttgcaa agggaaggga   1260
tgctaaggta gagggtgaac gttacagaaa agcaggctgg gaagcatatt tgagaagatg   1320
cggccagcaa aactaatgac accgattatt taaagctgca gcatacgata tatatacatg   1380
tgtatatatg tatacctatg aatgtcagta agtatgtata cgaacagtat gatactgaag   1440
atgacaaggt aatgcatcat tctatacgtg tcattctgaa cgaggcgcgc tttccttttt   1500
tctttttgct ttttcttttt ttttctcttg aactcgacgg atctatgcgg tgtgaaatac   1560
cgcacagatg cgtaaggaga aaataccgca tcaggaaatt gtaaacgtta atattttgtt   1620
aaaattcgcg ttaaattttt gttaaatcag ctcatttttt aaccaatagg ccgaaatcgg   1680
caaaatccct tataaatcaa aagaatagac cgagataggg ttgagtgttg ttccagtttg   1740
gaacaagagt ccactattaa agaacgtgga ctccaacgtc aaagggcgaa aaaccgtcta   1800
tcagggcgat ggcccactac gtgaaccatc accctaatca agttttttgg ggtcgaggtg   1860
ccgtaaagca ctaaatcgga accctaaagg gagcccccga tttagagctt gacggggaaa   1920
gccggcgaac gtggcgagaa aggaagggaa gaaagcgaaa ggagcgggcg ctagggcgct   1980
ggcaagtgta gcggtcacgc tgcgcgtaac caccacaccc gccgcgctta atgcgccgct   2040
acagggcgcg tcgcgccatt cgccattcag gctgcgcaac tgttgggaag ggcgatcggt   2100
gcgggcctct tcgctattac gccagctggc gaaaggggga tgtgctgcaa ggcgattaag   2160
ttgggtaacg ccagggtttt cccagtcacg acgttgtaaa acgacggcca gtgagcgcgc   2220
gtaatacgac tcactatagg gcgaattggg taccggccgc aaattaaagc cttcgagcgt   2280
cccaaaacct tctcaagcaa ggttttcagt ataatgttac atgcgtacac gcgtctgtac   2340
agaaaaaaaa gaaaaatttg aaatataaat aacgttctta atactaacat aactataaaa   2400
aaataaatag ggacctagac ttcaggttgt ctaactcctt ccttttcggt tagagcggat   2460
gtgggggggag ggcgtgaatg taagcgtgac ataactaatt acatgactcg aggtcgactt   2520
```

```
acttgtcatc gtcatctttg tagtcaatat cgtggtcttt atagtcaccg tcatgatcct   2580
tgtaatcctt tgatctcttg tagaccttat tcaagaaagc tgtcaaaacg tcggctttaa   2640
aacctcttga ttcatcaact tgactaatct ttgcctttaa gtctttagcg atggattctt   2700
cgtattcatg gtacaattgt tcaatcttca aatcattaaa aattttctta cactttgctt   2760
cagcaactga gtccttttta ccgtagtttt catccaaagt ctttctttgt tcggcagatg   2820
ctaattccaa agccttgtta ataacccaac tgcacttatt gtcttgaata tctgtaccga   2880
ttttacctat ttgttctgga gtaccgaaac agtctaagta gtcatcttgg atttggaagt   2940
attcacccaa aggtatcaaa acatctcttg cttgcttcaa gtctttttca tcagtaatac   3000
cagctacgta catagccaag gcgactggca aatagaagga gtaataagca gtttcaaagg   3060
tgacgatgaa tgaatgtttc ttcaaggaaa actttgacaa gtcaacttta tcttcaggtg   3120
cagttatcaa atccatcaat tgacccaatt ctgtttggaa agtaacttcg tggaataatt   3180
cggtaatatc gatgtagtac ttttcgtttc tgaaatgtga cttcaacaat ttatagatag   3240
cggcttccaa cataaaagca tcatttatgg ctatttcacc aacttctgga actttgtacc   3300
agcatggttg acctcttctt gttatagact tatccatcat gtcatcggca accaaaaagt   3360
atgcttgcaa caattcaata caccaaccca agatagcgac cttttcgtat tcttcttgac   3420
ctaattgttc aacggttttg ttagacaaga tagcataagt atcaactaca ctcaaacctc   3480
tattcaattt accacctgga gtattgtagt ttaaagagtg agcataccaa tcgcaggctt   3540
ctttaggcat accataagct aacaaactag cgttcaattc ttcaactaac tttgggaata   3600
cgttcaagaa tctttctctt cttatttcct tttctgaagc cataggacct ggattttctt   3660
caacgtcacc acatgttaac aaagaacctc taccttcttc gaaatgactg aattgttgtc   3720
tcaaaactct tctcatgatc ttgtttgttg cagttctagg taaggatgac aatgggacaa   3780
ctctagtaac tttgaataat gggttcaatt tcttttgcaa acccaagtta aaggataatc   3840
tcaattggtt caaatcaatg gttgtgtcgt ttgaatcctt caatacgaaa aatatgacca   3900
attgttctgg accaccaccc aaaggtggaa caccaatagc agtggtttca aaaactctgt   3960
catctacttc attacagact ctttcgattt cgatagaact aattttgata ccaccgatgt   4020
tcatagtgtc atcggctcta ccgtgtgcat ggtagtaacc gttagaggtc aattcgaaaa   4080
tgtcaccatg tcttctcaat acttcaccat tcaaggttgg catacccttg aaatagacat   4140
cgtgatgatt accgtttaac aatgttttg  aggcaccaaa cataacagga cctaatgcca   4200
attcaccgat acctggctta tttttaggca ttgggtaacc gttcttatct aatatgtaca   4260
aggtgcaacc catacattgg gatgaaaaag aacttaaaga ttgagcttgc aaaaatgaac   4320
cagcagaaaa agcaccaccg atttctgtac caccacacat ttctataact ggcttgtagt   4380
tagctctacc cattaaccac aaatattcgt ctacattaga ggcttcaccg gatgaagaaa   4440
agcatcttat ggtggaccaa tcgtaacctg aaacacaatt tgtggatttc catgatctta   4500
caatagatgg tacgacaccc aacattgtga cctttgcatc ttgaacaaat ttagcgaaac   4560
cagagactaa aggactaccg ttgtacaagg caatagatgc accatttaac aaactagcat   4620
aaaccaacca aggacccatc atccaaccca aattagttgg ccatactata acgtcacctt   4680
ttctaatatc caaatgagac caaccatcag cagcagcctt caatggggtg gcttgtgtcc   4740
aaggaattgc ttttggttca cctgtagtac cactggagaa taagatgtta gtataagcat   4800
caacaggttg ttctctggca gtaaactcgc agtttttaaa ctccttggct ctttctaaaa   4860
```

```
agtaatccca agatatgtca ccatctctca attctgcacc aatgttagaa ccactacaag   4920
ggataactat tgccattggg gatttagctt caactactct tgaatacaat ggtattctct   4980
ttttacctct gatgatgtga tcttgtgtga aaattgcctt agctttggat aatctcaatc   5040
tagttgagat ttcaggggcg gaaaatgaat ctgctataga gacaactacg taaccagcca   5100
atactatggc caaatatata acaacagcat caacatgcat tggcatatcg atggctattg   5160
cacaaccttt ttctaaaccc atttcttcca atgcataacc aaccaaccaa actctctttc   5220
tcaattgatc taatgtcaac ttattcaaag gcaagtcatc gttaccctcg tctctccaaa   5280
cgatcatagt atcgttcaat ttcttattgg agtttacgtt caagcaattt ttagctgagt   5340
tcaagtaacc accaggtaac cattcagaac cacctgggtt gttgatgtca tctcttctca   5400
agatacattc tgggtcctta gagaaactaa ttttcatttc atccatcaat actgttctcc   5460
aatagacttc agggtttcta acagaaaatt cttggaagtg agaaaaagaa gaaattggat   5520
ctttgtactt tacacccaaa aattctttac ctctcttttc caacaaagca cccaaattag   5580
ttgacttgac tttttcaggg tctggaatcc aagcaggtgg ggctggaccg aaatccttgt   5640
agcaaccata aaacaacatt tggtgtaagg agaaaggcaa atctggtgac aagatatggt   5700
tagcgatgtt gatccaagtt tgaggggttg cagcaccata attacaaacg atttctgcca   5760
atctaccatg taatgtttct gctacttctg aggtgatacc caatgcgatg aaatctgagg   5820
caacgactga atccaaggac ttatagtttt tacccatact agttctagat ccgtcgaaac   5880
taagttcttg gtgttttaaa actaaaaaaa agactaacta taaaagtaga atttaagaag   5940
tttaagaaat agatttacag aattacaatc aatacctacc gtctttatat acttattagt   6000
caagtagggg aataatttca gggaactggt ttaaaccttt tttttcagct ttttccaaat   6060
cagagagagc agaaggtaat agaaggtgta agaaaatgag atagatacat gcgtgggtca   6120
attgccttgt gtcatcattt actccaggca ggttgcatca ctccattgag gttgtgcccg   6180
ttttttgcct gtttgtgccc tgttctctgt agttgcgcta agagaatgga cctatgaact   6240
gatggttggt gaagaaaaca atattttggt gctgggattc tttttttttc tggatgccag   6300
cttaaaaagc gggctccatt atatttagtg gatgccagga ataaacctgt tcacccaagc   6360
accatcagtg ttatatattc tgtgtaaccc gccccctatt ttggcatgta cgggttacag   6420
cagaattaaa aggctaattt tttgactaaa taaagttagg aaaatcacta ctattaatta   6480
tttacgtatt ctttgaaatg gcagtattga taatgataaa ctcgagagct ccagcttttg   6540
ttcagttgat tgtatgcttg gtatagcttg aaatattgtg cagaaaaaga aacaaggaag   6600
aaagggaacg agaacaatga cgaggaaaca aaagattaat aattgcaggt ctatttatac   6660
ttgatagcaa gacagcaaac ttttttttat ttcaaattca agtaactgga aggaaggccg   6720
tataccgttg ctcattagag agtagtgtgc gtgaatgaag gaaggaaaaa gtttcgtgtg   6780
cttcgagata cccctcatca gctctggaac aacgacatct gttggtgctg tctttgtcgt   6840
taattttttc ctttagtgtc ttccatcatt tttttgtcat tgcggatatg gtgagacaac   6900
aacgggggag agagaaaaga aaaaaaaaga aaagaagttg catgcgccta ttattacttc   6960
aatagatggc aaatggaaaa agggtagtga aacttcgata tgatgatggc tatcaagtct   7020
agggctacag tattagttcg ttatgtacca ccatcaatga ggcagtgtaa ttggtgtagt   7080
cttgtttagc ccattatgtc ttgtctggta tctgttctat tgtatatctc ccctccgcca   7140
cctacatgtt agggagacca acgaaggtat tataggaatc ccgatgtatg ggtttggttg   7200
ccagaaaaga ggaagtccat attgtacacc cggaaacaac aaaaggatgc gcgcttggcg   7260
```

```
taatcatggt catagctgtt tcctgtgtga aattgttatc cgctcacaat tccacacaac   7320
ataggagccg gaagcataaa gtgtaaagcc tggggtgcct aatgagtgag gtaactcaca   7380
ttaattgcgt tgcgctcact gcccgctttc cagtcgggaa acctgtcgtg ccagctgcat   7440
taatgaatcg gccaacgcgc ggggagaggc ggtttgcgta ttgggcgctc ttccgcttcc   7500
tcgctcactg actcgctgcg ctcggtcgtt cggctgcggc gagcggtatc agctcactca   7560
aaggcggtaa tacggttatc cacagaatca ggggataacg caggaaagaa catgtgagca   7620
aaaggccagc aaaaggccag gaaccgtaaa aaggccgcgt tgctggcgtt tttccatagg   7680
ctccgccccc ctgacgagca tcacaaaaat cgacgctcaa gtcagaggtg gcgaaacccg   7740
acaggactat aaagatacca ggcgtttccc cctggaagct ccctcgtgcg ctctcctgtt   7800
ccgaccctgc cgcttaccgg atacctgtcc gcctttctcc cttcgggaag cgtggcgctt   7860
tctcatagct cacgctgtag gtatctcagt tcggtgtagg tcgttcgctc caagctgggc   7920
tgtgtgcacg aaccccccgt tcagcccgac cgctgcgcct tatccggtaa ctatcgtctt   7980
gagtccaacc cggtaagaca cgacttatcg ccactggcag cagccactgg taacaggatt   8040
agcagagcga ggtatgtagg cggtgctaca gagttcttga agtggtggcc taactacggc   8100
tacactagaa ggacagtatt tggtatctgc gctctgctga agccagttac cttcggaaaa   8160
agagttggta gctcttgatc cggcaaacaa accaccgctg gtagcggtgg tttttttgtt   8220
tgcaagcagc agattacgcg cagaaaaaaa ggatctcaag aagatccttt gatcttttct   8280
acggggtctg acgctcagtg gaacgaaaac tcacgttaag ggattttggt catgagatta   8340
tcaaaaagga tcttcaccta gatcctttta aattaaaaat gaagttttaa atcaatctaa   8400
agtatatatg agtaaacttg gtctgacagt taccaatgct taatcagtga ggcacctatc   8460
tcagcgatct gtctatttcg ttcatccata gttgcctgac tccccgtcgt gtagataact   8520
acgatacggg agggcttacc atctggcccc agtgctgcaa tgataccgcg agacccacgc   8580
tcaccggctc cagatttatc agcaataaac cagccagccg gaagggccga gcgcagaagt   8640
ggtcctgcaa ctttatccgc ctccatccag tctattaatt gttgccggga agctagagta   8700
agtagttcgc cagttaatag tttgcgcaac gttgttgcca ttgctacagg catcgtggtg   8760
tcacgctcgt cgtttggtat ggcttcattc agctccggtt cccaacgatc aaggcgagtt   8820
acatgatccc ccatgttgtg caaaaaagcg gttagctcct tcggtcctcc gatcgttgtc   8880
agaagtaagt tggccgcagt gttatcactc atggttatgg cagcactgca taattctctt   8940
actgtcatgc catccgtaag atgcttttct gtgactggtg agtactcaac caagtcattc   9000
tgagaatagt gtatgcggcg accgagttgc tcttgcccgg cgtcaatacg ggataatacc   9060
gcgccacata gcagaacttt aaaagtgctc atcattggaa aacgttcttc ggggcgaaaa   9120
ctctcaagga tcttaccgct gttgagatcc agttcgatgt aacccactcg tgcacccaac   9180
tgatcttcag catcttttac tttcaccagc gtttctgggt gagcaaaaac aggaaggcaa   9240
aatgccgcaa aaaagggaat aagggcgaca cggaaatgtt gaatactcat actcttcctt   9300
tttcaatatt attgaagcat ttatcagggt tattgtctca tgagcggata catatttgaa   9360
tgtatttaga aaaataaaca aataggggtt ccgcgcacat ttccccgaaa agtgccacct   9420
gggtcctttt catcacgtgc tataaaaata attataattt aaatttttta atataaatat   9480
ataaattaaa aatagaaagt aaaaaaagaa attaaagaaa aaatagtttt tgttttccga   9540
agatgtaaaa gactctaggg ggatcgccaa caaatactac cttttatctt gctcttcctg   9600
```

```
ctctcaggta ttaatgccga attgtttcat cttgtctgtg tagaagacca cacacgaaaa   9660

tcctgtgatt ttacatttta cttatcgtta atcgaatgta tatctattta atctgctttt   9720

cttgtctaat aaatatatat gtaaagtacg ctttttgttg aaatttttta aacctttgtt   9780

tattttttt tcttcattcc gtaactcttc taccttcttt atttactttc taaaatccaa   9840

atacaaaaca taaaaataaa taaacacaga gtaaattccc aaattattcc atcattaaaa   9900

gatacgaggc gcgtgtaagt tacaggcaag cgatccgtcc taagaaacca ttattatcat   9960

gacattaacc tataaaaata ggcgtatcac gaggcccttt cgtc                  10004
```

```
<210> SEQ ID NO 3
<211> LENGTH: 9508
<212> TYPE: DNA
<213> ORGANISM: Artificial Sequence
<220> FEATURE:
<223> OTHER INFORMATION: Codon optimized

<400> SEQUENCE: 3

tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctaacg acattactat atatataata taggaagcat ttaatagaca    360

gcatcgtaat atatgtgtac tttgcagtta tgacgccaga tggcagtagt ggaagatatt    420

ctttattgaa aaatagcttg tcaccttacg tacaatcttg atccggagct tttctttttt    480

tgccgattaa gaattaattc ggtcgaaaaa agaaaaggag agggccaaga gggagggcat    540

tggtgactat tgagcacgtg agtatacgtg attaagcaca caaaggcagc ttggagtatg    600

tctgttatta atttcacagg tagttctggt ccattggtga aagtttgcgg cttgcagagc    660

acagaggccg cagaatgtgc tctagattcc gatgctgact tgctgggtat tatatgtgtg    720

cccaatagaa agagaacaat tgacccggtt attgcaagga aaatttcaag tcttgtaaaa    780

gcatataaaa atagttcagg cactccgaaa tacttggttg gcgtgtttcg taatcaacct    840

aaggaggatg ttttggctct ggtcaatgat tacggcattg atatcgtcca actgcatgga    900

gatgagtcgt ggcaagaata ccaagagttc ctcggtttgc cagttattaa aagactcgta    960

tttccaaaag actgcaacat actactcagt gcagcttcac agaaacctca ttcgtttatt   1020

cccttgtttg attcagaagc aggtgggaca ggtgaacttt tggattggaa ctcgatttct   1080

gactgggttg gaaggcaaga gagccccgaa agcttacatt ttatgttagc tggtggactg   1140

acgccagaaa atgttggtga tgcgcttaga ttaaatggcg ttattggtgt tgatgtaagc   1200

ggaggtgtgg agacaaatgg tgtaaaagac tctaacaaaa tagcaaattt cgtcaaaaat   1260

gctaagaaat agtgacaccg attatttaaa gctgcagcat acgatatata tacatgtgta   1320

tatatgtata cctatgaatg tcagtaagta tgtatacgaa cagtatgata ctgaagatga   1380

caaggtaatg catcattcta tacgtgtcat tctgaacgag gcgcgctttc cttttttctt   1440

tttgcttttt cttttttttt ctcttgaact cgacggatct atgcggtgtg aaataccgca   1500

cagatgcgta aggagaaaat accgcatcag gaaattgtaa acgttaatat tttgttaaaa   1560

ttcgcgttaa atttttgtta aatcagctca ttttttaacc aataggccga aatcggcaaa   1620

atcccttata aatcaaaaga atagaccgag atagggttga gtgttgttcc agtttggaac   1680
```

```
aagagtccac tattaaagaa cgtggactcc aacgtcaaag ggcgaaaaac cgtctatcag   1740
ggcgatggcc cactacgtga accatcaccc taatcaagtt ttttggggtc gaggtgccgt   1800
aaagcactaa atcggaaccc taaagggagc ccccgattta gagcttgacg gggaaagccg   1860
gcgaacgtgg cgagaaagga agggaagaaa gcgaaaggag cgggcgctag ggcgctggca   1920
agtgtagcgg tcacgctgcg cgtaaccacc acacccgccg cgcttaatgc gccgctacag   1980
ggcgcgtcgc gccattcgcc attcaggctg cgcaactgtt gggaagggcg atcggtgcgg   2040
gcctcttcgc tattacgcca gctggcgaaa gggggatgtg ctgcaaggcg attaagttgg   2100
gtaacgccag ggttttccca gtcacgacgt tgtaaaacga cggccagtga gcgcgcgtaa   2160
tacgactcac tatagggcga attgggtacc ggccgcaaat taaagccttc gagcgtccca   2220
aaaccttctc aagcaaggtt ttcagtataa tgttacatgc gtacacgcgt ctgtacagaa   2280
aaaaaagaaa aatttgaaat ataaataacg ttcttaatac taacataact ataaaaaaat   2340
aaatagggac ctagacttca ggttgtctaa ctccttcctt ttcggttaga gcggatgtgg   2400
ggggagggcg tgaatgtaag cgtgacataa ctaattacat gactcgaggt cgacttacaa   2460
atcttcttca cttattaatt tttgttcgtg gtggtgaggt ggcaaaggtg ggatggattg   2520
ttcgtttctg aaaaagttgt tagggtcggc tttagtcttt actttaacta atctgttgaa   2580
atttttacca aagtactttt caccccaaat tcttgcttgt gtatagttat ttggagattc   2640
agggttagtt ttacctaagt ccaaatctct gtagttcaaa tatgccaatc ttgggttttg   2700
actaacgtaa ggtgtagtga agttgtaaac ggatctgacc cagttgatat gcttttcgtt   2760
atcttcttgc ttttcccatg aggctgtgta ccataattca tacatgatac cagctctgtg   2820
aggaaatggt atggctgatt cagatatttc ttccataata ccaccgtatg gatacaaaac   2880
gtacatgccg acacctacat cttcttcgta caacttttcc aatatcttga ccattgcagt   2940
ttcagggatt ggtttcttaa cgtagtccaa tttaatagaa aaagcggtct ttttaccagc   3000
ggatctatcc aacaagattt cctttttgaa gttagcggtg ttgaagttta caacacctga   3060
atagaagatg gttgtgtcta tccaagaaaa ttccttgcaa tctgtctttt taatacccaa   3120
ttctgggaat gacttattca tcaaatcaac caaagaatct acaccaccat ggaaaattga   3180
agaaaaataa ccgtgaacag tggtcttatt tttaccatgg ttatctgtaa tatttttagt   3240
gatgaaatgg gtcatcaaaa ccaagtcctt atcgtacttg taagcgatgt tttgccactt   3300
attaaacaac ttaaccaaac cgtggatttc catgttcttt ttgacagaga aaatagtact   3360
tttggaagga acagcgacta acttaatttt ccaagcggca atgataccga aattttcacc   3420
accaccacct cttatggccc aaaacaaatc ttcacccata gactttctgt ccaaaacttt   3480
accatctacg ttaaccaaat gggcgtctat aatattatct gcagctaaac cgtagtttct   3540
catcaatgca ccataaccac caccagaaaa gtgaccaccg acacctactg ttggacagta   3600
accaccaggg aaagaaaagt tttcattctt ttcgttgatc cagtagtaaa cttcacccaa   3660
ggtggcacct gcttctaccc atgctgtttg actgtgaacg tcgatcttta tggaatgcat   3720
atttctcaaa tcgactacaa cgaatggaac ttgtgagatg taagacatgc cttctgcatc   3780
atgaccacct gatctagttc tgatttgcaa acctactttc ttagagcaca atatagaagc   3840
ttgaatgtga ctaacattgg aaggtgtaac aatgactaaa ggttttggtg tagtgtcaga   3900
agtgaatctc aaattttgga tggtactgtt caaaacggac atgtacaatt gatcatgttg   3960
agtatatata aactttgggt tagcagggtt gtttgggatg tattcggaga aacacttcaa   4020
```

```
aaagttttct tgtggatttg cgatggagat ttggatgttg aaggacaaga agaagaagat   4080
tattttacag acgaaccaga aagagaatgc ggagcagttc ataggacctg gattttcttc   4140
aacgtcacca caggtcaaca aagaacctct accttcaata aaaacgtata ccaaatattc   4200
agcgtagtac aatttccaca taaactcgta gaatcttcta cctgcttcag ggtcataatt   4260
tgtcaaagcg aaatctctag tttgcaagat caaccagaaa gccaagatgg catgtgacaa   4320
caacataacg ttagaattaa aggcttgtgg ccaaatgata cctgccaaaa tggctgcgac   4380
gtaacttaac aaaacgatac cggagcagaa caaagtcaaa tttcttgaac cgtacttaga   4440
agccaaggta ctaataccga actttgtgtc accttcaacg tcagaggcat ccttgatcaa   4500
ggctaatgca gaacccatac ttttcatgaa tgccaacaaa aatgtgaatg aaggtctcaa   4560
ttcgaatggc aaacctaaag cagctcttga agcgtagtag aaggtgaagt ttgtgatgat   4620
atgagctaag aaattcaaca aaaaggcagt actagggttt tgtttccatc taaaaggtgg   4680
tacggaatag acaataccac cgaagatacc gaaacagtaa ccgaagatgt acaatggacc   4740
acccttcatt ttaattgtga tgatcaaacc gaacaaggct actatgatag acatgatcca   4800
tgcagtattg acggatattt cacctgaagc caaaggcaaa tctggtttgt taattctgtc   4860
gatgtgcaaa tcgtatattt gattaattgt agtggtgaat gaagcgatgc acaagatggc   4920
aactaaaaag aaaaatgcct tgaacatcaa ggaccatgaa attaagttag tgttatgcaa   4980
caattcttta ccgaataaac cgcatgcaca agaagtaaaa gcgattatgg tgtatggtct   5040
ttgcaacttc caacatgctt taccgaagtt caaaattttt gtggcaacag agtgattatc   5100
actttcaggt ggttcagttt gatttgtagt tgcagctctg atagagttct tagctataga   5160
caaactttcg gagcacttat tttgtaagtg gaaggacttg gttgaacaat gttttgatgg   5220
aaagttgttg taagagtact taataggtgt ctttggatgt ctgtaacaca acaatgatgt   5280
ttttggattg ttgttgtgag gattcaataa ggtatgatag ttagtttgga aggagaaagt   5340
acagacggat gataaaccca tactagttct agatccgtcg aaactaagtt cttggtgttt   5400
taaaactaaa aaaaagacta actataaaag tagaatttaa gaagtttaag aaatagattt   5460
acagaattac aatcaatacc taccgtcttt atatacttat tagtcaagta ggggaataat   5520
ttcagggaac tggtttaaac cttttttttc agctttttcc aaatcagaga gagcagaagg   5580
taatagaagg tgtaagaaaa tgagatagat acatgcgtgg gtcaattgcc ttgtgtcatc   5640
atttactcca ggcaggttgc atcactccat tgaggttgtg cccgtttttt gcctgtttgt   5700
gccctgttct ctgtagttgc gctaagagaa tggacctatg aactgatggt tggtgaagaa   5760
aacaatattt tggtgctggg attctttttt tttctggatg ccagcttaaa aagcgggctc   5820
cattatattt agtggatgcc aggaataaac ctgttcaccc aagcaccatc agtgttatat   5880
attctgtgta acccgccccc tattttggca tgtacgggtt acagcagaat taaaaggcta   5940
attttttgac taaataaagt taggaaaatc actactatta attatttacg tattctttga   6000
aatggcagta ttgataatga taaactcgag agctccagct tttgttcagt tgattgtatg   6060
cttggtatag cttgaaatat tgtgcagaaa aagaaacaag gaagaaaggg aacgagaaca   6120
atgacgagga aacaaaagat taataattgc aggtctattt atacttgata gcaagacagc   6180
aaactttttt ttatttcaaa ttcaagtaac tggaaggaag gccgtatacc gttgctcatt   6240
agagagtagt gtgcgtgaat gaaggaagga aaaagtttcg tgtgcttcga gataccccctc   6300
atcagctctg gaacaacgac atctgttggt gctgtctttg tcgttaattt tttcctttag   6360
tgtcttccat catttttttg tcattgcgga tatggtgaga caacaacggg ggagagagaa   6420
```

```
aagaaaaaaa aagaaaagaa gttgcatgcg cctattatta cttcaataga tggcaaatgg   6480
aaaaagggta gtgaaacttc gatatgatga tggctatcaa gtctagggct acagtattag   6540
ttcgttatgt accaccatca atgaggcagt gtaattggtg tagtcttgtt tagcccatta   6600
tgtcttgtct ggtatctgtt ctattgtata tctcccctcc gccacctaca tgttagggag   6660
accaacgaag gtattatagg aatcccgatg tatgggtttg gttgccagaa aagaggaagt   6720
ccatattgta cacccggaaa caacaaaagg atgcgcgctt ggcgtaatca tggtcatagc   6780
tgtttcctgt gtgaaattgt tatccgctca caattccaca caacatagga gccggaagca   6840
taaagtgtaa agcctggggt gcctaatgag tgaggtaact cacattaatt gcgttgcgct   6900
cactgcccgc tttccagtcg ggaaacctgt cgtgccagct gcattaatga atcggccaac   6960
gcgcggggag aggcggtttg cgtattgggc gctcttccgc ttcctcgctc actgactcgc   7020
tgcgctcggt cgttcggctg cggcgagcgg tatcagctca ctcaaaggcg gtaatacggt   7080
tatccacaga atcaggggat aacgcaggaa agaacatgtg agcaaaaggc cagcaaaagg   7140
ccaggaaccg taaaaaggcc gcgttgctgg cgtttttcca taggctccgc ccccctgacg   7200
agcatcacaa aaatcgacgc tcaagtcaga ggtggcgaaa cccgacagga ctataaagat   7260
accaggcgtt tccccctgga agctccctcg tgcgctctcc tgttccgacc ctgccgctta   7320
ccggatacct gtccgccttt ctcccttcgg gaagcgtggc gctttctcat agctcacgct   7380
gtaggtatct cagttcggtg taggtcgttc gctccaagct gggctgtgtg cacgaacccc   7440
ccgttcagcc cgaccgctgc gccttatccg gtaactatcg tcttgagtcc aacccggtaa   7500
gacacgactt atcgccactg gcagcagcca ctggtaacag gattagcaga gcgaggtatg   7560
taggcggtgc tacagagttc ttgaagtggt ggcctaacta cggctacact agaaggacag   7620
tatttggtat ctgcgctctg ctgaagccag ttaccttcgg aaaaagagtt ggtagctctt   7680
gatccggcaa acaaaccacc gctggtagcg gtggtttttt tgtttgcaag cagcagatta   7740
cgcgcagaaa aaaaggatct caagaagatc ctttgatctt ttctacgggg tctgacgctc   7800
agtggaacga aaactcacgt taagggattt tggtcatgag attatcaaaa aggatcttca   7860
cctagatcct tttaaattaa aaatgaagtt ttaaatcaat ctaaagtata tatgagtaaa   7920
cttggtctga cagttaccaa tgcttaatca gtgaggcacc tatctcagcg atctgtctat   7980
ttcgttcatc catagttgcc tgactccccg tcgtgtagat aactacgata cgggagggct   8040
taccatctgg ccccagtgct gcaatgatac cgcgagaccc acgctcaccg gctccagatt   8100
tatcagcaat aaaccagcca gccggaaggg ccgagcgcag aagtggtcct gcaactttat   8160
ccgcctccat ccagtctatt aattgttgcc gggaagctag agtaagtagt tcgccagtta   8220
atagtttgcg caacgttgtt gccattgcta caggcatcgt ggtgtcacgc tcgtcgtttg   8280
gtatggcttc attcagctcc ggttcccaac gatcaaggcg agttacatga tcccccatgt   8340
tgtgcaaaaa agcggttagc tccttcggtc ctccgatcgt tgtcagaagt aagttggccg   8400
cagtgttatc actcatggtt atggcagcac tgcataattc tcttactgtc atgccatccg   8460
taagatgctt ttctgtgact ggtgagtact caaccaagtc attctgagaa tagtgtatgc   8520
ggcgaccgag ttgctcttgc ccggcgtcaa tacgggataa taccgcgcca catagcagaa   8580
ctttaaaagt gctcatcatt ggaaaacgtt cttcggggcg aaaactctca aggatcttac   8640
cgctgttgag atccagttcg atgtaaccca ctcgtgcacc caactgatct tcagcatctt   8700
ttactttcac cagcgtttct gggtgagcaa aaacaggaag gcaaaatgcc gcaaaaaagg   8760
```

```
gaataagggc gacacggaaa tgttgaatac tcatactctt cctttttcaa tattattgaa   8820
gcatttatca gggttattgt ctcatgagcg gatacatatt tgaatgtatt tagaaaaata   8880
aacaaatagg ggttccgcgc acatttcccc gaaaagtgcc acctgggtcc ttttcatcac   8940
gtgctataaa aataattata atttaaattt tttaatataa atatataaat taaaaataga   9000
aagtaaaaaa agaaattaaa gaaaaaatag tttttgtttt ccgaagatgt aaaagactct   9060
agggggatcg ccaacaaata ctacctttta tcttgctctt cctgctctca ggtattaatg   9120
ccgaattgtt tcatcttgtc tgtgtagaag accacacacg aaaatcctgt gattttacat   9180
tttacttatc gttaatcgaa tgtatatcta tttaatctgc ttttcttgtc taataaatat   9240
atatgtaaag tacgcttttt gttgaaattt tttaaacctt tgtttatttt tttttcttca   9300
ttccgtaact cttctacctt ctttatttac tttctaaaat ccaaatacaa aacataaaaa   9360
taaataaaca cagagtaaat tcccaaatta ttccatcatt aaaagatacg aggcgcgtgt   9420
aagttacagg caagcgatcc gtcctaagaa accattatta tcatgacatt aacctataaa   9480
aataggcgta tcacgaggcc ctttcgtc                                      9508
```

```
<210> SEQ ID NO 4
<211> LENGTH: 9505
<212> TYPE: DNA
<213> ORGANISM: Artificial Sequence
<220> FEATURE:
<223> OTHER INFORMATION: Codon optimized

<400> SEQUENCE: 4

tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctaacg acattactat atatataata taggaagcat ttaatagaca    360
gcatcgtaat atatgtgtac tttgcagtta tgacgccaga tggcagtagt ggaagatatt    420
ctttattgaa aaatagcttg tcaccttacg tacaatcttg atccggagct tttctttttt    480
tgccgattaa gaattaattc ggtcgaaaaa agaaaaggag agggccaaga gggagggcat    540
tggtgactat tgagcacgtg agtatacgtg attaagcaca caaaggcagc ttggagtatg    600
tctgttatta atttcacagg tagttctggt ccattggtga aagtttgcgg cttgcagagc    660
acagaggccg cagaatgtgc tctagattcc gatgctgact tgctgggtat tatatgtgtg    720
cccaatagaa agagaacaat tgacccggtt attgcaagga aaatttcaag tcttgtaaaa    780
gcatataaaa atagttcagg cactccgaaa tacttggttg gcgtgtttcg taatcaacct    840
aaggaggatg ttttggctct ggtcaatgat tacggcattg atatcgtcca actgcatgga    900
gatgagtcgt ggcaagaata ccaagagttc ctcggtttgc cagttattaa aagactcgta    960
tttccaaaag actgcaacat actactcagt gcagcttcac agaaacctca ttcgtttatt   1020
cccttgtttg attcagaagc aggtgggaca ggtgaacttt tggattggaa ctcgatttct   1080
gactgggttg gaaggcaaga gagccccgaa agcttacatt ttatgttagc tggtggactg   1140
acgccagaaa atgttggtga tgcgcttaga ttaaatggcg ttattggtgt tgatgtaagc   1200
ggaggtgtgg agacaaatgg tgtaaaagac tctaacaaaa tagcaaattt cgtcaaaaat   1260
gctaagaaat agtgacaccg attatttaaa gctgcagcat acgatatata tacatgtgta   1320
```

-continued

```
tatatgtata cctatgaatg tcagtaagta tgtatacgaa cagtatgata ctgaagatga   1380
caaggtaatg catcattcta tacgtgtcat tctgaacgag gcgcgctttc cttttttctt   1440
tttgcttttt cttttttttt ctcttgaact cgacggatct atgcggtgtg aaataccgca   1500
cagatgcgta aggagaaaat accgcatcag gaaattgtaa acgttaatat tttgttaaaa   1560
ttcgcgttaa atttttgtta aatcagctca ttttttaacc aataggccga aatcggcaaa   1620
atcccttata aatcaaaaga atagaccgag atagggttga gtgttgttcc agtttggaac   1680
aagagtccac tattaaagaa cgtggactcc aacgtcaaag ggcgaaaaac cgtctatcag   1740
ggcgatggcc cactacgtga accatcaccc taatcaagtt ttttggggtc gaggtgccgt   1800
aaagcactaa atcggaaccc taaagggagc ccccgattta gagcttgacg gggaaagccg   1860
gcgaacgtgg cgagaaagga agggaagaaa gcgaaaggag cgggcgctag ggcgctggca   1920
agtgtagcgg tcacgctgcg cgtaaccacc acacccgccg cgcttaatgc gccgctacag   1980
ggcgcgtcgc gccattcgcc attcaggctg cgcaactgtt gggaagggcg atcggtgcgg   2040
gcctcttcgc tattacgcca gctggcgaaa gggggatgtg ctgcaaggcg attaagttgg   2100
gtaacgccag ggttttccca gtcacgacgt tgtaaaacga cggccagtga gcgcgcgtaa   2160
tacgactcac tatagggcga attgggtacc ggccgcaaat taaagccttc gagcgtccca   2220
aaaccttctc aagcaaggtt ttcagtataa tgttacatgc gtacacgcgt ctgtacagaa   2280
aaaaaagaaa aatttgaaat ataaataacg ttcttaatac taacataact ataaaaaaat   2340
aaatagggac ctagacttca ggttgtctaa ctccttcctt ttcggttaga gcggatgtgg   2400
ggggagggcg tgaatgtaag cgtgacataa ctaattacat gactcgaggt cgacttacaa   2460
atcttcttca cttattaatt tttgttcgtg tctatgtcta ggtaaaggtg gaatggattg   2520
ttcgtttcta aagaagttgt ttgggtcaac caatgtctta acctttacta atctatcgaa   2580
atttttaccg aagtattttt caccccaaat tctagcttgg gtatagttgt taggattctt   2640
tggatcgtta ataccgatgt ccaaatctct gtagttcaaa tatgccaatc tagggttttt   2700
agaaacgtat ggagtcatga agttatagat gtttctaatc cagtttaagt gcttttcgtt   2760
atcttcttgc ttttcccatg aacaaatgta ccacaattcg tataagatac cagctctatg   2820
aggaaatgga atggcagatt cactgatttc gtccattata ccaccgtatg gatacaaggc   2880
gtacatgcct gcaccaatat cttcttcgta caatttttct aagatttgga cgaaaactga   2940
ttcaggtatt ggctttttaa cgtagtctaa cttaatttta aaggcaccgt tttgacctgc   3000
ggatctatcc aataatattt ctttgttgaa gttgtctgta tcgtagttga caacacctga   3060
ataaaagatg atggtgtcga tccaagacaa ttgtctacaa tcagttttct taatacctaa   3120
ttctggaaaa gacttattca tcaagtctac taaggaatcg acaccaccca agaaaactga   3180
agaaaagtat gtgtggatag cagtcttatt tttaccttgg ttatcggtga tgtttcttgt   3240
gatgaaatga gtcatcaaca acaagtcctt atcgtacttg tatgcgatgt tttgccactt   3300
attgaccaat ttaactaatt catggatttc cattatcttt ttgactgaga acatagtaga   3360
ctttggtact gcgactaatc ttatcttcca agcaactatg ataccgaatg attctgcacc   3420
accacctctc aaagcccaaa ataagtcttc acccatagac tttctatcca aaactttacc   3480
gtgaacattt accaaatgag cgtcgattat gttatcagcg gccaaaccgt agtttctcat   3540
taaaggacca taaccaccac caccaaaatg accacctgcg caaactgttg gacagtaacc   3600
agcagccaat gataagtttt cattcttttc gttaacccag tagtatactt cacccaatgt   3660
```

```
tgcaccagct tcaacccaag cagtttgtga gtgtacgtct attttaattg atctcatgtt   3720
tctcaaatca acgataacga atggaacttg ggagatgtat gacatgcctt cactatcatg   3780
accaccggat ctagttctaa tttgcaaacc aacctttta gaacataaga tagtaccttg   3840
gatgtgagat acatgactag gggttacaat gaccaaaggt tttggagtgg tatcagaagt   3900
gaatctcaaa ttatggattg tactgttcaa gacggacatg tacaatgggt tgttttgagt   3960
gtaaaccaac ttcaaattgg tggcgttatt aggtatgtat tgtgagaagc acttcaaaaa   4020
gttttctctt gggtttgcga tacttgtttg gatgttaaag gaaaagaaaa agaagatgat   4080
cttgcatacg aaccaaaagg agaaagttga acatttcata ggacctggat tttcttcaac   4140
gtcaccacag gtcaacaaag aacctctacc ttcaataaaa acgtatacca aatattcagc   4200
gtagtacaat ttccacataa actcgtagaa tcttctacct gcttcagggt cataatttgt   4260
caaagcgaaa tctctagttt gcaagatcaa ccagaaagcc aagatggcat gtgacaacaa   4320
cataacgtta gaattaaagg cttgtggcca aatgatacct gccaaaatgg ctgcgacgta   4380
acttaacaaa acgataccgg agcagaacaa agtcaaattt cttgaaccgt acttagaagc   4440
caaggtacta ataccgaact ttgtgtcacc ttcaacgtca gaggcatcct tgatcaaggc   4500
taatgcagaa cccatacttt tcatgaatgc caacaaaaat gtgaatgaag gtctcaattc   4560
gaatggcaaa cctaaagcag ctcttgaagc gtagtagaag gtgaagtttg tgatgatatg   4620
agctaagaaa ttcaacaaaa aggcagtact agggttttgt ttccatctaa aaggtggtac   4680
ggaatagaca ataccaccga agataccgaa acagtaaccg aagatgtaca atggaccacc   4740
cttcatttta attgtgatga tcaaaccgaa caaggctact atgatagaca tgatccatgc   4800
agtattgacg gatatttcac ctgaagccaa aggcaaatct ggtttgttaa ttctgtcgat   4860
gtgcaaatcg tatatttgat taattgtagt ggtgaatgaa gcgatgcaca agatggcaac   4920
taaaaagaaa aatgccttga acatcaagga ccatgaaatt aagttagtgt tatgcaacaa   4980
ttctttaccg aataaaccgc atgcacaaga agtaaaagcg attatggtgt atggtctttg   5040
caacttccaa catgctttac cgaagttcaa aatttttgtg gcaacagagt gattatcact   5100
ttcaggtggt tcagtttgat ttgtagttgc agctctgata gagttcttag ctatagacaa   5160
actttcggag cacttatttt gtaagtggaa ggacttggtt gaacaatgtt ttgatggaaa   5220
gttgttgtaa gagtacttaa taggtgtctt tggatgtctg taacacaaca atgatgtttt   5280
tggattgttg ttgtgaggat tcaataaggt atgatagtta gtttggaagg agaaagtaca   5340
gacggatgat aaacccatac tagttctaga tccgtcgaaa ctaagttctt ggtgttttaa   5400
aactaaaaaa aagactaact ataaaagtag aatttaagaa gtttaagaaa tagatttaca   5460
gaattacaat caatacctac cgtctttata tacttattag tcaagtaggg gaataatttc   5520
agggaactgg tttaaacctt ttttttcagc tttttccaaa tcagagagag cagaaggtaa   5580
tagaaggtgt aagaaaatga gatagataca tgcgtgggtc aattgccttg tgtcatcatt   5640
tactccaggc aggttgcatc actccattga ggttgtgccc gttttttgcc tgtttgtgcc   5700
ctgttctctg tagttgcgct aagagaatgg acctatgaac tgatggttgg tgaagaaaac   5760
aatattttgg tgctgggatt cttttttttt ctggatgcca gcttaaaaag cgggctccat   5820
tatatttagt ggatgccagg aataaacctg ttcacccaag caccatcagt gttatatatt   5880
ctgtgtaacc cgccccctat tttggcatgt acgggttaca gcagaattaa aaggctaatt   5940
ttttgactaa ataaagttag gaaaatcact actattaatt atttacgtat tctttgaaat   6000
ggcagtattg ataatgataa actcgagagc tccagctttt gttcagttga ttgtatgctt   6060
```

```
ggtatagctt gaaatattgt gcagaaaaag aaacaaggaa gaaagggaac gagaacaatg   6120

acgaggaaac aaaagattaa taattgcagg tctatttata cttgatagca agacagcaaa   6180

ctttttttta tttcaaattc aagtaactgg aaggaaggcc gtataccgtt gctcattaga   6240

gagtagtgtg cgtgaatgaa ggaaggaaaa agtttcgtgt gcttcgagat acccctcatc   6300

agctctggaa caacgacatc tgttggtgct gtctttgtcg ttaatttttt cctttagtgt   6360

cttccatcat ttttttgtca ttgcggatat ggtgagacaa caacggggga gagagaaaag   6420

aaaaaaaaag aaaagaagtt gcatgcgcct attattactt caatagatgg caaatggaaa   6480

aagggtagtg aaacttcgat atgatgatgg ctatcaagtc tagggctaca gtattagttc   6540

gttatgtacc accatcaatg aggcagtgta attggtgtag tcttgtttag cccattatgt   6600

cttgtctggt atctgttcta ttgtatatct cccctccgcc acctacatgt tagggagacc   6660

aacgaaggta ttataggaat cccgatgtat gggtttggtt gccagaaaag aggaagtcca   6720

tattgtacac ccggaaacaa caaaaggatg cgcgcttggc gtaatcatgg tcatagctgt   6780

ttcctgtgtg aaattgttat ccgctcacaa ttccacacaa cataggagcc ggaagcataa   6840

agtgtaaagc ctggggtgcc taatgagtga ggtaactcac attaattgcg ttgcgctcac   6900

tgcccgcttt ccagtcggga aacctgtcgt gccagctgca ttaatgaatc ggccaacgcg   6960

cggggagagg cggtttgcgt attgggcgct cttccgcttc ctcgctcact gactcgctgc   7020

gctcggtcgt tcggctgcgg cgagcggtat cagctcactc aaaggcggta atacggttat   7080

ccacagaatc aggggataac gcaggaaaga acatgtgagc aaaaggccag caaaaggcca   7140

ggaaccgtaa aaaggccgcg ttgctggcgt ttttccatag gctccgcccc cctgacgagc   7200

atcacaaaaa tcgacgctca agtcagaggt ggcgaaaccc gacaggacta taaagatacc   7260

aggcgtttcc ccctggaagc tccctcgtgc gctctcctgt tccgaccctg ccgcttaccg   7320

gatacctgtc cgcctttctc ccttcgggaa gcgtggcgct ttctcatagc tcacgctgta   7380

ggtatctcag ttcggtgtag gtcgttcgct ccaagctggg ctgtgtgcac gaaccccccg   7440

ttcagcccga ccgctgcgcc ttatccggta actatcgtct tgagtccaac ccggtaagac   7500

acgacttatc gccactggca gcagccactg gtaacaggat tagcagagcg aggtatgtag   7560

gcggtgctac agagttcttg aagtggtggc ctaactacgg ctacactaga aggacagtat   7620

ttggtatctg cgctctgctg aagccagtta ccttcggaaa aagagttggt agctcttgat   7680

ccggcaaaca aaccaccgct ggtagcggtg gtttttttgt ttgcaagcag cagattacgc   7740

gcagaaaaaa aggatctcaa gaagatcctt tgatcttttc tacggggtct gacgctcagt   7800

ggaacgaaaa ctcacgttaa gggattttgg tcatgagatt atcaaaaagg atcttcacct   7860

agatcctttt aaattaaaaa tgaagtttta aatcaatcta aagtatatat gagtaaactt   7920

ggtctgacag ttaccaatgc ttaatcagtg aggcacctat ctcagcgatc tgtctatttc   7980

gttcatccat agttgcctga ctccccgtcg tgtagataac tacgatacgg gagggcttac   8040

catctggccc cagtgctgca atgataccgc gagacccacg ctcaccggct ccagatttat   8100

cagcaataaa ccagccagcc ggaagggccg agcgcagaag tggtcctgca actttatccg   8160

cctccatcca gtctattaat tgttgccggg aagctagagt aagtagttcg ccagttaata   8220

gtttgcgcaa cgttgttgcc attgctacag gcatcgtggt gtcacgctcg tcgtttggta   8280

tggcttcatt cagctccggt tcccaacgat caaggcgagt tacatgatcc cccatgttgt   8340

gcaaaaaagc ggttagctcc ttcggtcctc cgatcgttgt cagaagtaag ttggccgcag   8400
```

```
tgttatcact catggttatg gcagcactgc ataattctct tactgtcatg ccatccgtaa   8460
gatgcttttc tgtgactggt gagtactcaa ccaagtcatt ctgagaatag tgtatgcggc   8520
gaccgagttg ctcttgcccg gcgtcaatac gggataatac cgcgccacat agcagaactt   8580
taaaagtgct catcattgga aaacgttctt cggggcgaaa actctcaagg atcttaccgc   8640
tgttgagatc cagttcgatg taacccactc gtgcacccaa ctgatcttca gcatctttta   8700
ctttcaccag cgtttctggg tgagcaaaaa caggaaggca aaatgccgca aaaaagggaa   8760
taagggcgac acggaaatgt tgaatactca tactcttcct ttttcaatat tattgaagca   8820
tttatcaggg ttattgtctc atgagcggat acatatttga atgtatttag aaaaataaac   8880
aaataggggt tccgcgcaca tttccccgaa aagtgccacc tgggtccttt tcatcacgtg   8940
ctataaaaat aattataatt taaatttttt aatataaata tataaattaa aaatagaaag   9000
taaaaaaaga aattaaagaa aaaatagttt ttgttttccg aagatgtaaa agactctagg   9060
gggatcgcca acaaatacta ccttttatct tgctcttcct gctctcaggt attaatgccg   9120
aattgtttca tcttgtctgt gtagaagacc acacacgaaa atcctgtgat tttacatttt   9180
acttatcgtt aatcgaatgt atatctattt aatctgcttt tcttgtctaa taaatatata   9240
tgtaaagtac gctttttgtt gaaatttttt aaacctttgt ttattttttt ttcttcattc   9300
cgtaactctt ctaccttctt tatttacttt ctaaaatcca aatacaaaac ataaaaataa   9360
ataaacacag agtaaattcc caaattattc catcattaaa agatacgagg cgcgtgtaag   9420
ttacaggcaa gcgatccgtc ctaagaaacc attattatca tgacattaac ctataaaaat   9480
aggcgtatca cgaggccctt tcgtc                                         9505
```

<210> SEQ ID NO 5
<211> LENGTH: 8696
<212> TYPE: DNA
<213> ORGANISM: Artificial Sequence
<220> FEATURE:
<223> OTHER INFORMATION: Codon optimized

<400> SEQUENCE: 5

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctaact gtgggaatac tcaggtatcg taagatgcaa gagttcgaat    360
ctcttagcaa ccattatttt tttcctcaac ataacgagaa cacacagggg cgctatcgca    420
cagaatcaaa ttcgatgact ggaaattttt tgttaatttc agaggtcgcc tgacgcatat    480
acctttttca actgaaaaat tgggagaaaa aggaaaggtg agaggccgga accggctttt    540
catatagaat agagaagcgt tcatgactaa atgcttgcat cacaatactt gaagttgaca    600
atattattta aggacctatt gtttttttcca ataggtggtt agcaatcgtc ttactttcta    660
acttttctta ccttttacat ttcagcaata tatatatata tttcaaggat ataccattct    720
aatgtctgcc cctatgtctg cccctaagaa gatcgtcgtt ttgccaggtg accacgttgg    780
tcaagaaatc acagccgaag ccattaaggt tcttaaagct atttctgatg ttcgttccaa    840
tgtcaagttc gatttcgaaa atcatttaat tggtggtgct gctatcgatg ctacaggtgt    900
cccacttcca gatgaggcgc tggaagcctc caagaaggtt gatgccgttt tgttaggtgc    960
```

-continued

```
tgtgggtggt cctaaatggg gtaccggtag tgttagacct gaacaaggtt tactaaaaat   1020
ccgtaaagaa cttcaattgt acgccaactt aagaccatgt aactttgcat ccgactctct   1080
tttagactta tctccaatca agccacaatt tgctaaaggt actgacttcg ttgttgtcag   1140
agaattagtg ggaggtattt actttggtaa gagaaaggaa gacgatggtg atggtgtcgc   1200
ttgggatagt gaacaataca ccgttccaga agtgcaaaga atcacaagaa tggccgcttt   1260
catggcccta caacatgagc caccattgcc tatttggtcc ttggataaag ctaatgtttt   1320
ggcctcttca agattatgga gaaaaactgt ggaggaaacc atcaagaacg aattccctac   1380
attgaaggtt caacatcaat tgattgattc tgccgccatg atcctagtta agaacccaac   1440
ccacctaaat ggtattataa tcaccagcaa catgtttggt gatatcatct ccgatgaagc   1500
ctccgttatc ccaggttcct tgggtttgtt gccatctgcg tccttggcct ctttgccaga   1560
caagaacacc gcatttggtt tgtacgaacc atgccacggt tctgctccag atttgccaaa   1620
gaataaggtt gaccctatcg ccactatctt gtctgctgca atgatgttga aattgtcatt   1680
gaacttgcct gaagaaggta aggccattga agatgcagtt aaaaaggttt tggatgcagg   1740
tatcagaact ggtgatttag gtggttccaa cagtaccacc gaagtcggtg atgctgtcgc   1800
cgaagaagtt aagaaaatcc ttgcttaatg acaccgatta tttaaagctg cagcatacga   1860
tatatataca tgtgtatata tgtataccta tgaatgtcag taagtatgta tacgaacagt   1920
atgatactga agatgacaag gtaatgcatc attctatacg tgtcattctg aacgaggcgc   1980
gctttccttt tttctttttg ctttttcttt ttttttctct tgaactcgac ggatctatgc   2040
ggtgtgaaat accgcacaga tgcgtaagga gaaaataccg catcaggaaa ttgtaaacgt   2100
taatattttg ttaaaattcg cgttaaattt ttgttaaatc agctcatttt ttaaccaata   2160
ggccgaaatc ggcaaaatcc cttataaatc aaaagaatag accgagatag ggttgagtgt   2220
tgttccagtt tggaacaaga gtccactatt aaagaacgtg gactccaacg tcaaagggcg   2280
aaaaaccgtc tatcagggcg atggcccact acgtgaacca tcaccctaat caagtttttt   2340
ggggtcgagg tgccgtaaag cactaaatcg gaaccctaaa gggagccccc gatttagagc   2400
ttgacgggga aagccggcga acgtggcgag aaaggaaggg aagaaagcga aaggagcggg   2460
cgctagggcg ctggcaagtg tagcggtcac gctgcgcgta accaccacac ccgccgcgct   2520
taatgcgccg ctacagggcg cgtcgcgcca ttcgccattc aggctgcgca actgttggga   2580
agggcgatcg gtgcgggcct cttcgctatt acgccagctg gcgaaagggg gatgtgctgc   2640
aaggcgatta agttgggtaa cgccagggtt ttcccagtca cgacgttgta aaacgacggc   2700
cagtgagcgc gcgtaatacg actcactata gggcgaattg ggtaccggcc gcaaattaaa   2760
gccttcgagc gtcccaaaac cttctcaagc aaggttttca gtataatgtt acatgcgtac   2820
acgcgtctgt acagaaaaaa aagaaaaatt tgaaatataa ataacgttct taatactaac   2880
ataactataa aaaaataaat agggacctag acttcaggtt gtctaactcc ttccttttcg   2940
gttagagcgg atgtgggggg agggcgtgaa tgtaagcgtg acataactaa ttacatgact   3000
cgaggtcgac ttatgcatag tctggaacat cgtaagggta ctttcttggg gtgtaatcga   3060
agatcaacaa tttttcccag aaggatctgt aaacgtcacc aaaaccaacg tgagctggat   3120
gaatgatgta atcttggata gtttcaactg attcgaaggt tacttcgaca atgtgtgtat   3180
aaccttcttc tttcttttgt gtaacgtctt taccccagta tacatctttc atagcaggta   3240
taatgttgac caaattaacg taggtcttga aaaattcttc cttttgagct tctgtgattt   3300
```

-continued

```
catctttaaa cttcaatact atcaaatgct tgacggccat aggacctggg ttttcttcaa   3360
cgtcaccaca agttaacaag gaacctctac cttcatattt aattggtact gatctgacaa   3420
ctactctttc gacggtcaaa ccaggaccga aaccaaataa gacaccccat tcaaaaccgt   3480
caccagtagt agatttaccc tcttctaatg atctctttct caattcatcc attacgaaca   3540
agacagtgga tgaagacatg ttaccgtgtt cagataaaac atgtctacta tctacaaact   3600
tttctttctt caaatccaat ttttcttcaa ccttatccaa aatggcttta ccacctggat   3660
gtgttatcca gaaaatagag ttccaatctg agatacctat aggagtgaat gcttctatca   3720
aacacttttc tatgttgtta gagattaaca ttggaacgtc tttgtgcaaa tcgaagatca   3780
aacctgcttc tcttatatga ccaccaattg taccttcaga attaggcaag atggtttgac   3840
ctgtactgac taattcaaat attggtcttt caccaacaga ttcgtcaggt tctgcaccaa   3900
caataacagc agcagcaccg tcaccgaaga tagcttgacc aactaacaat tccaagtcag   3960
aatcacttgg acctctaaac aagcaagcca taatgtcgca acaaacagct aatactctgg   4020
caccccttgtt gttttctgca atatccttag cgattctcaa aacagtacca ccaccgtagc   4080
aacctaattg atacatcatg actctcttaa cggatggtga caaacctaac aatttggcac   4140
agtggtagtc tgcaccaggc atatctgtag tagatgcact tgtaaaaatc aaatgagtga   4200
tctttgactt tggttgaccc cattccttaa tggcttttgc acaagcatct ttacccaatt   4260
taggaacttc gacaactaac atgtcttgtc tggcatccaa tgtttgcatt tcgtgttcta   4320
ccaatcttgg attttgcttc aaatgttctt cgttcaagaa gcagtttctc tttctgatca   4380
tagacttatc acatattttt ctaaactttt ccttcaattg agtcatgtgt tcactcttgg   4440
taactctgaa gtaataatca ggaaattcat cttggatcaa tatgttttct gggttggctg   4500
tacctatggc taatacggag gcaggacctt cggctctcaa atggttcata ctagttctag   4560
atccgtcgaa actaagttct tggtgtttta aaactaaaaa aaagactaac tataaaagta   4620
gaatttaaga agtttaagaa atagatttac agaattacaa tcaataccta ccgtctttat   4680
atacttatta gtcaagtagg ggaataattt cagggaactg gtttaaacct ttttttcag   4740
ctttttccaa atcagagaga gcagaaggta atagaaggtg taagaaaatg agatagatac   4800
atgcgtgggt caattgcctt gtgtcatcat ttactccagg caggttgcat cactccattg   4860
aggttgtgcc cgtttttgc ctgtttgtgc cctgttctct gtagttgcgc taagagaatg   4920
gacctatgaa ctgatggttg gtgaagaaaa caatattttg gtgctgggat tctttttttt   4980
tctggatgcc agcttaaaaa gcgggctcca ttatatttag tggatgccag gaataaacct   5040
gttcacccaa gcaccatcag tgttatatat tctgtgtaac ccgcccccta ttttggcatg   5100
tacgggttac agcagaatta aaaggctaat tttttgacta aataaagtta ggaaaatcac   5160
tactattaat tatttacgta ttctttgaaa tggcagtatt gataatgata aactcgagag   5220
ctccagcttt tgttcagttg attgtatgct tggtatagct tgaaatattg tgcagaaaaa   5280
gaaacaagga agaaagggaa cgagaacaat gacgaggaaa caaaagatta ataattgcag   5340
gtctatttat acttgatagc aagacagcaa acttttttt atttcaaatt caagtaactg   5400
gaaggaaggc cgtataccgt tgctcattag agagtagtgt gcgtgaatga aggaaggaaa   5460
aagtttcgtg tgcttcgaga taccccctcat cagctctgga acaacgacat ctgttggtgc   5520
tgtctttgtc gttaattttt tcctttagtg tcttccatca ttttttttgtc attgcggata   5580
tggtgagaca acaacggggg agagagaaaa gaaaaaaaaa gaaaagaagt tgcatgcgcc   5640
tattattact tcaatagatg gcaaatggaa aaagggtagt gaaacttcga tatgatgatg   5700
```

```
gctatcaagt ctagggctac agtattagtt cgttatgtac caccatcaat gaggcagtgt   5760
aattggtgta gtcttgttta gcccattatg tcttgtctgg tatctgttct attgtatatc   5820
tcccctccgc cacctacatg ttagggagac caacgaaggt attataggaa tcccgatgta   5880
tgggtttggt tgccagaaaa gaggaagtcc atattgtaca cccggaaaca acaaaaggat   5940
gcgcgcttgg cgtaatcatg gtcatagctg tttcctgtgt gaaattgtta tccgctcaca   6000
attccacaca acataggagc cggaagcata aagtgtaaag cctggggtgc ctaatgagtg   6060
aggtaactca cattaattgc gttgcgctca ctgcccgctt tccagtcggg aaacctgtcg   6120
tgccagctgc attaatgaat cggccaacgc gcggggagag gcggtttgcg tattgggcgc   6180
tcttccgctt cctcgctcac tgactcgctg cgctcggtcg ttcggctgcg gcgagcggta   6240
tcagctcact caaaggcggt aatacggtta tccacagaat caggggataa cgcaggaaag   6300
aacatgtgag caaaaggcca gcaaaaggcc aggaaccgta aaaaggccgc gttgctggcg   6360
tttttccata ggctccgccc ccctgacgag catcacaaaa atcgacgctc aagtcagagg   6420
tggcgaaacc cgacaggact ataaagatac caggcgtttc cccctggaag ctccctcgtg   6480
cgctctcctg ttccgaccct gccgcttacc ggatacctgt ccgcctttct cccttcggga   6540
agcgtggcgc tttctcatag ctcacgctgt aggtatctca gttcggtgta ggtcgttcgc   6600
tccaagctgg gctgtgtgca cgaacccccc gttcagcccg accgctgcgc cttatccggt   6660
aactatcgtc ttgagtccaa cccggtaaga cacgacttat cgccactggc agcagccact   6720
ggtaacagga ttagcagagc gaggtatgta ggcggtgcta cagagttctt gaagtggtgg   6780
cctaactacg gctacactag aaggacagta tttggtatct gcgctctgct gaagccagtt   6840
accttcggaa aaagagttgg tagctcttga tccggcaaac aaaccaccgc tggtagcggt   6900
ggtttttttg tttgcaagca gcagattacg cgcagaaaaa aaggatctca agaagatcct   6960
ttgatctttt ctacggggtc tgacgctcag tggaacgaaa actcacgtta agggattttg   7020
gtcatgagat tatcaaaaag gatcttcacc tagatccttt taaattaaaa atgaagtttt   7080
aaatcaatct aaagtatata tgagtaaact tggtctgaca gttaccaatg cttaatcagt   7140
gaggcaccta tctcagcgat ctgtctattt cgttcatcca tagttgcctg actccccgtc   7200
gtgtagataa ctacgatacg ggagggctta ccatctggcc ccagtgctgc aatgataccg   7260
cgagacccac gctcaccggc tccagattta tcagcaataa accagccagc cggaagggcc   7320
gagcgcagaa gtggtcctgc aactttatcc gcctccatcc agtctattaa ttgttgccgg   7380
gaagctagag taagtagttc gccagttaat agtttgcgca acgttgttgc cattgctaca   7440
ggcatcgtgg tgtcacgctc gtcgtttggt atggcttcat tcagctccgg ttcccaacga   7500
tcaaggcgag ttacatgatc ccccatgttg tgcaaaaaag cggttagctc cttcggtcct   7560
ccgatcgttg tcagaagtaa gttggccgca gtgttatcac tcatggttat ggcagcactg   7620
cataattctc ttactgtcat gccatccgta agatgctttt ctgtgactgg tgagtactca   7680
accaagtcat tctgagaata gtgtatgcgg cgaccgagtt gctcttgccc ggcgtcaata   7740
cgggataata ccgcgccaca tagcagaact ttaaaagtgc tcatcattgg aaaacgttct   7800
tcggggcgaa aactctcaag gatcttaccg ctgttgagat ccagttcgat gtaacccact   7860
cgtgcaccca actgatcttc agcatctttt actttcacca gcgtttctgg gtgagcaaaa   7920
acaggaaggc aaaatgccgc aaaaaaggga ataagggcga cacggaaatg ttgaatactc   7980
atactcttcc tttttcaata ttattgaagc atttatcagg gttattgtct catgagcgga   8040
```

```
tacatatttg aatgtattta gaaaaataaa caaatagggg ttccgcgcac atttccccga   8100
aaagtgccac ctgggtcctt ttcatcacgt gctataaaaa taattataat ttaaattttt   8160
taatataaat atataaatta aaaatagaaa gtaaaaaaag aaattaaaga aaaaatagtt   8220
tttgttttcc gaagatgtaa aagactctag ggggatcgcc aacaaatact accttttatc   8280
ttgctcttcc tgctctcagg tattaatgcc gaattgtttc atcttgtctg tgtagaagac   8340
cacacacgaa aatcctgtga ttttacattt tacttatcgt taatcgaatg tatatctatt   8400
taatctgctt ttcttgtcta ataaatatat atgtaaagta cgctttttgt tgaaattttt   8460
taaacctttg tttatttttt tttcttcatt ccgtaactct tctaccttct ttatttactt   8520
tctaaaatcc aaatacaaaa cataaaaata aataaacaca gagtaaattc ccaaattatt   8580
ccatcattaa aagatacgag gcgcgtgtaa gttacaggca agcgatccgt cctaagaaac   8640
cattattatc atgacattaa cctataaaaa taggcgtatc acgaggccct ttcgtc       8696
```

<210> SEQ ID NO 6
<211> LENGTH: 4322
<212> TYPE: DNA
<213> ORGANISM: Artificial Sequence
<220> FEATURE:
<223> OTHER INFORMATION: Codon optimized

<400> SEQUENCE: 6

```
aggaaacgaa gataaatctc gagtttatca ttatcaatac tgccatttca aagaatacgt     60
aaataattaa tagtagtgat ttcctaact ttatttagtc aaaaaattag ccttttaatt    120
ctgctgtaac ccgtacatgc caaaataggg ggcgggttac acagaatata taacactgat    180
ggtgcttggg tgaacaggtt tattcctggc atccactaaa tataatggag cccgcttttt    240
aagctggcat ccagaaaaaa aaagaatccc agcaccaaaa tattgttttc ttcaccaacc    300
atcagttcat aggtccattc tcttagcgca actacagaga acagggcaca aacaggcaaa    360
aaacgggcac aacctcaatg gagtgatgca acctgcctgg agtaaatgat gacacaaggc    420
aattgaccca cgcatgtatc tatctcattt tcttacacct tctattacct tctgctctct    480
ctgatttgga aaaagctgaa aaaaaaggtt taaaccagtt ccctgaaatt attcccctac    540
ttgactaata agtatataaa gacggtaggt attgattgta attctgtaaa tctatttctt    600
aaacttctta aattctactt ttatagttag tctttttttt agttttaaaa caccaagaac    660
ttagtttcga cggatctaga actagtatgg gtaaaaacta taagtccttg gattcagtcg    720
ttgcctcaga tttcatcgca ttgggtatca cctcagaagt agcagaaaca ttacatggta    780
gattggcaga aatcgtttgt aattatggtg ctgcaacccc tcaaacttgg atcaacatcg    840
ctaaccatat cttgtcacca gatttgcctt tctccttaca ccaaatgttg ttttatggtt    900
gctacaagga tttcggtcca gccccacctg cttggattcc agaccctgaa aaagtcaagt    960
caactaattt gggtgctttg ttggaaaaga gaggtaaaga atttttgggt gtaaagtaca   1020
aagatccaat ttcttctttt tctcacttcc aagaattttc tgttagaaac cctgaagtct   1080
attggagaac agtattgatg gatgaaatga aaattagttt ctctaaggac ccagaatgta   1140
tcttgagaag agatgacatc aacaacccag gtggttctga atggttacct ggtggttact   1200
tgaactcagc taaaaattgc ttgaacgtaa actccaataa gaaattgaac gatactatga   1260
tcgtttggag agacgagggt aacgatgact tgcctttgaa taagttgaca ttagatcaat   1320
tgagaaagag agtttggttg gttggttatg cattggaaga aatgggttta gaaaaaggtt   1380
gtgcaatagc catcgatatg ccaatgcatg ttgatgctgt tgttatatat ttggccatag   1440
```

```
tattggctgg ttacgtagtt gtctctatag cagattcatt ttccgcccct gaaatctcaa   1500
ctagattgag attatccaaa gctaaggcaa ttttcacaca agatcacatc atcagaggta   1560
aaaagagaat accattgtat tcaagagtag ttgaagctaa atccccaatg gcaatagtta   1620
tcccttgtag tggttctaac attggtgcag aattgagaga tggtgacata tcttgggatt   1680
actttttaga aagagccaag gagtttaaaa actgcgagtt tactgccaga gaacaacctg   1740
ttgatgctta tactaacatc ttattctcca gtggtactac aggtgaacca aaagcaattc   1800
cttggacaca agccacccca ttgaaggctg ctgctgatgg ttggtctcat ttggatatta   1860
gaaaaggtga cgttatagta tggccaacta atttgggttg gatgatgggt ccttggttgg   1920
tttatgctag tttgttaaat ggtgcatcta ttgccttgta caacggtagt cctttagtct   1980
ctggtttcgc taaatttgtt caagatgcaa aggtcacaat gttgggtgtc gtaccatcta   2040
ttgtaagatc atggaaatcc acaaattgtg tttcaggtta cgattggtcc accataagat   2100
gcttttcttc atccggtgaa gcctctaatg tagacgaata tttgtggtta atgggtagag   2160
ctaactacaa gccagttata gaaatgtgtg gtggtacaga aatcggtggt gctttttctg   2220
ctggttcatt tttgcaagct caatctttaa gttctttttc atcccaatgt atgggttgca   2280
ccttgtacat attagataag aacggttacc caatgcctaa aaataagcca ggtatcggtg   2340
aattggcatt aggtcctgtt atgtttggtg cctcaaaaac attgttaaac ggtaatcatc   2400
acgatgtcta tttcaagggt atgccaacct tgaatggtga agtattgaga agacatggtg   2460
acattttcga attgacctct aacggttact accatgcaca cggtagagcc gatgacacta   2520
tgaacatcgg tggtatcaaa attagttcta tcgaaatcga aagagtctgt aatgaagtag   2580
atgacagagt tttgaaacc actgctattg gtgttccacc tttgggtggt ggtccagaac   2640
aattggtcat atttttcgta ttgaaggatt caaacgacac aaccattgat ttgaaccaat   2700
tgagattatc ctttaacttg ggtttgcaaa agaaattgaa cccattattc aaagttacta   2760
gagttgtccc attgtcatcc ttacctagaa ctgcaacaaa caagatcatg agaagagttt   2820
tgagacaaca attcagtcat ttcgaagaag gtagaggttc tttgttaaca tgtggtgacg   2880
ttgaagaaaa tccaggtcct atggcttcag aaaaggaaat aagaagagaa agattcttga   2940
acgtattccc aaagttagtt gaagaattga acgctagttt gttagcttat ggtatgccta   3000
aagaagcctg cgattggtat gctcactctt taaactacaa tactccaggt ggtaaattga   3060
atagaggttt gagtgtagtt gatacttatg ctatcttgtc taacaaaacc gttgaacaat   3120
taggtcaaga agaatacgaa aaggtcgcta tcttgggttg gtgtattgaa ttgttgcaag   3180
catacttttt ggttgccgat gacatgatgg ataagtctat aacaagaaga ggtcaaccat   3240
gctggtacaa agttccagaa gttggtgaaa tagccataaa tgatgctttt atgttggaag   3300
ccgctatcta taaattgttg aagtcacatt tcagaaacga aaagtactac atcgatatta   3360
ccgaattatt ccacgaagtt actttccaaa cagaattggg tcaattgatg gatttgataa   3420
ctgcacctga agataaagtt gacttgtcaa agttttcctt gaagaaacat tcattcatcg   3480
tcacctttga aactgcttat tactccttct atttgccagt cgccttggct atgtacgtag   3540
ctggtattac tgatgaaaaa gacttgaagc aagcaagaga tgttttgata cctttgggtg   3600
aatacttcca aatccaagat gactacttag actgtttcgg tactccagaa caaataggta   3660
aaatcggtac agatattcaa gacaataagt gcagttgggt tattaacaag gctttggaat   3720
tagcatctgc cgaacaaaga aagactttgg atgaaaacta cggtaaaaag gactcagttg   3780
```

```
ctgaagcaaa gtgtaagaaa atttttaatg atttgaagat tgaacaattg taccatgaat   3840

acgaagaatc catcgctaaa gacttaaagg caaagattag tcaagttgat gaatcaagag   3900

gttttaaagc cgacgttttg acagctttct tgaataaggt ctacaagaga tcaaaggatt   3960

acaaggatca tgacggtgac tataaagacc acgatattga ctacaaagat gacgatgaca   4020

agtaagtcga cctcgagtca tgtaattagt tatgtcacgc ttacattcac gccctccccc   4080

cacatccgct ctaaccgaaa aggaaggagt tagacaacct gaagtctagg tccctattta   4140

tttttttata gttatgttag tattaagaac gttatttata tttcaaattt ttcttttttt   4200

tctgtacaga cgcgtgtacg catgtaacat tatactgaaa accttgcttg agaaggtttt   4260

gggacgctcg aaggctttaa tttgcgtgac ataactaatt acatgacttg actgattttt   4320

cc                                                                  4322
```

```
<210> SEQ ID NO 7
<211> LENGTH: 2522
<212> TYPE: DNA
<213> ORGANISM: Artificial Sequence
<220> FEATURE:
<223> OTHER INFORMATION: Codon optimized

<400> SEQUENCE: 7

aggaaacgaa gataaatctc gagtttatca ttatcaatac tgccatttca aagaatacgt     60

aaataattaa tagtagtgat tttcctaact ttatttagtc aaaaaattag ccttttaatt    120

ctgctgtaac ccgtacatgc caaaataggg ggcgggttac acagaatata taacactgat    180

ggtgcttggg tgaacaggtt tattcctggc atccactaaa tataatggag cccgcttttt    240

aagctggcat ccagaaaaaa aaagaatccc agcaccaaaa tattgttttc ttcaccaacc    300

atcagttcat aggtccattc tcttagcgca actacagaga acagggcaca aacaggcaaa    360

aaacgggcac aacctcaatg gagtgatgca acctgcctgg agtaaatgat gacacaaggc    420

aattgaccca cgcatgtatc tatctcattt tcttacacct tctattacct tctgctctct    480

ctgatttgga aaaagctgaa aaaaaaggtt taaaccagtt ccctgaaatt attcccctac    540

ttgactaata agtatataaa gacggtaggt attgattgta attctgtaaa tctatttctt    600

aaacttctta aattctactt ttatagttag tctttttttt agttttaaaa caccaagaac    660

ttagtttcga cggatctaga actagtatga accatttgag agccgaaggt cctgcctccg    720

tattagccat aggtacagcc aacccagaaa acatattgat ccaagatgaa tttcctgatt    780

attacttcag agttaccaag agtgaacaca tgactcaatt gaaggaaaag tttagaaaaa    840

tatgtgataa gtctatgatc agaaagagaa actgcttctt gaacgaagaa catttgaagc    900

aaaatccaag attggtagaa cacgaaatgc aaacattgga tgccagacaa gacatgttag    960

ttgtcgaagt tcctaaattg ggtaaagatg cttgtgcaaa agccattaag gaatggggtc   1020

aaccaaagtc aaagatcact catttgattt ttacaagtgc atctactaca gatatgcctg   1080

gtgcagacta ccactgtgcc aaattgttag gtttgtcacc atccgttaag agagtcatga   1140

tgtatcaatt aggttgctac ggtggtggta ctgttttgag aatcgctaag gatattgcag   1200

aaaacaacaa gggtgccaga gtattagctg tttgttgcga cattatggct tgcttgttta   1260

gaggtccaag tgattctgac ttggaattgt tagttggtca agctatcttc ggtgacggtg   1320

ctgctgctgt tattgttggt gcagaacctg acgaatctgt tggtgaaaga ccaatatttg   1380

aattagtcag tacaggtcaa accatcttgc ctaattctga aggtacaatt ggtggtcata   1440

taagagaagc aggtttgatc ttcgatttgc acaaagacgt tccaatgtta atctctaaca   1500
```

```
acatagaaaa gtgtttgata gaagcattca ctcctatagg tatctcagat tggaactcta   1560

ttttctggat aacacatcca ggtggtaaag ccattttgga taaggttgaa gaaaaattgg   1620

atttgaagaa agaaaagttt gtagatagta gacatgtttt atctgaacac ggtaacatgt   1680

cttcatccac tgtcttgttc gtaatggatg aattgagaaa gagatcatta gaagagggta   1740

aatctactac tggtgacggt tttgaatggg gtgtcttatt tggtttcggt cctggtttga   1800

ccgtcgaaag agtagttgtc agatcagtac caattaaata tgaaggtaga ggttccttgt   1860

taacttgtgg tgacgttgaa gaaaacccag gtcctatggc cgtcaagcat ttgatagtat   1920

tgaagtttaa agatgaaatc acagaagctc aaaaggaaga atttttcaag acctacgtta   1980

atttggtcaa cattatacct gctatgaaag atgtatactg gggtaaagac gttacacaaa   2040

agaaagaaga aggttataca cacattgtcg aagtaacctt cgaatcagtt gaaactatcc   2100

aagattacat cattcatcca gctcacgttg gttttggtga cgtttacaga tccttctggg   2160

aaaaattgtt gatcttcgat tacaccccaa gaaagtaccc ttacgatgtt ccagactatg   2220

cataagtcga cctcgagtca tgtaattagt tatgtcacgc ttacattcac gccctccccc   2280

cacatccgct ctaaccgaaa aggaaggagt tagacaacct gaagtctagg tccctattta   2340

tttttttata gttatgttag tattaagaac gttatttata tttcaaattt ttcttttttt   2400

tctgtacaga cgcgtgtacg catgtaacat tatactgaaa accttgcttg agaaggtttt   2460

gggacgctcg aaggctttaa tttgcgtgac ataactaatt acatgacttg actgattttt   2520

cc                                                                  2522
```

<210> SEQ ID NO 8
<211> LENGTH: 3887
<212> TYPE: DNA
<213> ORGANISM: Artificial Sequence
<220> FEATURE:
<223> OTHER INFORMATION: Codon optimized

<400> SEQUENCE: 8

```
aggaaacgaa gataaatctc gagtttatca ttatcaatac tgccatttca aagaatacgt     60

aaataattaa tagtagtgat ttcctaactt ttatttagtc aaaaaattag ccttttaatt    120

ctgctgtaac ccgtacatgc caaaataggg ggcgggttac acagaatata taacactgat    180

ggtgcttggg tgaacaggtt tattcctggc atccactaaa tataatggag cccgcttttt    240

aagctggcat ccagaaaaaa aaagaatccc agcaccaaaa tattgttttc ttcaccaacc    300

atcagttcat aggtccattc tcttagcgca actacagaga acagggcaca aacaggcaaa    360

aaacgggcac aacctcaatg gagtgatgca acctgcctgg agtaaatgat gacacaaggc    420

aattgaccca cgcatgtatc tatctcattt tcttacacct tctattacct tctgctctct    480

ctgatttgga aaaagctgaa aaaaaaggtt taaaccagtt ccctgaaatt attcccctac    540

ttgactaata agtatataaa gacggtaggt attgattgta attctgtaaa tctatttctt    600

aaacttctta aattctactt ttatagttag tctttttttt agttttaaaa caccaagaac    660

ttagtttcga cggatctaga actagtatgg gtttatcatc cgtctgtact ttctccttcc    720

aaactaacta tcatacctta ttgaatcctc acaacaacaa tccaaaaaca tcattgttgt    780

gttacagaca tccaaagaca cctattaagt actcttacaa caactttcca tcaaaacatt    840

gttcaaccaa gtccttccac ttacaaaata agtgctccga aagtttgtct atagctaaga    900

actctatcag agctgcaact acaaatcaaa ctgaaccacc tgaaagtgat aatcactctg    960
```

-continued

```
ttgccacaaa aattttgaac ttcggtaaag catgttggaa gttgcaaaga ccatacacca   1020

taatcgcttt tacttcttgt gcatgcggtt tattcggtaa agaattgttg cataacacta   1080

acttaatttc atggtccttg atgttcaagg catttttctt tttagttgcc atcttgtgca   1140

tcgcttcatt caccactaca attaatcaaa tatacgattt gcacatcgac agaattaaca   1200

aaccagattt gcctttggct tcaggtgaaa tatccgtcaa tactgcatgg atcatgtcta   1260

tcatagtagc cttgttcggt ttgatcatca caattaaaat gaagggtggt ccattgtaca   1320

tcttcggtta ctgtttcggt atcttcggtg gtattgtcta ttccgtacca ccttttagat   1380

ggaaacaaaa ccctagtact gcctttttgt tgaatttctt agctcatatc atcacaaact   1440

tcaccttcta ctacgcttca agagctgctt taggtttgcc attcgaattg agaccttcat   1500

tcacattttt gttggcattc atgaaaagta tgggttctgc attagccttg atcaaggatg   1560

cctctgacgt tgaaggtgac acaaagttcg gtattagtac cttggcttct aagtacggtt   1620

caagaaattt gactttgttc tgctccggta tcgttttgtt aagttacgtc gcagccattt   1680

tggcaggtat catttggcca caagccttta attctaacgt tatgttgttg tcacatgcca   1740

tcttggcttt ctggttgatc ttgcaaacta gagatttcgc tttgacaaat tatgaccctg   1800

aagcaggtag aagattctac gagtttatgt ggaaattgta ctacgctgaa tatttggtat   1860

acgtttttat tgaaggtaga ggttctttgt tgacctgtgg tgacgttgaa gaaaatccag   1920

gtcctatgaa atgttcaact ttctcctttt ggttcgtatg caagatcatc ttcttttttct   1980

tttcctttaa catccaaaca agtatcgcaa acccaagaga aaactttttg aagtgcttct   2040

cacaatacat acctaataac gccaccaatt tgaagttggt ttacactcaa aacaacccat   2100

tgtacatgtc cgtcttgaac agtacaatcc ataatttgag attcacttct gataccactc   2160

caaaaccttt ggtcattgta acccctagtc atgtatctca catccaaggt actatcttat   2220

gttctaaaaa ggttggtttg caaattagaa ctagatccgg tggtcatgat agtgaaggca   2280

tgtcatacat ctcccaagtt ccattcgtta tcgttgattt gagaaacatg agatcaatta   2340

aaatagacgt acactcacaa actgcttggg ttgaagctgg tgcaacattg ggtgaagtat   2400

actactgggt taacgaaaag aatgaaaact tatcattggc tgctggttac tgtccaacag   2460

tttgcgcagg tggtcatttt ggtggtggtg gttatggtcc tttaatgaga aactacggtt   2520

tggccgctga taacataatc gacgctcatt tggtaaatgt tcacggtaaa gttttggata   2580

gaaagtctat gggtgaagac ttattttggg ctttgagagg tggtggtgca gaatcattcg   2640

gtatcatagt tgcttggaag ataagattag tcgcagtacc aaagtctact atgttctcag   2700

tcaaaaagat aatggaaatc catgaattag ttaaattggt caataagtgg caaaacatcg   2760

catacaagta cgataaggac ttgttgttga tgactcattt catcacaaga aacatcaccg   2820

ataaccaagg taaaaataag actgctatcc acacatactt ttcttcagtt ttcttgggtg   2880

gtgtcgattc cttagtagac ttgatgaata agtcttttcc agaattaggt attaagaaaa   2940

ctgattgtag acaattgtct tggatcgaca ccatcatctt ttattcaggt gttgtcaact   3000

acgatacaga caacttcaac aaagaaatat tattggatag atccgcaggt caaaacggtg   3060

cctttaaaat taagttagac tacgttaaaa agccaatacc tgaatcagtt ttcgtccaaa   3120

tcttagaaaa attgtacgaa gaagatattg gtgcaggcat gtacgccttg tatccatacg   3180

gtggtataat ggacgaaatc agtgaatctg ccattccatt tcctcataga gctggtatct   3240

tatacgaatt gtggtacatt tgttcatggg aaaagcaaga agataacgaa aagcacttaa   3300

actggattag aaacatctat aacttcatga ctccatacgt ttctaaaaac cctagattgg   3360
```

catatttgaa ctacagagat ttggacatcg gtattaacga tccaaagaat cctaacaact 3420
atacccaagc tagaatttgg ggtgaaaaat acttcggtaa aaatttcgat agattagtaa 3480
aggttaagac attggttgac ccaaacaact tctttagaaa cgaacaatcc attccacctt 3540
tacctagaca tagacacgaa caaaaattaa taagtgaaga agatttgtaa gtcgacctcg 3600
agtcatgtaa ttagttatgt cacgcttaca ttcacgccct ccccccacat ccgctctaac 3660
cgaaaaggaa ggagttagac aacctgaagt ctaggtccct atttattttt ttatagttat 3720
gttagtatta agaacgttat ttatatttca aatttttctt ttttttctgt acagacgcgt 3780
gtacgcatgt aacattatac tgaaaacctt gcttgagaag gttttgggac gctcgaaggc 3840
tttaatttgc gtgacataac taattacatg acttgactga tttttcc 3887

<210> SEQ ID NO 9
<211> LENGTH: 8963
<212> TYPE: DNA
<213> ORGANISM: Artificial Sequence
<220> FEATURE:
<223> OTHER INFORMATION: Codon optimized

<400> SEQUENCE: 9
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300
aaatagcttg tcaccttacg tacaatcttg atccggagct tttctttttt tgccgattaa 360
gaattaattc ggtcgaaaaa agaaaaggag agggccaaga gggagggcat tggtgactat 420
tgagcacgtg agtatacgtg attaagcaca caaaggcagc ttggagtatg tctgttatta 480
atttcacagg tagttctggt ccattggtga aagtttgcgg cttgcagagc acagaggccg 540
cagaatgtgc tctagattcc gatgctgact tgctgggtat tatatgtgtg cccaatagaa 600
agagaacaat tgacccggtt attgcaagga aaatttcaag tcttgtaaaa gcatataaaa 660
atagttcagg cactccgaaa tacttggttg gcgtgtttcg taatcaacct aaggaggatg 720
ttttggctct ggtcaatgat tacggcattg atatcgtcca actgcatgga gatgagtcgt 780
ggcaagaata ccaagagttc ctcggtttgc cagttattaa aagactcgta tttccaaaag 840
actgcaacat actactcagt gcagcttcac agaaacctca ttcgtttatt cccttgtttg 900
attcagaagc aggtgggaca ggtgaacttt tggattggaa ctcgatttct gactgggttg 960
gaaggcaaga gagccccgaa agcttacatt ttatgttagc tggtggactg acgccagaaa 1020
atgttggtga tgcgcttaga ttaaatggcg ttattggtgt tgatgtaagc ggaggtgtgg 1080
agacaaatgg tgtaaaagac tctaacaaaa tagcaaattt cgtcaaaaat gctaagaaat 1140
aggttattac tgagtagtat ttatttaagt attgtttgtg cacttgccta tgcggtgtga 1200
aataccgcac agatgcgtaa ggagaaaata ccgcatcagg aaattgtaaa cgttaatatt 1260
ttgttaaaat tcgcgttaaa tttttgttaa atcagctcat tttttaacca ataggccgaa 1320
atcggcaaaa tcccttataa atcaaaagaa tagaccgaga tagggttgag tgttgttcca 1380
gtttggaaca agagtccact attaaagaac gtggactcca acgtcaaagg gcgaaaaacc 1440
gtctatcagg gcgatggccc actacgtgaa ccatcaccct aatcaagttt tttggggtcg 1500

```
aggtgccgta aagcactaaa tcggaaccct aaagggagcc cccgatttag agcttgacgg   1560

ggaaagccgg cgaacgtggc gagaaaggaa gggaagaaag cgaaaggagc gggcgctagg   1620

gcgctggcaa gtgtagcggt cacgctgcgc gtaaccacca cacccgccgc gcttaatgcg   1680

ccgctacagg gcgcgtcgcg ccattcgcca ttcaggctgc gcaactgttg ggaagggcga   1740

tcggtgcggg cctcttcgct attacgccag ctggcgaaag ggggatgtgc tgcaaggcga   1800

ttaagttggg taacgccagg gttttcccag tcacgacgtt gtaaaacgac ggccagtgag   1860

cgcgcgtaat acgactcact atagggcgaa ttgggtaccg gccgcaaatt aaagccttcg   1920

agcgtcccaa aaccttctca agcaaggttt tcagtataat gttacatgcg tacacgcgtc   1980

tgtacagaaa aaaaagaaaa atttgaaata taaataacgt tcttaatact aacataacta   2040

taaaaaaata aatagggacc tagacttcag gttgtctaac tccttccttt tcggttagag   2100

cggatgtggg gggagggcgt gaatgtaagc gtgacataac taattacatg actcgaggtc   2160

gacttacttg tcatcgtcat ctttgtagtc aatatcgtgg tctttatagt caccgtcatg   2220

atccttgtaa tcctttgatc tcttgtagac cttattcaag aaagctgtca aaacgtcggc   2280

tttaaaacct cttgattcat caacttgact aatctttgcc tttaagtctt tagcgatgga   2340

ttcttcgtat tcatggtaca attgttcaat cttcaaatca ttaaaaattt tcttacactt   2400

tgcttcagca actgagtcct ttttaccgta gttttcatcc aaagtctttc tttgttcggc   2460

agatgctaat tccaaagcct tgttaataac ccaactgcac ttattgtctt gaatatctgt   2520

accgatttta cctatttgtt ctggagtacc gaaacagtct aagtagtcat cttggatttg   2580

gaagtattca cccaaaggta tcaaaacatc tcttgcttgc ttcaagtctt tttcatcagt   2640

aataccagct acgtacatag ccaaggcgac tggcaaatag aaggagtaat aagcagtttc   2700

aaaggtgacg atgaatgaat gtttcttcaa ggaaaacttt gacaagtcaa ctttatcttc   2760

aggtgcagtt atcaaatcca tcaattgacc caattctgtt tggaaagtaa cttcgtggaa   2820

taattcggta atatcgatgt agtacttttc gtttctgaaa tgtgacttca acaatttata   2880

gatagcggct tccaacataa aagcatcatt tatggctatt tcaccaactt ctggaacttt   2940

gtaccagcat ggttgacctc ttcttgttat agacttatcc atcatgtcat cggcaaccaa   3000

aaagtatgct tgcaacaatt caatacacca acccaagata gcgacctttt cgtattcttc   3060

ttgacctaat tgttcaacgg ttttgttaga caagatagca taagtatcaa ctacactcaa   3120

acctctattc aatttaccac ctggagtatt gtagtttaaa gagtgagcat accaatcgca   3180

ggcttcttta ggcataccat aagctaacaa actagcgttc aattcttcaa ctaactttgg   3240

gaatacgttc aagaatcttt ctcttcttat ttccttttct gaagccatag gacctggatt   3300

ttcttcaacg tcaccacatg ttaacaaaga acctctacct tcttcgaaat gactgaattg   3360

ttgtctcaaa actcttctca tgatcttgtt tgttgcagtt ctaggtaagg atgacaatgg   3420

gacaactcta gtaactttga ataatgggtt caatttcttt tgcaaaccca agttaaagga   3480

taatctcaat tggttcaaat caatggttgt gtcgtttgaa tccttcaata cgaaaaatat   3540

gaccaattgt tctggaccac cacccaaagg tggaacacca atagcagtgg tttcaaaaac   3600

tctgtcatct acttcattac agactctttc gatttcgata gaactaattt tgataccacc   3660

gatgttcata gtgtcatcgg ctctaccgtg tgcatggtag taaccgttag aggtcaattc   3720

gaaaatgtca ccatgtcttc tcaatacttc accattcaag gttggcatac ccttgaaata   3780

gacatcgtga tgattaccgt ttaacaatgt ttttgaggca ccaaacataa caggacctaa   3840

tgccaattca ccgatacctg gcttattttt aggcattggg taaccgttct tatctaatat   3900
```

```
gtacaaggtg caacccatac attgggatga aaaagaactt aaagattgag cttgcaaaaa   3960
tgaaccagca gaaaaagcac caccgatttc tgtaccacca cacatttcta taactggctt   4020
gtagttagct ctacccatta accacaaata ttcgtctaca ttagaggctt caccggatga   4080
agaaaagcat cttatggtgg accaatcgta acctgaaaca caatttgtgg atttccatga   4140
tcttacaata gatggtacga cacccaacat tgtgaccttt gcatcttgaa caaatttagc   4200
gaaaccagag actaaaggac taccgttgta caaggcaata gatgcaccat ttaacaaact   4260
agcataaacc aaccaaggac ccatcatcca acccaaatta gttggccata ctataacgtc   4320
accttttcta atatccaaat gagaccaacc atcagcagca gccttcaatg gggtggcttg   4380
tgtccaagga attgcttttg gttcacctgt agtaccactg gagaataaga tgttagtata   4440
agcatcaaca ggttgttctc tggcagtaaa ctcgcagttt ttaaactcct tggctctttc   4500
taaaaagtaa tcccaagata tgtcaccatc tctcaattct gcaccaatgt tagaaccact   4560
acaagggata actattgcca ttggggattt agcttcaact actcttgaat acaatggtat   4620
tctcttttta cctctgatga tgtgatcttg tgtgaaaatt gccttagctt tggataatct   4680
caatctagtt gagatttcag gggcggaaaa tgaatctgct atagagacaa ctacgtaacc   4740
agccaatact atggccaaat atataacaac agcatcaaca tgcattggca tatcgatggc   4800
tattgcacaa ccttttteta aacccatttc ttccaatgca taaccaacca accaaactct   4860
ctttctcaat tgatctaatg tcaacttatt caaaggcaag tcatcgttac cctcgtctct   4920
ccaaacgatc atagtatcgt tcaatttctt attggagttt acgttcaagc aatttttagc   4980
tgagttcaag taaccaccag gtaaccattc agaaccacct gggttgttga tgtcatctct   5040
tctcaagata cattctgggt ccttagagaa actaattttc atttcatcca tcaatactgt   5100
tctccaatag acttcagggt ttctaacaga aaattcttgg aagtgagaaa aagaagaaat   5160
tggatctttg tactttacac ccaaaaattc tttacctctc ttttccaaca aagcacccaa   5220
attagttgac ttgacttttt cagggtctgg aatccaagca ggtggggctg gaccgaaatc   5280
cttgtagcaa ccataaaaca acatttggtg taaggagaaa ggcaaatctg gtgacaagat   5340
atggttagcg atgttgatcc aagtttgagg ggttgcagca ccataattac aaacgatttc   5400
tgccaatcta ccatgtaatg tttctgctac ttctgaggtg atacccaatg cgatgaaatc   5460
tgaggcaacg actgaatcca aggacttata gtttttaccc atactagttc tagatccgtc   5520
gaaactaagt tcttggtgtt ttaaaactaa aaaaaagact aactataaaa gtagaattta   5580
agaagtttaa gaaatagatt tacagaatta caatcaatac ctaccgtctt tatatactta   5640
ttagtcaagt aggggaataa tttcagggaa ctggtttaaa cctttttttt cagctttttc   5700
caaatcagag agagcagaag gtaatagaag gtgtaagaaa atgagataga tacatgcgtg   5760
ggtcaattgc cttgtgtcat catttactcc aggcaggttg catcactcca ttgaggttgt   5820
gcccgttttt tgcctgtttg tgccctgttc tctgtagttg cgctaagaga atggacctat   5880
gaactgatgg ttggtgaaga aaacaatatt ttggtgctgg gattcttttt ttttctggat   5940
gccagcttaa aaagcgggct ccattatatt tagtggatgc caggaataaa cctgttcacc   6000
caagcaccat cagtgttata tattctgtgt aacccgcccc ctattttggc atgtacgggt   6060
tacagcagaa ttaaaaggct aatttttga ctaaataaag ttaggaaaat cactactatt   6120
aattatttac gtattctttg aaatggcagt attgataatg ataaactcga gagctccagc   6180
ttttgttccc tttagtgagg gttaattgcg cgcttggcgt aatcatggtc atagctgttt   6240
```

-continued

```
cctgtgtgaa attgttatcc gctcacaatt ccacacaaca taggagccgg aagcataaag   6300
tgtaaagcct ggggtgccta atgagtgagg taactcacat taattgcgtt gcgctcactg   6360
cccgctttcc agtcgggaaa cctgtcgtgc cagctgcatt aatgaatcgg ccaacgcgcg   6420
gggagaggcg gtttgcgtat tgggcgctct tccgcttcct cgctcactga ctcgctgcgc   6480
tcggtcgttc ggctgcggcg agcggtatca gctcactcaa aggcggtaat acggttatcc   6540
acagaatcag gggataacgc aggaaagaac atgtgagcaa aaggccagca aaaggccagg   6600
aaccgtaaaa aggccgcgtt gctggcgttt ttccataggc tccgcccccc tgacgagcat   6660
cacaaaaatc gacgctcaag tcagaggtgg cgaaacccga caggactata aagataccag   6720
gcgtttcccc ctggaagctc cctcgtgcgc tctcctgttc cgaccctgcc gcttaccgga   6780
tacctgtccg cctttctccc ttcgggaagc gtggcgcttt ctcatagctc acgctgtagg   6840
tatctcagtt cggtgtaggt cgttcgctcc aagctgggct gtgtgcacga accccccgtt   6900
cagcccgacc gctgcgcctt atccggtaac tatcgtcttg agtccaaccc ggtaagacac   6960
gacttatcgc cactggcagc agccactggt aacaggatta gcagagcgag gtatgtaggc   7020
ggtgctacag agttcttgaa gtggtggcct aactacggct acactagaag gacagtattt   7080
ggtatctgcg ctctgctgaa gccagttacc ttcggaaaaa gagttggtag ctcttgatcc   7140
ggcaaacaaa ccaccgctgg tagcggtggt ttttttgttt gcaagcagca gattacgcgc   7200
agaaaaaaag gatctcaaga agatcctttg atcttttcta cggggtctga cgctcagtgg   7260
aacgaaaact cacgttaagg gattttggtc atgagattat caaaaaggat cttcacctag   7320
atccttttaa attaaaaatg aagttttaaa tcaatctaaa gtatatatga gtaaacttgg   7380
tctgacagtt accaatgctt aatcagtgag gcacctatct cagcgatctg tctatttcgt   7440
tcatccatag ttgcctgact ccccgtcgtg tagataacta cgatacggga gggcttacca   7500
tctggcccca gtgctgcaat gataccgcga gacccacgct caccggctcc agatttatca   7560
gcaataaacc agccagccgg aagggccgag cgcagaagtg gtcctgcaac tttatccgcc   7620
tccatccagt ctattaattg ttgccgggaa gctagagtaa gtagttcgcc agttaatagt   7680
ttgcgcaacg ttgttgccat tgctacaggc atcgtggtgt cacgctcgtc gtttggtatg   7740
gcttcattca gctccggttc ccaacgatca aggcgagtta catgatcccc catgttgtgc   7800
aaaaaagcgg ttagctcctt cggtcctccg atcgttgtca gaagtaagtt ggccgcagtg   7860
ttatcactca tggttatggc agcactgcat aattctctta ctgtcatgcc atccgtaaga   7920
tgcttttctg tgactggtga gtactcaacc aagtcattct gagaatagtg tatgcggcga   7980
ccgagttgct cttgcccggc gtcaatacgg gataataccg cgccacatag cagaacttta   8040
aaagtgctca tcattggaaa acgttcttcg gggcgaaaac tctcaaggat cttaccgctg   8100
ttgagatcca gttcgatgta acccactcgt gcacccaact gatcttcagc atcttttact   8160
ttcaccagcg tttctgggtg agcaaaaaca ggaaggcaaa atgccgcaaa aaagggaata   8220
agggcgacac ggaaatgttg aatactcata ctcttccttt ttcaatatta ttgaagcatt   8280
tatcagggtt attgtctcat gagcggatac atatttgaat gtatttagaa aaataaacaa   8340
ataggggttc cgcgcacatt tccccgaaaa gtgccacctg ggtccttttc atcacgtgct   8400
ataaaaataa ttataattta aattttttaa tataaatata taaattaaaa atagaaagta   8460
aaaaaagaaa ttaaagaaaa aatagttttt gttttccgaa gatgtaaaag actctagggg   8520
gatcgccaac aaatactacc ttttatcttg ctcttcctgc tctcaggtat taatgccgaa   8580
ttgtttcatc ttgtctgtgt agaagaccac acacgaaaat cctgtgattt tacattttac   8640
```

```
ttatcgttaa tcgaatgtat atctatttaa tctgcttttc ttgtctaata aatatatatg   8700

taaagtacgc tttttgttga aattttttaa acctttgttt attttttttt cttcattccg   8760

taactcttct accttcttta tttactttct aaaatccaaa tacaaaacat aaaaataaat   8820

aaacacagag taaattccca aattattcca tcattaaaag atacgaggcg cgtgtaagtt   8880

acaggcaagc gatccgtcct aagaaaccat tattatcatg acattaacct ataaaaatag   8940

gcgtatcacg aggccctttc gtc                                           8963
```

<210> SEQ ID NO 10
<211> LENGTH: 7163
<212> TYPE: DNA
<213> ORGANISM: Artificial Sequence
<220> FEATURE:
<223> OTHER INFORMATION: Codon optimized

<400> SEQUENCE: 10

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct ttctttttt tgccgattaa    360

gaattaattc ggtcgaaaaa agaaaaggag agggccaaga gggagggcat tggtgactat    420

tgagcacgtg agtatacgtg attaagcaca caaaggcagc ttggagtatg tctgttatta    480

atttcacagg tagttctggt ccattggtga aagtttgcgg cttgcagagc acagaggccg    540

cagaatgtgc tctagattcc gatgctgact tgctgggtat tatatgtgtg cccaatagaa    600

agagaacaat tgacccggtt attgcaagga aaatttcaag tcttgtaaaa gcatataaaa    660

atagttcagg cactccgaaa tacttggttg gcgtgtttcg taatcaacct aaggaggatg    720

ttttggctct ggtcaatgat tacggcattg atatcgtcca actgcatgga gatgagtcgt    780

ggcaagaata ccaagagttc ctcggtttgc cagttattaa aagactcgta tttccaaaag    840

actgcaacat actactcagt gcagcttcac agaaacctca ttcgtttatt cccttgtttg    900

attcagaagc aggtgggaca ggtgaacttt tggattggaa ctcgatttct gactgggttg    960

gaaggcaaga gagccccgaa agcttacatt ttatgttagc tggtggactg acgccagaaa   1020

atgttggtga tgcgcttaga ttaaatggcg ttattggtgt tgatgtaagc ggaggtgtgg   1080

agacaaatgg tgtaaaagac tctaacaaaa tagcaaattt cgtcaaaaat gctaagaaat   1140

aggttattac tgagtagtat ttatttaagt attgtttgtg cacttgccta tgcggtgtga   1200

aataccgcac agatgcgtaa ggagaaaata ccgcatcagg aaattgtaaa cgttaatatt   1260

ttgttaaaat tcgcgttaaa tttttgttaa atcagctcat tttttaacca ataggccgaa   1320

atcggcaaaa tcccttataa atcaaaagaa tagaccgaga tagggttgag tgttgttcca   1380

gtttggaaca agagtccact attaaagaac gtggactcca acgtcaaagg gcgaaaaacc   1440

gtctatcagg gcgatggccc actacgtgaa ccatcaccct aatcaagttt tttggggtcg   1500

aggtgccgta aagcactaaa tcggaaccct aaagggagcc cccgatttag agcttgacgg   1560

ggaaagccgg cgaacgtggc gagaaaggaa gggaagaaag cgaaaggagc gggcgctagg   1620

gcgctggcaa gtgtagcggt cacgctgcgc gtaaccacca cacccgccgc gcttaatgcg   1680
```

```
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttatgca tagtctggaa catcgtaagg gtactttctt ggggtgtaat cgaagatcaa   2220
caatttttcc cagaaggatc tgtaaacgtc accaaaacca acgtgagctg gatgaatgat   2280
gtaatcttgg atagtttcaa ctgattcgaa ggttacttcg acaatgtgtg tataaccttc   2340
ttctttcttt tgtgtaacgt ctttacccca gtatacatct ttcatagcag gtataatgtt   2400
gaccaaatta acgtaggtct tgaaaaattc ttcctttttga gcttctgtga tttcatcttt   2460
aaacttcaat actatcaaat gcttgacggc cataggacct gggttttctt caacgtcacc   2520
acaagttaac aaggaacctc taccttcata tttaattggt actgatctga caactactct   2580
ttcgacggtc aaaccaggac cgaaaccaaa taagacaccc cattcaaaac cgtcaccagt   2640
agtagattta ccctcttcta atgatctctt tctcaattca tccattacga acaagacagt   2700
ggatgaagac atgttaccgt gttcagataa aacatgtcta ctatctacaa acttttcttt   2760
cttcaaatcc aatttttctt caaccttatc caaaatggct ttaccacctg gatgtgttat   2820
ccagaaaata gagttccaat ctgagatacc tataggagtg aatgcttcta tcaaacactt   2880
ttctatgttg ttagagatta acattggaac gtctttgtgc aaatcgaaga tcaaacctgc   2940
ttctcttata tgaccaccaa ttgtaccttc agaattaggc aagatggttt gacctgtact   3000
gactaattca aatattggtc tttcaccaac agattcgtca ggttctgcac caacaataac   3060
agcagcagca ccgtcaccga agatagcttg accaactaac aattccaagt cagaatcact   3120
tggacctcta aacaagcaag ccataatgtc gcaacaaaca gctaatactc tggcaccctt   3180
gttgttttct gcaatatcct tagcgattct caaaacagta ccaccaccgt agcaacctaa   3240
ttgatacatc atgactctct taacggatgg tgacaaacct aacaatttgg cacagtggta   3300
gtctgcacca ggcatatctg tagtagatgc acttgtaaaa atcaaatgag tgatctttga   3360
ctttggttga ccccattcct taatggcttt tgcacaagca tctttaccca atttaggaac   3420
ttcgacaact aacatgtctt gtctggcatc caatgtttgc atttcgtgtt ctaccaatct   3480
tggattttgc ttcaaatgtt cttcgttcaa gaagcagttt ctctttctga tcatagactt   3540
atcacatatt tttctaaact tttccttcaa ttgagtcatg tgttcactct tggtaactct   3600
gaagtaataa tcaggaaatt catcttggat caatatgttt tctgggttgg ctgtacctat   3660
ggctaatacg gaggcaggac cttcggctct caaatggttc atactagttc tagatccgtc   3720
gaaactaagt tcttggtgtt ttaaaactaa aaaaaagact aactataaaa gtagaattta   3780
agaagtttaa gaaatagatt tacagaatta caatcaatac ctaccgtctt tatatactta   3840
ttagtcaagt aggggaataa tttcagggaa ctggtttaaa cctttttttt cagctttttc   3900
caaatcagag agagcagaag gtaatagaag gtgtaagaaa atgagataga tacatgcgtg   3960
ggtcaattgc cttgtgtcat catttactcc aggcaggttg catcactcca ttgaggttgt   4020
gcccgttttt tgcctgtttg tgccctgttc tctgtagttg cgctaagaga atggacctat   4080
```

```
gaactgatgg ttggtgaaga aaacaatatt ttggtgctgg gattcttttt ttttctggat   4140

gccagcttaa aaagcgggct ccattatatt tagtggatgc caggaataaa cctgttcacc   4200

caagcaccat cagtgttata tattctgtgt aacccgcccc ctattttggc atgtacgggt   4260

tacagcagaa ttaaaaggct aatttttga ctaaataaag ttaggaaaat cactactatt   4320

aattatttac gtattctttg aaatggcagt attgataatg ataaactcga gagctccagc   4380

ttttgttccc tttagtgagg gttaattgcg cgcttggcgt aatcatggtc atagctgttt   4440

cctgtgtgaa attgttatcc gctcacaatt ccacacaaca taggagccgg aagcataaag   4500

tgtaaagcct ggggtgccta atgagtgagg taactcacat taattgcgtt gcgctcactg   4560

cccgctttcc agtcgggaaa cctgtcgtgc cagctgcatt aatgaatcgg ccaacgcgcg   4620

gggagaggcg gtttgcgtat tgggcgctct tccgcttcct cgctcactga ctcgctgcgc   4680

tcggtcgttc ggctgcggcg agcggtatca gctcactcaa aggcggtaat acggttatcc   4740

acagaatcag gggataacgc aggaaagaac atgtgagcaa aaggccagca aaaggccagg   4800

aaccgtaaaa aggccgcgtt gctggcgttt ttccataggc tccgcccccc tgacgagcat   4860

cacaaaaatc gacgctcaag tcagaggtgg cgaaacccga caggactata aagataccag   4920

gcgtttcccc ctggaagctc cctcgtgcgc tctcctgttc cgaccctgcc gcttaccgga   4980

tacctgtccg cctttctccc ttcgggaagc gtggcgcttt ctcatagctc acgctgtagg   5040

tatctcagtt cggtgtaggt cgttcgctcc aagctgggct gtgtgcacga accccccgtt   5100

cagcccgacc gctgcgcctt atccggtaac tatcgtcttg agtccaaccc ggtaagacac   5160

gacttatcgc cactggcagc agccactggt aacaggatta gcagagcgag gtatgtaggc   5220

ggtgctacag agttcttgaa gtggtggcct aactacggct acactagaag gacagtattt   5280

ggtatctgcg ctctgctgaa gccagttacc ttcggaaaaa gagttggtag ctcttgatcc   5340

ggcaaacaaa ccaccgctgg tagcggtggt ttttttgttt gcaagcagca gattacgcgc   5400

agaaaaaaag gatctcaaga agatcctttg atcttttcta cggggtctga cgctcagtgg   5460

aacgaaaact cacgttaagg gattttggtc atgagattat caaaaaggat cttcacctag   5520

atccttttaa attaaaaatg aagttttaaa tcaatctaaa gtatatatga gtaaacttgg   5580

tctgacagtt accaatgctt aatcagtgag gcacctatct cagcgatctg tctatttcgt   5640

tcatccatag ttgcctgact ccccgtcgtg tagataacta cgatacggga gggcttacca   5700

tctggcccca gtgctgcaat gataccgcga gacccacgct caccggctcc agatttatca   5760

gcaataaacc agccagccgg aagggccgag cgcagaagtg gtcctgcaac tttatccgcc   5820

tccatccagt ctattaattg ttgccgggaa gctagagtaa gtagttcgcc agttaatagt   5880

ttgcgcaacg ttgttgccat tgctacaggc atcgtggtgt cacgctcgtc gtttggtatg   5940

gcttcattca gctccggttc ccaacgatca aggcgagtta catgatcccc catgttgtgc   6000

aaaaaagcgg ttagctcctt cggtcctccg atcgttgtca gaagtaagtt ggccgcagtg   6060

ttatcactca tggttatggc agcactgcat aattctctta ctgtcatgcc atccgtaaga   6120

tgcttttctg tgactggtga gtactcaacc aagtcattct gagaatagtg tatgcggcga   6180

ccgagttgct cttgcccggc gtcaatacgg gataataccg cgccacatag cagaacttta   6240

aaagtgctca tcattggaaa acgttcttcg gggcgaaaac tctcaaggat cttaccgctg   6300

ttgagatcca gttcgatgta acccactcgt gcacccaact gatcttcagc atcttttact   6360

ttcaccagcg tttctgggtg agcaaaaaca ggaaggcaaa atgccgcaaa aaagggaata   6420
```

agggcgacac ggaaatgttg aatactcata ctcttccttt ttcaatatta ttgaagcatt 6480
tatcagggtt attgtctcat gagcggatac atatttgaat gtatttagaa aaataaacaa 6540
ataggggttc cgcgcacatt tccccgaaaa gtgccacctg ggtccttttc atcacgtgct 6600
ataaaaataa ttataattta aattttttaa tataaatata taaattaaaa atagaaagta 6660
aaaaaagaaa ttaaagaaaa aatagttttt gttttccgaa gatgtaaaag actctagggg 6720
gatcgccaac aaatactacc ttttatcttg ctcttcctgc tctcaggtat taatgccgaa 6780
ttgtttcatc ttgtctgtgt agaagaccac acacgaaaat cctgtgattt tacattttac 6840
ttatcgttaa tcgaatgtat atctatttaa tctgcttttc ttgtctaata aatatatatg 6900
taaagtacgc tttttgttga aattttttaa acctttgttt attttttttt cttcattccg 6960
taactcttct accttcttta tttactttct aaaatccaaa tacaaaacat aaaaataaat 7020
aaacacagag taaattccca aattattcca tcattaaaag atacgaggcg cgtgtaagtt 7080
acaggcaagc gatccgtcct aagaaaccat tattatcatg acattaacct ataaaaatag 7140
gcgtatcacg aggccctttc gtc 7163

<210> SEQ ID NO 11
<211> LENGTH: 8710
<212> TYPE: DNA
<213> ORGANISM: Artificial Sequence
<220> FEATURE:
<223> OTHER INFORMATION: Codon optimized

<400> SEQUENCE: 11
tcgcgcgttt cggtgatgac ggtgaaaacc tctgacacat gcagctcccg gagacggtca 60
cagcttgtct gtaagcggat gccgggagca gacaagcccg tcagggcgcg tcagcgcgtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat atttttttat gcctcggtaa tgattttcat 360
tttttttttt cccctagcgg atgactcttt ttttttctta gcgattggca ttatcacata 420
atgaattata cattatataa agtaatgtga tttcttcgaa gaatatacta aaaaatgagc 480
aggcaagata aacgaaggca aagatgacag agcagaaagc cctagtaaag cgtattacaa 540
atgaaaccaa gattcagatt gcgatctctt taaagggtgg tcccctagcg atagagcact 600
cgatcttccc agaaaaagag gcagaagcag tagcagaaca ggccacacaa tcgcaagtga 660
ttaacgtcca cacaggtata gggtttctgg accatatgat acatgctctg gccaagcatt 720
ccggctggtc gctaatcgtt gagtgcattg gtgacttaca catagacgac catcacacca 780
ctgaagactg cgggattgct ctcggtcaag cttttaaaga ggccctactg gcgcgtggag 840
taaaaaggtt tggatcagga tttgcgcctt tggatgaggc actttccaga gcggtggtag 900
atctttcgaa caggccgtac gcagttgtcg aacttggttt gcaaagggag aaagtaggag 960
atctctcttg cgagatgatc ccgcattttc ttgaaagctt tgcagaggct agcagaatta 1020
ccctccacgt tgattgtctg cgaggcaaga atgatcatca ccgtagtgag agtgcgttca 1080
aggctcttgc ggttgccata agagaagcca cctcgcccaa tggtaccaac gatgttccct 1140
ccaccaaagg tgttcttatg tagtgacacc gattatttaa agctgcagca tacgatatat 1200
atacatgtgt atatatgtat acctatgaat gtcagtaagt atgtatacga acagtatgat 1260
actgaagatg acaaggtaat gcatcattct atacgtgtca ttctgaacga ggcgcgcttt 1320

-continued cctttttctt ttttgctttt tcttttttttt tctcttgaac tcgacggatc tatgcggtgt 1380
gaaataccgc acagatgcgt aaggagaaaa taccgcatca ggaaattgta aacgttaata 1440
ttttgttaaa attcgcgtta aatttttgtt aaatcagctc atttttttaac caataggccg 1500 aaatcggcaa aatcccttat aaatcaaaag aatagaccga gatagggttg agtgttgttc 1560
cagtttggaa caagagtcca ctattaaaga acgtggactc caacgtcaaa gggcgaaaaa 1620
ccgtctatca gggcgatggc ccactacgtg aaccatcacc ctaatcaagt tttttggggt 1680
cgaggtgccg taaagcacta aatcggaacc ctaaagggag cccccgattt agagcttgac 1740
ggggaaagcc ggcgaacgtg gcgagaaagg aagggaagaa agcgaaagga gcgggcgcta 1800
gggcgctggc aagtgtagcg gtcacgctgc gcgtaaccac cacacccgcc gcgcttaatg 1860
cgccgctaca gggcgcgtcg cgccattcgc cattcaggct gcgcaactgt tgggaagggc 1920
gatcggtgcg ggcctcttcg ctattacgcc agctggcgaa agggggatgt gctgcaaggc 1980
gattaagttg ggtaacgcca gggttttccc agtcacgacg ttgtaaaacg acggccagtg 2040
agcgcgcgta atacgactca ctatagggcg aattgggtac cggccgcaaa ttaaagcctt 2100
cgagcgtccc aaaaccttct caagcaaggt tttcagtata atgttacatg cgtacacgcg 2160
tctgtacaga aaaaaaagaa aaatttgaaa tataaataac gttcttaata ctaacataac 2220
tataaaaaaa taaataggga cctagacttc aggttgtcta actccttcct tttcggttag 2280
agcggatgtg gggggagggc gtgaatgtaa gcgtgacata actaattaca tgactcgagg 2340
tcgacttaca aatcttcttc acttattaat ttttgttcgt gtctatgtct aggtaaaggt 2400
ggaatggatt gttcgtttct aaagaagttg tttgggtcaa ccaatgtctt aacctttact 2460
aatctatcga aatttttacc gaagtatttt tcaccccaaa ttctagcttg ggtatagttg 2520
ttaggattct ttggatcgtt aataccgatg tccaaatctc tgtagttcaa atatgccaat 2580
ctagggtttt tagaaacgta tggagtcatg aagttataga tgtttctaat ccagtttaag 2640
tgcttttcgt tatcttcttg cttttcccat gaacaaatgt accacaattc gtataagata 2700
ccagctctat gaggaaatgg aatggcagat tcactgattt cgtccattat accaccgtat 2760
ggatacaagg cgtacatgcc tgcaccaata tcttcttcgt acaatttttc taagatttgg 2820
acgaaaactg attcaggtat tggcttttta acgtagtcta acttaatttt aaaggcaccg 2880
ttttgacctg cggatctatc caataatatt tctttgttga agttgtctgt atcgtagttg 2940
acaacacctg aataaaagat gatggtgtcg atccaagaca attgtctaca atcagttttc 3000
ttaataccta attctggaaa agacttattc atcaagtcta ctaaggaatc gacaccaccc 3060
aagaaaactg aagaaaagta tgtgtggata gcagtcttat ttttaccttg gttatcggtg 3120
atgtttcttg tgatgaaatg agtcatcaac aacaagtcct tatcgtactt gtatgcgatg 3180
ttttgccact tattgaccaa tttaactaat tcatggattt ccattatctt tttgactgag 3240
aacatagtag actttggtac tgcgactaat cttatcttcc aagcaactat gataccgaat 3300
gattctgcac caccacctct caaagcccaa aataagtctt cacccataga ctttctatcc 3360
aaaactttac cgtgaacatt taccaaatga gcgtcgatta tgttatcagc ggccaaaccg 3420
tagtttctca ttaaaggacc ataaccacca ccaccaaaat gaccacctgc gcaaactgtt 3480
ggacagtaac cagcagccaa tgataagttt tcattctttt cgttaaccca gtagtatact 3540
tcacccaatg ttgcaccagc ttcaacccaa gcagtttgtg agtgtacgtc tattttaatt 3600
gatctcatgt ttctcaaatc aacgataacg aatggaactt gggagatgta tgacatgcct 3660

```
tcactatcat gaccaccgga tctagttcta atttgcaaac caaccttttt agaacataag   3720
atagtacctt ggatgtgaga tacatgacta ggggttacaa tgaccaaagg ttttggagtg   3780
gtatcagaag tgaatctcaa attatggatt gtactgttca agacggacat gtacaatggg   3840
ttgttttgag tgtaaaccaa cttcaaattg gtggcgttat taggtatgta ttgtgagaag   3900
cacttcaaaa agttttctct tgggtttgcg atacttgttt ggatgttaaa ggaaaagaaa   3960
aagaagatga tcttgcatac gaaccaaaag gagaaagttg aacatttcat aggacctgga   4020
ttttcttcaa cgtcaccaca ggtcaacaaa gaacctctac cttcaataaa aacgtatacc   4080
aaatattcag cgtagtacaa tttccacata aactcgtaga atcttctacc tgcttcaggg   4140
tcataatttg tcaaagcgaa atctctagtt tgcaagatca accagaaagc caagatggca   4200
tgtgacaaca acataacgtt agaattaaag gcttgtggcc aaatgatacc tgccaaaatg   4260
gctgcgacgt aacttaacaa aacgataccg gagcagaaca aagtcaaatt tcttgaaccg   4320
tacttagaag ccaaggtact aataccgaac tttgtgtcac cttcaacgtc agaggcatcc   4380
ttgatcaagg ctaatgcaga acccatactt ttcatgaatg ccaacaaaaa tgtgaatgaa   4440
ggtctcaatt cgaatggcaa acctaaagca gctcttgaag cgtagtagaa ggtgaagttt   4500
gtgatgatat gagctaagaa attcaacaaa aaggcagtac tagggttttg tttccatcta   4560
aaaggtggta cggaatagac aataccaccg aagataccga aacagtaacc gaagatgtac   4620
aatggaccac ccttcatttt aattgtgatg atcaaaccga acaaggctac tatgatagac   4680
atgatccatg cagtattgac ggatatttca cctgaagcca aaggcaaatc tggtttgtta   4740
attctgtcga tgtgcaaatc gtatatttga ttaattgtag tggtgaatga agcgatgcac   4800
aagatggcaa ctaaaaagaa aaatgccttg aacatcaagg accatgaaat taagttagtg   4860
ttatgcaaca attctttacc gaataaaccg catgcacaag aagtaaaagc gattatggtg   4920
tatggtcttt gcaacttcca acatgcttta ccgaagttca aaatttttgt ggcaacagag   4980
tgattatcac tttcaggtgg ttcagtttga tttgtagttg cagctctgat agagttctta   5040
gctatagaca aactttcgga gcacttattt tgtaagtgga aggacttggt tgaacaatgt   5100
tttgatggaa agttgttgta agagtactta ataggtgtct ttggatgtct gtaacacaac   5160
aatgatgttt ttggattgtt gttgtgagga ttcaataagg tatgatagtt agtttggaag   5220
gagaaagtac agacggatga taaacccata ctagttctag atccgtcgaa actaagttct   5280
tggtgtttta aaactaaaaa aaagactaac tataaaagta gaatttaaga agtttaagaa   5340
atagatttac agaattacaa tcaataccta ccgtctttat atacttatta gtcaagtagg   5400
ggaataattt cagggaactg gtttaaacct ttttttttcag ctttttccaa atcagagaga   5460
gcagaaggta atagaaggtg taagaaaatg agatagatac atgcgtgggt caattgcctt   5520
gtgtcatcat ttactccagg caggttgcat cactccattg aggttgtgcc cgtttttttgc   5580
ctgtttgtgc cctgttctct gtagttgcgc taagagaatg gacctatgaa ctgatggttg   5640
gtgaagaaaa caatattttg gtgctgggat tctttttttt tctggatgcc agcttaaaaa   5700
gcgggctcca ttatatttag tggatgccag gaataaacct gttcacccaa gcaccatcag   5760
tgttatatat tctgtgtaac ccgcccccta ttttggcatg tacgggttac agcagaatta   5820
aaaggctaat tttttgacta aataaagtta ggaaaatcac tactattaat tatttacgta   5880
ttctttgaaa tggcagtatt gataatgata aactcgagag ctccagcttt tgttcccttt   5940
agtgagggtt aattgcgcgc ttggcgtaat catggtcata gctgtttcct gtgtgaaatt   6000
gttatccgct cacaattcca cacaacatag gagccggaag cataaagtgt aaagcctggg   6060
```

```
gtgcctaatg agtgaggtaa ctcacattaa ttgcgttgcg ctcactgccc gctttccagt   6120
cgggaaacct gtcgtgccag ctgcattaat gaatcggcca acgcgcgggg agaggcggtt   6180
tgcgtattgg gcgctcttcc gcttcctcgc tcactgactc gctgcgctcg gtcgttcggc   6240
tgcggcgagc ggtatcagct cactcaaagg cggtaatacg gttatccaca gaatcagggg   6300
ataacgcagg aaagaacatg tgagcaaaag gccagcaaaa ggccaggaac cgtaaaaagg   6360
ccgcgttgct ggcgtttttc cataggctcc gcccccctga cgagcatcac aaaaatcgac   6420
gctcaagtca gaggtggcga aacccgacag gactataaag ataccaggcg tttccccctg   6480
gaagctccct cgtgcgctct cctgttccga ccctgccgct taccggatac ctgtccgcct   6540
ttctcccttc gggaagcgtg gcgctttctc atagctcacg ctgtaggtat ctcagttcgg   6600
tgtaggtcgt tcgctccaag ctgggctgtg tgcacgaacc ccccgttcag cccgaccgct   6660
gcgccttatc cggtaactat cgtcttgagt ccaacccggt aagacacgac ttatcgccac   6720
tggcagcagc cactggtaac aggattagca gagcgaggta tgtaggcggt gctacagagt   6780
tcttgaagtg gtggcctaac tacggctaca ctagaaggac agtatttggt atctgcgctc   6840
tgctgaagcc agttaccttc ggaaaaagag ttggtagctc ttgatccggc aaacaaacca   6900
ccgctggtag cggtggtttt tttgtttgca agcagcagat tacgcgcaga aaaaaaggat   6960
ctcaagaaga tcctttgatc ttttctacgg ggtctgacgc tcagtggaac gaaaactcac   7020
gttaagggat tttggtcatg agattatcaa aaaggatctt cacctagatc cttttaaatt   7080
aaaaatgaag ttttaaatca atctaaagta tatatgagta aacttggtct gacagttacc   7140
aatgcttaat cagtgaggca cctatctcag cgatctgtct atttcgttca tccatagttg   7200
cctgactccc cgtcgtgtag ataactacga tacgggaggg cttaccatct ggccccagtg   7260
ctgcaatgat accgcgagac ccacgctcac cggctccaga tttatcagca ataaaccagc   7320
cagccggaag ggccgagcgc agaagtggtc ctgcaacttt atccgcctcc atccagtcta   7380
ttaattgttg ccgggaagct agagtaagta gttcgccagt taatagtttg cgcaacgttg   7440
ttgccattgc tacaggcatc gtggtgtcac gctcgtcgtt tggtatggct tcattcagct   7500
ccggttccca acgatcaagg cgagttacat gatcccccat gttgtgcaaa aaagcggtta   7560
gctccttcgg tcctccgatc gttgtcagaa gtaagttggc cgcagtgtta tcactcatgg   7620
ttatggcagc actgcataat tctcttactg tcatgccatc cgtaagatgc ttttctgtga   7680
ctggtgagta ctcaaccaag tcattctgag aatagtgtat gcggcgaccg agttgctctt   7740
gcccggcgtc aatacgggat aataccgcgc cacatagcag aactttaaaa gtgctcatca   7800
ttggaaaacg ttcttcgggg cgaaaactct caaggatctt accgctgttg agatccagtt   7860
cgatgtaacc cactcgtgca cccaactgat cttcagcatc ttttactttc accagcgttt   7920
ctgggtgagc aaaaacagga aggcaaaatg ccgcaaaaaa gggaataagg gcgacacgga   7980
aatgttgaat actcatactc ttcctttttc aatattattg aagcatttat cagggttatt   8040
gtctcatgag cggatacata tttgaatgta tttagaaaaa taaacaaata ggggttccgc   8100
gcacatttcc ccgaaaagtg ccacctgggt ccttttcatc acgtgctata aaaataatta   8160
taatttaaat tttttaatat aaatatataa attaaaaata gaaagtaaaa aaagaaatta   8220
aagaaaaaat agtttttgtt ttccgaagat gtaaaagact ctagggggat cgccaacaaa   8280
tactaccttt tatcttgctc ttcctgctct caggtattaa tgccgaattg tttcatcttg   8340
tctgtgtaga agaccacaca cgaaaatcct gtgattttac attttactta tcgttaatcg   8400
```

```
aatgtatatc tatttaatct gcttttcttg tctaataaat atatatgtaa agtacgcttt   8460
ttgttgaaat tttttaaacc tttgtttatt tttttttctt cattccgtaa ctcttctacc   8520
ttctttattt actttctaaa atccaaatac aaaacataaa aataaataaa cacagagtaa   8580
attcccaaat tattccatca ttaaaagata cgaggcgcgt gtaagttaca ggcaagcgat   8640
ccgtcctaag aaaccattat tatcatgaca ttaacctata aaaataggcg tatcacgagg   8700
ccctttcgtc                                                          8710
```

<210> SEQ ID NO 12
<211> LENGTH: 9617
<212> TYPE: DNA
<213> ORGANISM: Artificial Sequence
<220> FEATURE:
<223> OTHER INFORMATION: Codon optimized

<400> SEQUENCE: 12

```
ttatcatgac attaacctat aaaaataggc gtatcacgag gccctttcgt ctcgcgcgtt     60
tcggtgatga cggtgaaaac ctctgacaca tgcagctccc ggagacggtc acagcttgtc    120
tgtaagcgga tgccgggagc agacaagccc gtcagggcgc gtcagcgggt gttggcgggt    180
gtcggggctg gcttaactat gcggcatcag agcagattgt actgagagtg caccacgctt    240
ttcaattcaa ttcatcattt ttttttatt cttttttttg atttcggttt ctttgaaatt    300
tttttgattc ggtaatctcc gaacagaagg aagaacgaag gaaggagcac agacttagat    360
tggtatatat acgcatatgt agtgttgaag aaacatgaaa ttgcccagta ttcttaaccc    420
aactgcacag aacaaaaacc tgcaggaaac gaagataaat catgtcgaaa gctacatata    480
aggaacgtgc tgctactcat cctagtcctg ttgctgccaa gctatttaat atcatgcacg    540
aaaagcaaac aaacttgtgt gcttcattgg atgttcgtac caccaaggaa ttactggagt    600
tagttgaagc attaggtccc aaaatttgtt tactaaaaac acatgtggat atcttgactg    660
atttttccat ggagggcaca gttaagccgc taaaggcatt atccgccaag tacaattttt    720
tactcttcga agacagaaaa tttgctgaca ttggtaatac agtcaaattg cagtactctg    780
cgggtgtata cagaatagca gaatgggcag acattacgaa tgcacacggt gtggtgggcc    840
caggtattgt tagcggtttg aagcaggcgg cagaagaagt aacaaaggaa cctagaggcc    900
ttttgatgtt agcagaattg tcatgcaagg gctccctatc tactggagaa tatactaagg    960
gtactgttga cattgcgaag agcgacaaag attttgttat cggctttatt gctcaaagag   1020
acatgggtgg aagagatgaa ggttacgatt ggttgattat gacacccggt gtgggtttag   1080
atgacaaggg agacgcattg ggtcaacagt atagaaccgt ggatgatgtg gtctctacag   1140
gatctgacat tattattgtt ggaagaggac tatttgcaaa gggaagggat gctaaggtag   1200
agggtgaacg ttacagaaaa gcaggctggg aagcatattt gagaagatgc ggccagcaaa   1260
actaaaaaac tgtattataa gtaaatgcat gtatactaaa ctcacaaatt agagcttcaa   1320
tttaattata tcagttatta ccctgcggtg tgaaataccg cacagatgcg taaggagaaa   1380
ataccgcatc aggaaattgt aaacgttaat attttgttaa aattcgcgtt aaatttttgt   1440
taaatcagct cattttttaa ccaataggcc gaaatcggca aaatccctta taaatcaaaa   1500
gaatagaccg agatagggtt gagtgttgtt ccagtttgga acaagagtcc actattaaag   1560
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gcccccgatt tagagcttga cggggaaagc cggcgaacgt ggcgagaaag   1740
```

```
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga aggggggatg tgctgcaagg cgattaagtt gggtaacgcc agggttttcc   1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga aacgcagatg tgcctcgcgc   2160
cgcactgctc cgaacaataa agattctaca atactagctt ttatggttat gaagaggaaa   2220
aattggcagt aacctggccc cacaaacctt caaattaacg aatcaaatta acaaccatag   2280
gatgataatg cgattagttt tttagcctta tttctggggt aattaatcag cgaagcgatg   2340
atttttgatc tattaacaga tatataaatg gaaaagctgc ataaccactt taactaatac   2400
tttcaacatt ttcagtttgt attacttctt attcaaatgt cataaaagta tcaacaaaaa   2460
attgttaata tacctctata ctttaacgtc aaggagaaaa aaccccggat tctagaacta   2520
gtggatcccc catcatgaac catttgagag ccgaaggtcc tgcctccgta ttagccatag   2580
gtacagccaa cccagaaaac atattgatcc aagatgaatt tcctgattat tacttcagag   2640
ttaccaagag tgaacacatg actcaattga aggaaaagtt tagaaaaata tgtgataagt   2700
ctatgatcag aaagagaaac tgcttcttga acgaagaaca tttgaagcaa aatccaagat   2760
tggtagaaca cgaaatgcaa acattggatg ccagacaaga catgttagtt gtcgaagttc   2820
ctaaattggg taaagatgct tgtgcaaaag ccattaagga atggggtcaa ccaaagtcaa   2880
agatcactca tttgattttt acaagtgcat ctactacaga tatgcctggt gcagactacc   2940
actgtgccaa attgttaggt ttgtcaccat ccgttaagag agtcatgatg tatcaattag   3000
gttgctacgg tggtggtact gttttgagaa tcgctaagga tattgcagaa aacaacaagg   3060
gtgccagagt attagctgtt tgttgcgaca ttatggcttg cttgtttaga ggtccaagtg   3120
attctgactt ggaattgtta gttggtcaag ctatcttcgg tgacggtgct gctgctgtta   3180
ttgttggtgc agaacctgac gaatctgttg gtgaaagacc aatatttgaa ttagtcagta   3240
caggtcaaac catcttgcct aattctgaag gtacaattgg tggtcatata agagaagcag   3300
gtttgatctt cgatttgcac aaagacgttc caatgttaat ctctaacaac atagaaaagt   3360
gtttgataga agcattcact cctataggta tctcagattg gaactctatt ttctggataa   3420
cacatccagg tggtaaagcc attttggata aggttgaaga aaaattggat ttgaagaaag   3480
aaaagtttgt agatagtaga catgttttat ctgaacacgg taacatgtct tcatccactg   3540
tcttgttcgt aatggatgaa ttgagaaaga gatcattaga agagggtaaa tctactactg   3600
gtgacggttt tgaatggggt gtcttatttg gtttcggtcc tggtttgacc gtcgaaagag   3660
tagttgtcag atcagtacca attaaatatg aaggtagagg ttccttgtta acttgtggtg   3720
acgttgaaga aaacccaggt cctatggccg tcaagcattt gatagtattg aagtttaaag   3780
atgaaatcac agaagctcaa aaggaagaat ttttcaagac ctacgttaat ttggtcaaca   3840
ttatacctgc tatgaaagat gtatactggg gtaaagacgt tacacaaaag aaagaagaag   3900
gttatacaca cattgtcgaa gtaaccttcg aatcagttga aactatccaa gattacatca   3960
ttcatccagc tcacgttggt tttggtgacg tttacagatc cttctgggaa aaattgttga   4020
tcttcgatta caccccaaga aagttaaagc caaaataatg ataacgagaa taatatcaag   4080
```

```
aataccttag aacaacatcg acaacaacaa caggcatttt cggatatgag tcacgtggag   4140
tattccagaa ttacaaaatt ttttcaagaa caaccactgg agggatatac ccttttctct   4200
cacaggtctg cgccatgggt ttatcatccg tctgtacttt ctccttccaa actaactatc   4260
ataccttatt gaatcctcac aacaacaatc caaaaacatc attgttgtgt tacagacatc   4320
caaagacacc tattaagtac tcttacaaca actttccatc aaaacattgt tcaaccaagt   4380
ccttccactt acaaaataag tgctccgaaa gtttgtctat agctaagaac tctatcagag   4440
ctgcaactac aaatcaaact gaaccacctg aaagtgataa tcactctgtt gccacaaaaa   4500
ttttgaactt cggtaaagca tgttggaagt tgcaaagacc atacaccata atcgctttta   4560
cttcttgtgc atgcggttta ttcggtaaag aattgttgca taacactaac ttaatttcat   4620
ggtccttgat gttcaaggca tttttctttt tagttgccat cttgtgcatc gcttcattca   4680
ccactacaat taatcaaata tacgatttgc acatcgacag aattaacaaa ccagatttgc   4740
ctttggcttc aggtgaaata tccgtcaata ctgcatggat catgtctatc atagtagcct   4800
tgttcggttt gatcatcaca attaaaatga agggtggtcc attgtacatc ttcggttact   4860
gtttcggtat cttcggtggt attgtctatt ccgtaccacc ttttagatgg aaacaaaacc   4920
ctagtactgc ctttttgttg aatttcttag ctcatatcat cacaaacttc accttctact   4980
acgcttcaag agctgcttta ggtttgccat tcgaattgag accttcattc acatttttgt   5040
tggcattcat gaaaagtatg ggttctgcat tagccttgat caaggatgcc tctgacgttg   5100
aaggtgacac aaagttcggt attagtacct tggcttctaa gtacggttca agaaatttga   5160
ctttgttctg ctccggtatc gttttgttaa gttacgtcgc agccattttg gcaggtatca   5220
tttggccaca agcctttaat tctaacgtta tgttgttgtc acatgccatc ttggctttct   5280
ggttgatctt gcaaactaga gatttcgctt tgacaaatta tgaccctgaa gcaggtagaa   5340
gattctacga gtttatgtgg aaattgtact acgctgaata tttggtatac gtttttattg   5400
aaggtagagg ttctttgttg acctgtggtg acgttgaaga aaatccaggt cctatgaaat   5460
gttcaacttt ctccttttgg ttcgtatgca agatcatctt cttttctttt tcctttaaca   5520
tccaaacaag tatcgcaaac ccaagagaaa actttttgaa gtgcttctca caatacatac   5580
ctaataacgc caccaatttg aagttggttt acactcaaaa caacccattg tacatgtccg   5640
tcttgaacag tacaatccat aatttgagat tcacttctga taccactcca aaaccttttgg  5700
tcattgtaac ccctagtcat gtatctcaca tccaaggtac tatcttatgt tctaaaaagg   5760
ttggtttgca aattagaact agatccggtg gtcatgatag tgaaggcatg tcatacatct   5820
cccaagttcc attcgttatc gttgatttga gaaacatgag atcaattaaa atagacgtac   5880
actcacaaac tgcttgggtt gaagctggtg caacattggg tgaagtatac tactgggtta   5940
acgaaaagaa tgaaaactta tcattggctg ctggttactg tccaacagtt tgcgcaggtg   6000
gtcattttgg tggtggtggt tatggtcctt taatgagaaa ctacggtttg gccgctgata   6060
acataatcga cgctcatttg gtaaatgttc acggtaaagt tttggataga aagtctatgg   6120
gtgaagactt attttgggct ttgagaggtg gtggtgcaga atcattcggt atcatagttg   6180
cttggaagat aagattagtc gcagtaccaa agtctactat gttctcagtc aaaaagataa   6240
tggaaatcca tgaattagtt aaattggtca ataagtggca aaacatcgca tacaagtacg   6300
ataaggactt gttgttgatg actcatttca tcacaagaaa catcaccgat aaccaaggta   6360
aaaataagac tgctatccac acatactttt cttcagtttt cttgggtggt gtcgattcct   6420
tagtagactt gatgaataag tcttttccag aattaggtat taagaaaact gattgtagac   6480
```

```
aattgtcttg gatcgacacc atcatctttt attcaggtgt tgtcaactac gatacagaca   6540
acttcaacaa agaaatatta ttggatagat ccgcaggtca aaacggtgcc tttaaaatta   6600
agttagacta cgttaaaaag ccaatacctg aatcagtttt cgtccaaatc ttagaaaaat   6660
tgtacgaaga agatattggt gcaggcatgt acgccttgta tccatacggt ggtataatgg   6720
acgaaatcag tgaatctgcc attccatttc ctcatagagc tggtatctta tacgaattgt   6780
ggtacatttg ttcatgggaa aagcaagaag ataacgaaaa gcacttaaac tggattagaa   6840
acatctataa cttcatgact ccatacgttt ctaaaaaccc tagattggca tatttgaact   6900
acagagattt ggacatcggt attaacgatc caaagaatcc taacaactat acccaagcta   6960
gaatttgggg tgaaaaatac ttcggtaaaa atttcgatag attagtaaag gttaagacat   7020
tggttgaccc aaacaacttc tttagaaacg aacaatccat tccaccttta cctagacata   7080
gacactgatg ggctgcagga attcgatatc aagcttatcg ataccgtcga cctcgagtca   7140
tgtaattagt tatgtcacgc ttacattcac gccctccccc cacatccgct ctaaccgaaa   7200
aggaaggagt tagacaacct gaagtctagg tccctattta tttttttata gttatgttag   7260
tattaagaac gttatttata tttcaaattt ttcttttttt tctgtacaga cgcgtgtacg   7320
catgtaacat tatactgaaa accttgcttg agaaggtttt gggacgctcg aaggctttaa   7380
tttgcggccg gtacccagct tttgttccct ttagtgaggg ttaattccga gcttggcgta   7440
atcatggtca tagctgtttc ctgtgtgaaa ttgttatccg ctcacaattc cacacaacat   7500
aggagccgga agcataaagt gtaaagcctg gggtgcctaa tgagtgaggt aactcacatt   7560
aattgcgttg cgctcactgc ccgctttcca gtcgggaaac ctgtcgtgcc agctgcatta   7620
atgaatcggc caacgcgcgg ggagaggcgg tttgcgtatt gggcgctctt ccgcttcctc   7680
gctcactgac tcgctgcgct cggtcgttcg gctgcggcga gcggtatcag ctcactcaaa   7740
ggcggtaata cggttatcca cagaatcagg ggataacgca ggaaagaaca tgtgagcaaa   7800
aggccagcaa aaggccagga accgtaaaaa ggccgcgttg ctggcgtttt tccataggct   7860
cggccccccct gacgagcatc acaaaaatcg acgctcaagt cagaggtggc gaaacccgac   7920
aggactataa agataccagg cgtttccccc tggaagctcc ctcgtgcgct ctcctgttcc   7980
gaccctgccg cttaccggat acctgtccgc ctttctccct tcgggaagcg tggcgctttc   8040
tcaatgctca cgctgtaggt atctcagttc ggtgtaggtc gttcgctcca agctgggctg   8100
tgtgcacgaa ccccccgttc agcccgaccg ctgcgcctta tccggtaact atcgtcttga   8160
gtccaacccg gtaagacacg acttatcgcc actggcagca gccactggta acaggattag   8220
cagagcgagg tatgtaggcg gtgctacaga gttcttgaag tggtggccta actacggcta   8280
cactagaagg acagtatttg gtatctgcgc tctgctgaag ccagttacct tcggaaaaag   8340
agttggtagc tcttgatccg gcaaacaaac caccgctggt agcggtggtt tttttgtttg   8400
caagcagcag attacgcgca gaaaaaaagg atctcaagaa gatcctttga tcttttctac   8460
ggggtctgac gctcagtgga acgaaaactc acgttaaggg attttggtca tgagattatc   8520
aaaaaggatc ttcacctaga tccttttaaa ttaaaaatga agttttaaat caatctaaag   8580
tatatatgag taaacttggt ctgacagtta ccaatgctta atcagtgagg cacctatctc   8640
agcgatctgt ctatttcgtt catccatagt tgcctgactg ccccgtcgtgt agataactac   8700
gatacgggag ggcttaccat ctggccccag tgctgcaatg ataccgcgag acccacgctc   8760
accggctcca gatttatcag caataaacca gccagccgga agggccgagc gcagaagtgg   8820
```

```
tcctgcaact ttatccgcct ccatccagtc tattaattgt tgccgggaag ctagagtaag   8880

tagttcgcca gttaatagtt tgcgcaacgt tgttgccatt gctacaggca tcgtggtgtc   8940

acgctcgtcg tttggtatgg cttcattcag ctccggttcc caacgatcaa ggcgagttac   9000

atgatccccc atgttgtgaa aaaaagcggt tagctccttc ggtcctccga tcgttgtcag   9060

aagtaagttg gccgcagtgt tatcactcat ggttatggca gcactgcata attctcttac   9120

tgtcatgcca tccgtaagat gcttttctgt gactggtgag tactcaacca agtcattctg   9180

agaatagtgt atgcggcgac cgagttgctc ttgcccggcg tcaatacggg ataataccgc   9240

gccacatagc agaactttaa aagtgctcat cattggaaaa cgttcttcgg ggcgaaaact   9300

ctcaaggatc ttaccgctgt tgagatccag ttcgatgtaa cccactcgtg cacccaactg   9360

atcttcagca tcttttactt tcaccagcgt ttctgggtga gcaaaaacag gaaggcaaaa   9420

tgccgcaaaa aagggaataa gggcgacacg gaaatgttga atactcatac tcttcctttt   9480

tcaatattat tgaagcattt atcagggtta ttgtctcatg agcggataca tatttgaatg   9540

tatttagaaa aataaacaaa taggggttcc gcgcacattt ccccgaaaag tgccacctga   9600

cgtctaagaa accatta                                                  9617
```

```
<210> SEQ ID NO 13
<211> LENGTH: 7879
<212> TYPE: DNA
<213> ORGANISM: Artificial Sequence
<220> FEATURE:
<223> OTHER INFORMATION: Codon optimized

<400> SEQUENCE: 13

aacctataaa aataggcgta tcacgaggcc ctttcgtctc gcgcgtttcg gtgatgacgg     60

tgaaaacctc tgacacatgc agctcccgga gacggtcaca gcttgtctgt aagcggatgc    120

cgggagcaga caagcccgtc agggcgcgtc agcgggtgtt ggcgggtgtc ggggctggct    180

taactatgcg gcatcagagc agattgtact gagagtgcac cacgcttttc aattcaattc    240

atcatttttt ttttattctt ttttttgatt tcggtttctt tgaaattttt ttgattcggt    300

aatctccgaa cagaaggaag aacgaaggaa ggagcacaga cttagattgg tatatatacg    360

catatgtagt gttgaagaaa catgaaattg cccagtattc ttaacccaac tgcacagaac    420

aaaaacctgc aggaaacgaa gataaatcat gtcgaaagct acatataagg aacgtgctgc    480

tactcatcct agtcctgttg ctgccaagct atttaatatc atgcacgaaa agcaaacaaa    540

cttgtgtgct tcattggatg ttcgtaccac caaggaatta ctggagttag ttgaagcatt    600

aggtcccaaa atttgtttac taaaaacaca tgtggatatc ttgactgatt tttccatgga    660

gggcacagtt aagccgctaa aggcattatc cgccaagtac aatttttac tcttcgaaga    720

cagaaaattt gctgacattg gtaatacagt caaattgcag tactctgcgg gtgtatacag    780

aatagcagaa tggcagacaa ttacgaatgc acacggtgtg gtgggcccag gtattgttag    840

cggtttgaag caggcggcag aagaagtaac aaaggaacct agaggccttt tgatgttagc    900

agaattgtca tgcaagggct ccctatctac tggagaatat actaagggta ctgttgacat    960

tgcgaagagc gacaaagatt ttgttatcgg ctttattgct caaagagaca tgggtggaag   1020

agatgaaggt tacgattggt tgattatgac acccggtgtg ggtttagatg acaagggaga   1080

cgcattgggt caacagtata gaaccgtgga tgatgtggtc tctacaggat ctgacattat   1140

tattgttgga agaggactat ttgcaaaggg aagggatgct aaggtagagg gtgaacgtta   1200

cagaaaagca ggctgggaag catatttgag aagatgcggc cagcaaaact aaaaaactgt   1260
```

-continued

```
attataagta aatgcatgta tactaaactc acaaattaga gcttcaattt aattatatca   1320
gttattaccc tgcggtgtga aataccgcac agatgcgtaa ggagaaaata ccgcatcagg   1380
aaattgtaaa cgttaatatt ttgttaaaat tcgcgttaaa tttttgttaa atcagctcat   1440
tttttaacca ataggccgaa atcggcaaaa tcccttataa atcaaaagaa tagaccgaga   1500
tagggttgag tgttgttcca gtttggaaca agagtccact attaaagaac gtggactcca   1560
acgtcaaagg gcgaaaaacc gtctatcagg gcgatggccc actacgtgaa ccatcaccct   1620
aatcaagttt tttggggtcg aggtgccgta aagcactaaa tcggaaccct aaagggagcc   1680
cccgatttag agcttgacgg ggaaagccgg cgaacgtggc gagaaaggaa gggaagaaag   1740
cgaaaggagc gggcgctagg gcgctggcaa gtgtagcggt cacgctgcgc gtaaccacca   1800
cacccgccgc gcttaatgcg ccgctacagg gcgcgtcgcg ccattcgcca ttcaggctgc   1860
gcaactgttg ggaagggcga tcggtgcggg cctcttcgct attacgccag ctggcgaagg   1920
ggggatgtgc tgcaaggcga ttaagttggg taacgccagg gttttcccag tcacgacgtt   1980
gtaaaacgac ggccagtgaa ttgtaatacg actcactata gggcgaattg gagctctagt   2040
acggattaga agccgccgag cgggcgacag ccctccgacg gaagactctc ctccgtgcgt   2100
cctcgtcttc accggtcgcg ttcctgaaac gcagatgtgc ctcgcgccgc actgctccga   2160
acaataaaga ttctacaata ctagctttta tggttatgaa gaggaaaaat tggcagtaac   2220
ctggccccac aaaccttcaa attaacgaat caaattaaca accataggat gataatgcga   2280
ttagtttttt agccttattt ctggggtaat taatcagcga agcgatgatt tttgatctat   2340
taacagatat ataaatggaa aagctgcata accactttaa ctaatacttt caacattttc   2400
agtttgtatt acttcttatt caaatgtcat aaaagtatca acaaaaaatt gttaatatac   2460
ctctatactt taacgtcaag gagaaaaaac cccggattct agaactagtg gatcatgaac   2520
catttgagag ccgaaggtcc tgcctccgta ttagccatag gtacagccaa cccagaaaac   2580
atattgatcc aagatgaatt tcctgattat tacttcagag ttaccaagag tgaacacatg   2640
actcaattga aggaaaagtt tagaaaaata tgtgataagt ctatgatcag aaagagaaac   2700
tgcttcttga acgaagaaca tttgaagcaa aatccaagat tggtagaaca cgaaatgcaa   2760
acattggatg ccagacaaga catgttagtt gtcgaagttc ctaaattggg taaagatgct   2820
tgtgcaaaag ccattaagga atggggtcaa ccaaagtcaa agatcactca tttgattttt   2880
acaagtgcat ctactacaga tatgcctggt gcagactacc actgtgccaa attgttaggt   2940
ttgtcaccat ccgttaagag agtcatgatg tatcaattag gttgctacgg tggtggtact   3000
gttttgagaa tcgctaagga tattgcagaa aacaacaagg gtgccagagt attagctgtt   3060
tgttgcgaca ttatggcttg cttgtttaga ggtccaagtg attctgactt ggaattgtta   3120
gttggtcaag ctatcttcgg tgacggtgct gctgctgtta ttgttggtgc agaacctgac   3180
gaatctgttg gtgaaagacc aatatttgaa ttagtcagta caggtcaaac catcttgcct   3240
aattctgaag gtacaattgg tggtcatata agagaagcag gtttgatctt cgatttgcac   3300
aaagacgttc caatgttaat ctctaacaac atagaaaagt gtttgataga agcattcact   3360
cctataggta tctcagattg gaactctatt ttctggataa cacatccagg tggtaaagcc   3420
attttggata aggttgaaga aaaattggat ttgaagaaag aaaagtttgt agatagtaga   3480
catgttttat ctgaacacgg taacatgtct tcatccactg tcttgttcgt aatggatgaa   3540
ttgagaaaga gatcattaga agagggtaaa tctactactg gtgacggttt tgaatggggt   3600
```

```
gtcttatttg gtttcggtcc tggtttgacc gtcgaaagag tagttgtcag atcagtacca   3660
attaaatatg aaggtagagg ttccttgtta acttgtggtg acgttgaaga aaacccaggt   3720
cctatggccg tcaagcattt gatagtattg aagtttaaag atgaaatcac agaagctcaa   3780
aaggaagaat tttcaagacc ctacgttaat ttggtcaaca ttatacctgc tatgaaagat   3840
gtatactggg gtaaagacgt tacacaaaag aaagaagaag gttatacaca cattgtcgaa   3900
gtaaccttcg aatcagttga aactatccaa gattacatca ttcatccagc tcacgttggt   3960
tttggtgacg tttacagatc cttctgggaa aaattgttga tcttcgatta caccccaaga   4020
aagtgataac gagaataata tcaagaatac cttagaacaa catcgacaac aacaacaggc   4080
attttcggat atgagtcacg tggagtattc cagaattaca aaattttttc aagaacaacc   4140
actggaggga tataccettt tctctcacag gtctgcgcca tgggtttatc atccgtctgt   4200
actttctcct tccaaactaa ctatcatacc ttattgaatc ctcacaacaa caatccaaaa   4260
acatcattgt tgtgttacag acatccaaag acacctatta agtactctta caacaacttt   4320
ccatcaaaac attgttcaac caagtccttc cacttacaaa ataagtgctc cgaaagtttg   4380
tctatagcta agaactctat cagagctgca actacaaatc aaactgaacc acctgaaagt   4440
gataatcact ctgttgccac aaaaattttg aacttcggta aagcatgttg gaagttgcaa   4500
agaccataca ccataatcgc ttttacttct tgtgcatgcg gtttattcgg taaagaattg   4560
ttgcataaca ctaacttaat ttcatggtcc ttgatgttca aggcattttt ctttttagtt   4620
gccatcttgt gcatcgcttc attcaccact acaattaatc aaatatacga tttgcacatc   4680
gacagaatta acaaaccaga tttgcctttg gcttcaggtg aaatatccgt caatactgca   4740
tggatcatgt ctatcatagt agccttgttc ggtttgatca tcacaattaa aatgaagggt   4800
ggtccattgt acatcttcgg ttactgtttc ggtatcttcg gtggtattgt ctattccgta   4860
ccacctttta gatggaaaca aaaccctagt actgcctttt tgttgaattt cttagctcat   4920
atcatcacaa acttcacctt ctactacgct tcaagagctg ctttaggttt gccattcgaa   4980
ttgagacctt cattcacatt tttgttggca ttcatgaaaa gtatgggttc tgcattagcc   5040
ttgatcaagg atgcctctga cgttgaaggt gacacaaagt tcggtattag taccttggct   5100
tctaagtacg gttcaagaaa tttgactttg ttctgctccg gtatcgtttt gttaagttac   5160
gtcgcagcca ttttggcagg tatcatttgg ccacaagcct ttaattctaa cgttatgttg   5220
ttgtcacatg ccatcttggc tttctggttg atcttgcaaa ctagagattt cgctttgaca   5280
aattatgacc ctgaagcagg tagaagattc tacgagttta tgtggaaatt gtactacgct   5340
gaatatttgg tatacgtttt tatttaacga taccgtcgac ctcgagtcat gtaattagtt   5400
atgtcacgct tacattcacg ccctcccccc acatccgctc taaccgaaaa ggaaggagtt   5460
agacaacctg aagtctaggt ccctatttat ttttttatag ttatgttagt attaagaacg   5520
ttatttatat ttcaaatttt tctttttttt ctgtacagac gcgtgtacgc atgtaacatt   5580
atactgaaaa ccttgcttga gaaggttttg ggacgctcga aggctttaat ttgcggccgg   5640
tacccagctt ttgttccctt tagtgagggt taattccgag cttggcgtaa tcatggtcat   5700
agctgtttcc tgtgtgaaat tgttatccgc tcacaattcc acacaacata ggagccggaa   5760
gcataaagtg taaagcctgg ggtgcctaat gagtgaggta actcacatta attgcgttgc   5820
gctcactgcc cgctttccag tcgggaaacc tgtcgtgcca gctgcattaa tgaatcggcc   5880
aacgcgcggg gagaggcggt ttgcgtattg ggcgctcttc cgcttcctcg ctcactgact   5940
cgctgcgctc ggtcgttcgg ctgcggcgag cggtatcagc tcactcaaag gcggtaatac   6000
```

```
ggttatccac agaatcaggg gataacgcag gaaagaacat gtgagcaaaa ggccagcaaa   6060
aggccaggaa ccgtaaaaag gccgcgttgc tggcgttttt ccataggctc ggcccccctg   6120
acgagcatca caaaaatcga cgctcaagtc agaggtggcg aaacccgaca ggactataaa   6180
gataccaggc gttcccccct ggaagctccc tcgtgcgctc tcctgttccg accctgccgc   6240
ttaccggata cctgtccgcc tttctccctt cgggaagcgt ggcgctttct caatgctcac   6300
gctgtaggta tctcagttcg gtgtaggtcg ttcgctccaa gctgggctgt gtgcacgaac   6360
cccccgttca gcccgaccgc tgcgccttat ccggtaacta tcgtcttgag tccaacccgg   6420
taagacacga cttatcgcca ctggcagcag ccactggtaa caggattagc agagcgaggt   6480
atgtaggcgg tgctacagag ttcttgaagt ggtggcctaa ctacggctac actagaagga   6540
cagtatttgg tatctgcgct ctgctgaagc cagttacctt cggaaaaaga gttggtagct   6600
cttgatccgg caaacaaacc accgctggta gcggtggttt ttttgtttgc aagcagcaga   6660
ttacgcgcag aaaaaaagga tctcaagaag atcctttgat cttttctacg gggtctgacg   6720
ctcagtggaa cgaaaactca cgttaaggga ttttggtcat gagattatca aaaaggatct   6780
tcacctagat ccttttaaat taaaaatgaa gttttaaatc aatctaaagt atatatgagt   6840
aaacttggtc tgacagttac caatgcttaa tcagtgaggc acctatctca gcgatctgtc   6900
tatttcgttc atccatagtt gcctgactgc ccgtcgtgta gataactacg atacgggagg   6960
gcttaccatc tggccccagt gctgcaatga taccgcgaga cccacgctca ccggctccag   7020
atttatcagc aataaaccag ccagccggaa gggccgagcg cagaagtggt cctgcaactt   7080
tatccgcctc catccagtct attaattgtt gccgggaagc tagagtaagt agttcgccag   7140
ttaatagttt gcgcaacgtt gttgccattg ctacaggcat cgtggtgtca cgctcgtcgt   7200
ttggtatggc ttcattcagc tccggttccc aacgatcaag gcgagttaca tgatccccca   7260
tgttgtgaaa aaaagcggtt agctccttcg gtcctccgat cgttgtcaga agtaagttgg   7320
ccgcagtgtt atcactcatg gttatggcag cactgcataa ttctcttact gtcatgccat   7380
ccgtaagatg cttttctgtg actggtgagt actcaaccaa gtcattctga gaatagtgta   7440
tgcggcgacc gagttgctct tgcccggcgt caatacggga taataccgcg ccacatagca   7500
gaactttaaa agtgctcatc attggaaaac gttcttcggg gcgaaaactc tcaaggatct   7560
taccgctgtt gagatccagt tcgatgtaac ccactcgtgc acccaactga tcttcagcat   7620
cttttacttt caccagcgtt tctgggtgag caaaaacagg aaggcaaaat gccgcaaaaa   7680
agggaataag ggcgacacgg aaatgttgaa tactcatact cttccttttt caatattatt   7740
gaagcattta tcagggttat tgtctcatga gcggatacat atttgaatgt atttagaaaa   7800
ataaacaaat aggggttccg cgcacatttc cccgaaaagt gccacctgac gtctaagaaa   7860
ccattattat catgacatt                                                7879
```

<210> SEQ ID NO 14
<211> LENGTH: 3353
<212> TYPE: DNA
<213> ORGANISM: Artificial Sequence
<220> FEATURE:
<223> OTHER INFORMATION: Codon optimized

<400> SEQUENCE: 14

```
actagtatgg gtaaaaacta taagtccttg gattcagtcg ttgcctcaga tttcatcgca     60
ttgggtatca cctcagaagt agcagaaaca ttacatggta gattggcaga aatcgtttgt    120
```

-continued

```
aattatggtg ctgcaacccc tcaaacttgg atcaacatcg ctaaccatat cttgtcacca    180

gatttgcctt tctccttaca ccaaatgttg ttttatggtt gctacaagga tttcggtcca    240

gccccacctg cttggattcc agaccctgaa aaagtcaagt caactaattt gggtgctttg    300

ttggaaaaga gaggtaaaga atttttgggt gtaaagtaca aagatccaat ttcttctttt    360

tctcacttcc aagaattttc tgttagaaac cctgaagtct attggagaac agtattgatg    420

gatgaaatga aaattagttt ctctaaggac ccagaatgta tcttgagaag agatgacatc    480

aacaacccag gtggttctga atggttacct ggtggttact tgaactcagc taaaaattgc    540

ttgaacgtaa actccaataa gaaattgaac gatactatga tcgtttggag agacgagggt    600

aacgatgact tgcctttgaa taagttgaca ttagatcaat tgagaaagag agtttggttg    660

gttggttatg cattggaaga aatgggttta gaaaaaggtt gtgcaatagc catcgatatg    720

ccaatgcatg ttgatgctgt tgttatatat ttggccatag tattggctgg ttacgtagtt    780

gtctctatag cagattcatt ttccgcccct gaaatctcaa ctagattgag attatccaaa    840

gctaaggcaa ttttcacaca agatcacatc atcagaggta aaaagagaat accattgtat    900

tcaagagtag ttgaagctaa atccccaatg gcaatagtta tcccttgtag tggttctaac    960

attggtgcag aattgagaga tggtgacata tcttgggatt actttttaga aagagccaag   1020

gagtttaaaa actgcgagtt tactgccaga gaacaacctg ttgatgctta tactaacatc   1080

ttattctcca gtggtactac aggtgaacca aaagcaattc cttggacaca agccacccca   1140

ttgaaggctg ctgctgatgg ttggtctcat ttggatatta gaaaaggtga cgttatagta   1200

tggccaacta atttgggttg gatgatgggt ccttggttgg tttatgctag tttgttaaat   1260

ggtgcatcta ttgccttgta caacggtagt cctttagtct ctggtttcgc taaatttgtt   1320

caagatgcaa aggtcacaat gttgggtgtc gtaccatcta ttgtaagatc atggaaatcc   1380

acaaattgtg tttcaggtta cgattggtcc accataagat gcttttcttc atccggtgaa   1440

gcctctaatg tagacgaata tttgtggtta atgggtagag ctaactacaa gccagttata   1500

gaaatgtgtg gtggtacaga aatcggtggt gctttttctg ctggttcatt tttgcaagct   1560

caatctttaa gttctttttc atcccaatgt atgggttgca ccttgtacat attagataag   1620

aacggttacc caatgcctaa aaataagcca ggtatcggtg aattggcatt aggtcctgtt   1680

atgtttggtg cctcaaaaac attgttaaac ggtaatcatc acgatgtcta tttcaagggt   1740

atgccaacct tgaatggtga agtattgaga agacatggtg acattttcga attgacctct   1800

aacggttact accatgcaca cggtagagcc gatgacacta tgaacatcgg tggtatcaaa   1860

attagttcta tcgaaatcga aagagtctgt aatgaagtag atgacagagt tttgaaacc   1920

actgctattg gtgttccacc tttgggtggt ggtccagaac aattggtcat atttttcgta   1980

ttgaaggatt caaacgacac aaccattgat ttgaaccaat tgagattatc ctttaacttg   2040

ggtttgcaaa agaaattgaa cccattattc aaagttacta gagttgtccc attgtcatcc   2100

ttacctagaa ctgcaacaaa caagatcatg agaagagttt tgagacaaca attcagtcat   2160

ttcgaagaag gtagaggttc tttgttaaca tgtggtgacg ttgaagaaaa tccaggtcct   2220

atggcttcag aaaaggaaat aagaagagaa agattcttga acgtattccc aaagttagtt   2280

gaagaattga acgctagttt gttagcttat ggtatgccta aagaagcctg cgattggtat   2340

gctcactctt taaactacaa tactccaggt ggtaaattga atagaggttt gagtgtagtt   2400

gatacttatg ctatcttgtc taacaaaacc gttgaacaat taggtcaaga agaatacgaa   2460

aaggtcgcta tcttgggttg gtgtattgaa ttgttgcaag catacttttt ggttgccgat   2520
```

```
gacatgatgg ataagtctat aacaagaaga ggtcaaccat gctggtacaa agttccagaa   2580

gttggtgaaa tagccataaa tgatgctttt atgttggaag ccgctatcta taaattgttg   2640

aagtcacatt tcagaaacga aaagtactac atcgatatta ccgaattatt ccacgaagtt   2700

actttccaaa cagaattggg tcaattgatg gatttgataa ctgcacctga agataaagtt   2760

gacttgtcaa agttttcctt gaagaaacat tcattcatcg tcacctttga aactgcttat   2820

tactccttct atttgccagt cgccttggct atgtacgtag ctggtattac tgatgaaaaa   2880

gacttgaagc aagcaagaga tgttttgata cctttgggtg aatacttcca aatccaagat   2940

gactacttag actgtttcgg tactccagaa caaataggta aaatcggtac agatattcaa   3000

gacaataagt gcagttgggt tattaacaag gctttggaat tagcatctgc cgaacaaaga   3060

aagactttgg atgaaaacta cggtaaaaag gactcagttg ctgaagcaaa gtgtaagaaa   3120

atttttaatg atttgaagat tgaacaattg taccatgaat acgaagaatc catcgctaaa   3180

gacttaaagg caaagattag tcaagttgat gaatcaagag gttttaaagc cgacgttttg   3240

acagctttct tgaataaggt ctacaagaga tcaaaggatt acaaggatca tgacggtgac   3300

tataaagacc acgatattga ctacaaagat gacgatgaca agtaagcggc cgc          3353
```

<210> SEQ ID NO 15
<211> LENGTH: 1553
<212> TYPE: DNA
<213> ORGANISM: Artificial Sequence
<220> FEATURE:
<223> OTHER INFORMATION: Codon optimized

<400> SEQUENCE: 15

```
actagtatga accatttgag agccgaaggt cctgcctccg tattagccat aggtacagcc     60

aacccagaaa acatattgat ccaagatgaa tttcctgatt attacttcag agttaccaag    120

agtgaacaca tgactcaatt gaaggaaaag tttagaaaaa tatgtgataa gtctatgatc    180

agaaagagaa actgcttctt gaacgaagaa catttgaagc aaaatccaag attggtagaa    240

cacgaaatgc aaacattgga tgccagacaa gacatgttag ttgtcgaagt tcctaaattg    300

ggtaaagatg cttgtgcaaa agccattaag gaatggggtc aaccaaagtc aaagatcact    360

catttgattt ttacaagtgc atctactaca gatatgcctg gtgcagacta ccactgtgcc    420

aaattgttag gtttgtcacc atccgttaag agagtcatga tgtatcaatt aggttgctac    480

ggtggtggta ctgttttgag aatcgctaag gatattgcag aaaacaacaa gggtgccaga    540

gtattagctg tttgttgcga cattatggct tgcttgttta gaggtccaag tgattctgac    600

ttggaattgt tagttggtca agctatcttc ggtgacggtg ctgctgctgt tattgttggt    660

gcagaacctg acgaatctgt tggtgaaaga ccaatatttg aattagtcag tacaggtcaa    720

accatcttgc ctaattctga aggtacaatt ggtggtcata taagagaagc aggtttgatc    780

ttcgatttgc acaaagacgt tccaatgtta atctctaaca acatagaaaa gtgtttgata    840

gaagcattca ctcctatagg tatctcagat tggaactcta ttttctggat aacacatcca    900

ggtggtaaag ccattttgga taaggttgaa gaaaaattgg atttgaagaa agaaaagttt    960

gtagatagta gacatgtttt atctgaacac ggtaacatgt cttcatccac tgtcttgttc   1020

gtaatggatg aattgagaaa gagatcatta gaagagggta aatctactac tggtgacggt   1080

tttgaatggg gtgtcttatt tggtttcggt cctggtttga ccgtcgaaag agtagttgtc   1140

agatcagtac caattaaata tgaaggtaga ggttccttgt taacttgtgg tgacgttgaa   1200
```

```
gaaaacccag gtcctatggc cgtcaagcat ttgatagtat tgaagtttaa agatgaaatc   1260

acagaagctc aaaaggaaga atttttcaag acctacgtta atttggtcaa cattatacct   1320

gctatgaaag atgtatactg ggtaaagac gttacacaaa agaaagaaga aggttataca   1380

cacattgtcg aagtaacctt cgaatcagtt gaaactatcc aagattacat cattcatcca   1440

gctcacgttg gttttggtga cgtttacaga tccttctggg aaaaattgtt gatcttcgat   1500

tacaccccaa gaaagtaccc ttacgatgtt ccagactatg cataagcggc cgc          1553
```

<210> SEQ ID NO 16
<211> LENGTH: 2918
<212> TYPE: DNA
<213> ORGANISM: Artificial Sequence
<220> FEATURE:
<223> OTHER INFORMATION: Codon optimized

<400> SEQUENCE: 16

```
actagtatgg gtttatcatc cgtctgtact ttctccttcc aaactaacta tcatacctta     60

ttgaatcctc acaacaacaa tccaaaaaca tcattgttgt gttacagaca tccaaagaca    120

cctattaagt actcttacaa caactttcca tcaaaacatt gttcaaccaa gtccttccac    180

ttacaaaata agtgctccga aagtttgtct atagctaaga actctatcag agctgcaact    240

acaaatcaaa ctgaaccacc tgaaagtgat aatcactctg ttgccacaaa aattttgaac    300

ttcggtaaag catgttggaa gttgcaaaga ccatacacca taatcgcttt tacttcttgt    360

gcatgcggtt tattcggtaa agaattgttg cataacacta acttaatttc atggtccttg    420

atgttcaagg catttttctt tttagttgcc atcttgtgca tcgcttcatt caccactaca    480

attaatcaaa tatacgattt gcacatcgac agaattaaca aaccagattt gcctttggct    540

tcaggtgaaa tatccgtcaa tactgcatgg atcatgtcta tcatagtagc cttgttcggt    600

ttgatcatca caattaaaat gaagggtggt ccattgtaca tcttcggtta ctgtttcggt    660

atcttcggtg gtattgtcta ttccgtacca cctttagat ggaaacaaaa ccctagtact    720

gcctttttgt tgaatttctt agctcatatc atcacaaact tcaccttcta ctacgcttca    780

agagctgctt taggtttgcc attcgaattg agaccttcat tcacattttt gttggcattc    840

atgaaaagta tgggttctgc attagccttg atcaaggatg cctctgacgt tgaaggtgac    900

acaaagttcg gtattagtac cttggcttct aagtacggtt caagaaattt gactttgttc    960

tgctccggta tcgttttgtt aagttacgtc gcagccattt tggcaggtat catttggcca   1020

caagccttta attctaacgt tatgttgttg tcacatgcca tcttggcttt ctggttgatc   1080

ttgcaaacta gagatttcgc tttgacaaat tatgaccctg aagcaggtag aagattctac   1140

gagtttatgt ggaaattgta ctacgctgaa tatttggtat acgtttttat tgaaggtaga   1200

ggttctttgt tgacctgtgg tgacgttgaa gaaaatccag gtcctatgaa atgttcaact   1260

ttctcctttt ggttcgtatg caagatcatc ttcttttct tttcctttaa catccaaaca   1320

agtatcgcaa acccaagaga aaactttttg aagtgcttct cacaatacat acctaataac   1380

gccaccaatt tgaagttggt ttacactcaa aacaacccat tgtacatgtc cgtcttgaac   1440

agtacaatcc ataatttgag attcacttct gataccactc caaaaccttt ggtcattgta   1500

acccctagtc atgtatctca catccaaggt actatcttat gttctaaaaa ggttggtttg   1560

caaattagaa ctagatccgg tggtcatgat agtgaaggca tgtcatacat ctcccaagtt   1620

ccattcgtta tcgttgattt gagaaacatg agatcaatta aaatagacgt acactcacaa   1680

actgcttggg ttgaagctgg tgcaacattg ggtgaagtat actactgggt taacgaaaag   1740
```

```
aatgaaaact tatcattggc tgctggttac tgtccaacag tttgcgcagg tggtcatttt   1800

ggtggtggtg gttatggtcc tttaatgaga aactacggtt tggccgctga taacataatc   1860

gacgctcatt tggtaaatgt tcacggtaaa gttttggata gaaagtctat gggtgaagac   1920

ttattttggg ctttgagagg tggtggtgca gaatcattcg gtatcatagt tgcttggaag   1980

ataagattag tcgcagtacc aaagtctact atgttctcag tcaaaaagat aatggaaatc   2040

catgaattag ttaaattggt caataagtgg caaaacatcg catacaagta cgataaggac   2100

ttgttgttga tgactcattt catcacaaga aacatcaccg ataaccaagg taaaaataag   2160

actgctatcc acacatactt ttcttcagtt ttcttgggtg gtgtcgattc cttagtagac   2220

ttgatgaata agtcttttcc agaattaggt attaagaaaa ctgattgtag acaattgtct   2280

tggatcgaca ccatcatctt ttattcaggt gttgtcaact acgatacaga caacttcaac   2340

aaagaaatat tattggatag atccgcaggt caaaacggtg cctttaaaat taagttagac   2400

tacgttaaaa agccaatacc tgaatcagtt ttcgtccaaa tcttagaaaa attgtacgaa   2460

gaagatattg gtgcaggcat gtacgccttg tatccatacg gtggtataat ggacgaaatc   2520

agtgaatctg ccattccatt tcctcataga gctggtatct tatacgaatt gtggtacatt   2580

tgttcatggg aaaagcaaga agataacgaa aagcacttaa actggattag aaacatctat   2640

aacttcatga ctccatacgt ttctaaaaac cctagattgg catatttgaa ctacagagat   2700

ttggacatcg gtattaacga tccaaagaat cctaacaact atacccaagc tagaatttgg   2760

ggtgaaaaat acttcggtaa aaatttcgat agattagtaa aggttaagac attggttgac   2820

ccaaacaact tctttagaaa cgaacaatcc attccacctt tacctagaca tagacacgaa   2880

caaaaattaa taagtgaaga agatttgtaa gcggccgc                           2918
```

```
<210> SEQ ID NO 17
<211> LENGTH: 167
<212> TYPE: DNA
<213> ORGANISM: Artificial Sequence
<220> FEATURE:
<223> OTHER INFORMATION: Codon optimized

<400> SEQUENCE: 17

agccaaaata atgataacga gaataatatc aagaatacct tagaacaaca tcgacaacaa     60

caacaggcat tttcggatat gagtcacgtg gagtattcca gaattacaaa attttttcaa    120

gaacaaccac tggagggata taccctttc tctcacaggt ctgcgcc                  167
```

```
<210> SEQ ID NO 18
<211> LENGTH: 1518
<212> TYPE: DNA
<213> ORGANISM: Artificial Sequence
<220> FEATURE:
<223> OTHER INFORMATION: Codon optimized

<400> SEQUENCE: 18

atggtttcca atcacttgtt tgacgcaatg agagccgctg cccctggtaa cgcccctttc     60

ataagaatag ataatactag aacttggaca tacgatgacg cctttgcttt atctggtaga    120

atagcatcag ctatggatgc tttgggtatc agaccaggtg acagagtcgc agttcaagta    180

gaaaaatccg ctgaagcatt gatcttgtat ttggcttgtt tgagaagtgg tgcagtttat    240

ttgccattga atactgccta cacattagct gaattggatt acttcatagg tgacgcagaa    300

cctagattgg ttgtagtcgc ctcttcagcc agagctggtg tagaaacaat tgctaaacca    360
```

```
agaggtgcaa tagtcgaaac cttagatgct gctggttctg gtagtttgtt agatttggcc    420

agagacgaac ctgctgattt tgttgacgct tcaagatcag ccgatgactt agccgctatt    480

ttgtacacct ctggtactac aggtagatca aagggtgcta tgttgactca tggtaatttg    540

ttgtcaaacg cattaacctt gagagatttc tggagagtta ctgccggtga cagattaatc    600

cacgctttgc caatttttca tactcacggt ttattcgttg ctaccaacgt aactttgtta    660

gcaggtgcct ccatgttctt gttgagtaag ttcgatccag aagaaatatt atctttgatg    720

cctcaagcta ctatgttgat gggtgtccca acattctacg ttagattgtt acaatcacct    780

agattagata agcaagctgt tgcaaacatc agattgttta tatccggtag tgctccattg    840

ttagcagaaa cccatactga atttcaagca agaacaggtc acgccatttt agaaagatac    900

ggtatgacag aaaccaatat gaacacttct aacccttatg aaggtaaaag aatagctggt    960

acagttggtt ttccattgcc tgatgtcaca gttagagtaa ccgacccagc cactggttta   1020

gctttgccac ctgaacaaac tggtatgatc gaaattaaag gtccaaacgt ttttaagggt   1080

tactggagaa tgcctgaaaa gactgctgct gagtttactg ctgatggttt ctttatctct   1140

ggtgacttag gtaaaattga tagagacggt tatgtccata ttgttggtcg tggtaaagat   1200

ttggttatat ccggtggtta taacatctac cctaaggaag tagaaggtga aatagatcaa   1260

atcgaaggtg ttgtagaatc agctgtaata ggtgtcccac atcctgattt tggtgaaggt   1320

gttacagcag tcgttgtaag aaaaccaggt gctgcattag atgaaaaggc aattgtttct   1380

gccttacaag acagattggc tagatacaag caaccaaaga gaataatctt cgcagaagat   1440

ttgcctagaa atactatggg taaagtacaa aagaacatct tgagacaaca atacgccgac   1500

ttatacacca gaacctga                                                 1518
```

```
<210> SEQ ID NO 19
<211> LENGTH: 2092
<212> TYPE: DNA
<213> ORGANISM: Artificial Sequence
<220> FEATURE:
<223> OTHER INFORMATION: Codon optimized

<400> SEQUENCE: 19
```

```
actagtatgg gtttatcatc cgtctgtact ttctccttcc aaactaacta tcatacctta     60

ttgaatcctc acaacaacaa tccaaaaaca tcattgttgt gttacagaca tccaaagaca    120

cctattaagt actcttacaa caactttcca tcaaaacatt gttcaaccaa gtccttccac    180

ttacaaaata agtgctccga aagtttgtct atagctaaga actctatcag agctgcaact    240

acaaatcaaa ctgaaccacc tgaaagtgat aatcactctg ttgccacaaa aattttgaac    300

ttcggtaaag catgttggaa gttgcaaaga ccatacacca taatcgcttt tacttcttgt    360

gcatgcggtt tattcggtaa agaattgttg cataacacta acttaatttc atggtcctat    420

gaactgctcc gcattctctt tctggttcgt ctgtaaaata atcttcttct tcttgtcctt    480

caacatccaa atctccatcg caaatccaca agaaaacttt ttgaagtgtt tctccgaata    540

catcccaaac aaccctgcta acccaaagtt tatatatact caacatgatc aattgtacat    600

gtccgttttg aacagtacca tccaaaattt gagattcact tctgacacta caccaaaacc    660

tttagtcatt gttacacctt ccaatgttag tcacattcaa gcttctatat tgtgctctaa    720

gaaagtaggt ttgcaaatca gaactagatc aggtggtcat gatgcagaag gcatgtctta    780

catctcacaa gttccattcg ttgtagtcga tttgagaaat atgcattcca taaagatcga    840

cgttcacagt caaacagcat gggtagaagc aggtgccacc ttgggtgaag tttactactg    900
```

```
gatcaacgaa aagaatgaaa acttttcttt ccctggtggt tactgtccaa cagtaggtgt    960
cggtggtcac ttttctggtg gtggttatgg tgcattgatg agaaactacg gtttagctgc   1020
agataatatt atagacgccc atttggttaa cgtagatggt aaagttttgg acagaaagtc   1080
tatgggtgaa gatttgtttt gggccataag aggtggtggt ggtgaaaatt tcggtatcat   1140
tgccgcttgg aaaattaagt tagtcgctgt tccttccaaa agtactattt tctctgtcaa   1200
aaagaacatg gaaatccacg gtttggttaa gttgtttaat aagtggcaaa acatcgctta   1260
caagtacgat aaggacttgg ttttgatgac ccatttcatc actaaaaata ttacagataa   1320
ccatggtaaa aataagacca ctgttcacgg ttatttttct tcaattttcc atggtggtgt   1380
agattctttg gttgatttga tgaataagtc attcccagaa ttgggtatta aaaagacaga   1440
ttgcaaggaa ttttcttgga tagacacaac catcttctat tcaggtgttg taaacttcaa   1500
caccgctaac ttcaaaaagg aaatcttgtt ggatagatcc gctggtaaaa agaccgcttt   1560
ttctattaaa ttggactacg ttaagaaacc aatccctgaa actgcaatgg tcaagatatt   1620
ggaaaagttg tacgaagaag atgtaggtgt cggcatgtac gttttgtatc catacggtgg   1680
tattatggaa gaaatatctg aatcagccat accatttcct cacagagctg gtatcatgta   1740
tgaattatgg tacacagcct catgggaaaa gcaagaagat aacgaaaagc atatcaactg   1800
ggtcagatcc gtttacaact tcactacacc ttacgttagt caaaacccaa gattggcata   1860
tttgaactac agagatttgg acttaggtaa aactaaccct gaatctccaa ataactatac   1920
acaagcaaga atttggggtg aaaagtactt tggtaaaaat ttcaacagat tagttaaagt   1980
aaagactaaa gccgacccta acaacttttt cagaaacgaa caatccatcc cacctttgcc   2040
acctcaccac cacgaacaaa aattaataag tgaagaagat ttgtaagtcg ac           2092
```

<210> SEQ ID NO 20
<211> LENGTH: 7904
<212> TYPE: DNA
<213> ORGANISM: Artificial Sequence
<220> FEATURE:
<223> OTHER INFORMATION: Codon optimized

<400> SEQUENCE: 20

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatcga ctacgtcgta aggccgtttc tgacagagta aaattcttga gggaactttc    240
accattatgg gaaatggttc aagaaggtat tgacttaaac tccatcaaat ggtcaggtca    300
ttgagtgttt tttatttgtt gtattttttt ttttttagag aaaatcctcc aatatcaaat    360
taggaatcgt agtttcatga ttttctgtta cacctaactt tttgtgtggt gccctcctcc    420
ttgtcaatat taatgttaaa gtgcaattct tttccttat cacgttgagc cattagtatc     480
aatttgctta cctgtattcc tttactatcc tcctttttct ccttcttgat aaatgtatgt    540
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaaccttttt aactgcatct    780
tcaatggcct taccttcttc aggcaagttc aatgacaatt tcaacatcat tgcagcagac    840
```

```
aagatagtgg cgatagggtc aaccttattc tttggcaaat ctggagcaga accgtggcat    900

ggttcgtaca aaccaaatgc ggtgttcttg tctggcaaag aggccaagga cgcagatggc    960

aacaaaccca aggaacctgg gataacggag gcttcatcgg agatgatatc accaaacatg   1020

ttgctggtga ttataatacc atttaggtgg gttgggttct taactaggat catggcggca   1080

gaatcaatca attgatgttg aaccttcaat gtagggaatt cgttcttgat ggtttcctcc   1140

acagtttttc tccataatct tgaagaggcc aaaacattag ctttatccaa ggaccaaata   1200

ggcaatggtg gctcatgttg tagggccatg aaagcggcca ttcttgtgat tctttgcact   1260

tctggaacgg tgtattgttc actatcccaa gcgacaccat caccatcgtc ttcctttctc   1320

ttaccaaagt aaatacctcc cactaattct ctgacaacaa cgaagtcagt acctttagca   1380

aattgtggct tgattggaga taagtctaaa agagagtcgg atgcaaagtt acatggtctt   1440

aagttggcgt acaattgaag ttctttacgg atttttagta aaccttgttc aggtctaaca   1500

ctaccggtac cccatttagg accacccaca gcacctaaca aaacggcatc aaccttcttg   1560

gaggcttcca gcgcctcatc tggaagtggg acacctgtag catcgatagc agcaccacca   1620

attaaatgat tttcgaaatc gaacttgaca ttggaacgaa catcagaaat agctttaaga   1680

accttaatgg cttcggctgt gatttcttga ccaacgtggt cacctggcaa aacgacgatc   1740

ttcttagggg cagacatagg ggcagacatt agaatggtat atccttgaaa tatatatata   1800

tattgctgaa atgtaaaagg taagaaaagt tagaaagtaa gacgattgct aaccacctat   1860

tggaaaaaac aataggtcct taaataatat tgtcaacttc aagtattgtg atgcaagcat   1920

ttagtcatga acgcttctct attctatatg aaaagccggt tccggcctct cacctttcct   1980

ttttctccca atttttcagt tgaaaaaggt atatgcgtca ggcgacctct gaaattaaca   2040

aaaaatttcc agtcatcgaa tttgattctg tgcgatagcg cccctgtgtg ttctcgttat   2100

gttgaggaaa aaaataatgg ttgctaagag attcgaactc ttgcatctta cgatacctga   2160

gtattcccac agttaactgc ggtcaagata tttcttgaat caggcgcctt agaccgctcg   2220

gccaaacaac caattacttg ttgagaaata gagtataatt atcctataaa tataacgttt   2280

ttgaacacac atgaacaagg aagtacagga caattgattt tgaagagaat gtggattttg   2340

atgtaattgt tgggattcca tttttaataa ggcaataata ttaggtatgt ggatatacta   2400

gaagttctcc tcgagggtcg atatgcggtg tgaaataccg cacagatgcg taaggagaaa   2460

ataccgcatc aggaaattgt aaacgttaat attttgttaa aattcgcgtt aaatttttgt   2520

taaatcagct catttttaa ccaataggcc gaaatcggca aaatccctta taaatcaaaa   2580

gaatagaccg agatagggtt gagtgttgtt ccagtttgga acaagagtcc actattaaag   2640

aacgtggact ccaacgtcaa agggcgaaaa accgtctatc agggcgatgg cccactacgt   2700

gaaccatcac cctaatcaag ttttttgggg tcgaggtgcc gtaaagcact aaatcggaac   2760

cctaaaggga gcccccgatt tagagcttga cggggaaagc cggcgaacgt ggcgagaaag   2820

gaagggaaga aagcgaaagg agcgggcgct agggcgctgg caagtgtagc ggtcacgctg   2880

cgcgtaacca ccacacccgc cgcgcttaat gcgccgctac agggcgcgtc gcgccattcg   2940

ccattcaggc tgcgcaactg ttgggaaggg cgatcggtgc gggcctcttc gctattacgc   3000

cagctggcga aggggggatg tgctgcaagg cgattaagtt gggtaacgcc agggttttcc   3060

cagtcacgac gttgtaaaac gacggccagt gaattgtaat acgactcact atagggcgaa   3120

ttggagctct agtacggatt agaagccgcc gagcgggcga cagccctccg acggaagact   3180

ctcctccgtg cgtcctcgtc ttcaccggtc gcgttcctga aacgcagatg tgcctcgcgc   3240
```

```
cgcactgctc cgaacaataa agattctaca atactagctt ttatggttat gaagaggaaa   3300

aattggcagt aacctggccc cacaaacctt caaattaacg aatcaaatta acaaccatag   3360

gatgataatg cgattagttt tttagcctta tttctggggt aattaatcag cgaagcgatg   3420

atttttgatc tattaacaga tatataaatg gaaaagctgc ataaccactt taactaatac   3480

tttcaacatt ttcagtttgt attacttctt attcaaatgt cataaaagta tcaacaaaaa   3540

attgttaata tacctctata ctttaacgtc aaggagaaaa aaccccggat tctagaacta   3600

gtggatcccc catcacaagt ttgtacaaaa aagctgaacg agaaacgtaa aatgatataa   3660

atatcaatat attaaattag attttgcata aaaaacagac tacataatac tgtaaaacac   3720

aacatatcca gtcactatgg cggccgcatt aggcacccca ggctttacac tttatgcttc   3780

cggctcgtat aatgtgtgga ttttgagtta ggatccgtcg agattttcag gagctaagga   3840

agctaaaatg gagaaaaaaa tcactggata taccaccgtt gatatatccc aatggcatcg   3900

taaagaacat tttgaggcat ttcagtcagt tgctcaatgt acctataacc agaccgttca   3960

gctggatatt acggcctttt taaagaccgt aaagaaaaat aagcacaagt tttatccggc   4020

ctttattcac attcttgccc gcctgatgaa tgctcatccg gaattccgta tggcaatgaa   4080

agacggtgag ctggtgatat gggatagtgt tcacccttgt tacaccgttt tccatgagca   4140

aactgaaacg ttttcatcgc tctggagtga ataccacgac gatttccggc agtttctaca   4200

catatattcg caagatgtgg cgtgttacgg tgaaaacctg gcctatttcc ctaaagggtt   4260

tattgagaat atgtttttcg tctcagccaa tccctgggtg agtttcacca gttttgattt   4320

aaacgtggcc aatatggaca acttcttcgc ccccgttttc accatgggca aatattatac   4380

gcaaggcgac aaggtgctga tgccgctggc gattcaggtt catcatgccg tctgtgatgg   4440

cttccatgtc ggcagaatgc ttaatgaatt acaacagtac tgcgatgagt ggcagggcgg   4500

ggcgtaaacg ccgcgtggat ccggcttact aaaagccaga taacagtatg cgtatttgcg   4560

cgctgatttt tgcggtataa gaatatatac tgatatgtat acccgaagta tgtcaaaaag   4620

aggtatgcta tgaagcagcg tattacagtg acagttgaca gcgacagcta tcagttgctc   4680

aaggcatata tgatgtcaat atctccggtc tggtaagcac aaccatgcag aatgaagccc   4740

gtcgtctgcg tgccgaacgc tggaaagcgg aaaatcagga agggatggct gaggtcgccc   4800

ggtttattga aatgaacggc tcttttgctg acgagaacag gggctggtga aatgcagttt   4860

aaggtttaca cctataaaag agagagccgt tatcgtctgt ttgtggatgt acagagtgat   4920

attattgaca cgcccgggcg acggatggtg atccccctgg ccagtgcacg tctgctgtca   4980

gataaagtct cccgtgaact ttacccggtg gtgcatatcg gggatgaaag ctggcgcatg   5040

atgaccaccg atatggccag tgtgccggtc tccgttatcg gggaagaagt ggctgatctc   5100

agccaccgcg aaaatgacat caaaaacgcc attaacctga tgttctgggg aatataaatg   5160

tcaggctccc ttatacacag ccagtctgca ggtcgaccat agtgactgga tatgttgtgt   5220

tttacagtat tatgtagtct gtttttttatg caaaatctaa tttaatatat tgatatttat   5280

atcattttac gtttctcgtt cagctttctt gtacaaagtg gtgatgggct gcaggaattc   5340

gatatcaagc ttatcgatac cgtcgacctc gagtcatgta attagttatg tcacgcttac   5400

attcacgccc tccccccaca tccgctctaa ccgaaaagga aggagttaga caacctgaag   5460

tctaggtccc tatttatttt tttatagtta tgttagtatt aagaacgtta tttatatttc   5520

aaatttttct tttttttctg tacagacgcg tgtacgcatg taacattata ctgaaaacct   5580
```

-continued

```
tgcttgagaa ggttttggga cgctcgaagg ctttaatttg cggccggtac ccagcttttg   5640
ttccctttag tgagggttaa ttccgagctt ggcgtaatca tggtcatagc tgtttcctgt   5700
gtgaaattgt tatccgctca caattccaca caacatagga gccggaagca taaagtgtaa   5760
agcctggggt gcctaatgag tgaggtaact cacattaatt gcgttgcgct cactgcccgc   5820
tttccagtcg ggaaacctgt cgtgccagct gcattaatga atcggccaac gcgcggggag   5880
aggcggtttg cgtattgggc gctcttccgc ttcctcgctc actgactcgc tgcgctcggt   5940
cgttcggctg cggcgagcgg tatcagctca ctcaaaggcg gtaatacggt tatccacaga   6000
atcaggggat aacgcaggaa agaacatgtg agcaaaaggc cagcaaaagg ccaggaaccg   6060
taaaaaggcc gcgttgctgg cgtttttcca taggctcggc ccccctgacg agcatcacaa   6120
aaatcgacgc tcaagtcaga ggtggcgaaa cccgacagga ctataaagat accaggcgtt   6180
ccccctgga agctccctcg tgcgctctcc tgttccgacc ctgccgctta ccggatacct   6240
gtccgccttt ctcccttcgg gaagcgtggc gctttctcaa tgctcacgct gtaggtatct   6300
cagttcggtg taggtcgttc gctccaagct gggctgtgtg cacgaacccc ccgttcagcc   6360
cgaccgctgc gccttatccg gtaactatcg tcttgagtcc aacccggtaa gacacgactt   6420
atcgccactg gcagcagcca ctggtaacag gattagcaga gcgaggtatg taggcggtgc   6480
tacagagttc ttgaagtggt ggcctaacta cggctacact agaaggacag tatttggtat   6540
ctgcgctctg ctgaagccag ttaccttcgg aaaaagagtt ggtagctctt gatccggcaa   6600
acaaaccacc gctggtagcg gtggtttttt tgtttgcaag cagcagatta cgcgcagaaa   6660
aaaaggatct caagaagatc ctttgatctt ttctacgggg tctgacgctc agtggaacga   6720
aaactcacgt taagggattt tggtcatgag attatcaaaa aggatcttca cctagatcct   6780
tttaaattaa aaatgaagtt ttaaatcaat ctaaagtata tatgagtaaa cttggtctga   6840
cagttaccaa tgcttaatca gtgaggcacc tatctcagcg atctgtctat ttcgttcatc   6900
catagttgcc tgactgcccg tcgtgtagat aactacgata cgggagggct taccatctgg   6960
ccccagtgct gcaatgatac cgcgagaccc acgctcaccg gctccagatt tatcagcaat   7020
aaaccagcca gccggaaggg ccgagcgcag aagtggtcct gcaactttat ccgcctccat   7080
ccagtctatt aattgttgcc gggaagctag agtaagtagt tcgccagtta atagtttgcg   7140
caacgttgtt gccattgcta caggcatcgt ggtgtcacgc tcgtcgtttg gtatggcttc   7200
attcagctcc ggttcccaac gatcaaggcg agttacatga tcccccatgt tgtgaaaaaa   7260
agcggttagc tccttcggtc ctccgatcgt tgtcagaagt aagttggccg cagtgttatc   7320
actcatggtt atggcagcac tgcataattc tcttactgtc atgccatccg taagatgctt   7380
ttctgtgact ggtgagtact caaccaagtc attctgagaa tagtgtatgc ggcgaccgag   7440
ttgctcttgc ccggcgtcaa tacgggataa taccgcgcca catagcagaa ctttaaaagt   7500
gctcatcatt ggaaaacgtt cttcggggcg aaaactctca aggatcttac cgctgttgag   7560
atccagttcg atgtaaccca ctcgtgcacc caactgatct tcagcatctt ttactttcac   7620
cagcgtttct gggtgagcaa aaacaggaag gcaaaatgcc gcaaaaaagg gaataagggc   7680
gacacggaaa tgttgaatac tcatactctt cctttttcaa tattattgaa gcatttatca   7740
gggttattgt ctcatgagcg gatacatatt tgaatgtatt tagaaaaata aacaaatagg   7800
ggttccgcgc acatttcccc gaaaagtgcc acctgacgtc taagaaacca ttattatcat   7860
gacattaacc tataaaaata ggcgtatcac gaggcccttt cgtc                    7904
```

<210> SEQ ID NO 21
<211> LENGTH: 6773
<212> TYPE: DNA
<213> ORGANISM: Artificial Sequence
<220> FEATURE:
<223> OTHER INFORMATION: Codon optimized

<400> SEQUENCE: 21
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc tttttttga tttcggtttc 240 tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc attttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa agggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100

-continued

```
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcacaagtt tgtacaaaaa agctgaacga gaaacgtaaa   2520
atgatataaa tatcaatata ttaaattaga ttttgcataa aaaacagact acataatact   2580
gtaaaacaca acatatccag tcactatggc ggccgcatta ggcaccccag gctttacact   2640
ttatgcttcc ggctcgtata atgtgtggat tttgagttag gatccgtcga gattttcagg   2700
agctaaggaa gctaaaatgg agaaaaaaat cactggatat accaccgttg atatatccca   2760
atggcatcgt aaagaacatt ttgaggcatt tcagtcagtt gctcaatgta cctataacca   2820
gaccgttcag ctggatatta cggccttttt aaagaccgta aagaaaaata agcacaagtt   2880
ttatccggcc tttattcaca ttcttgcccg cctgatgaat gctcatccgg aattccgtat   2940
ggcaatgaaa gacggtgagc tggtgatatg ggatagtgtt cacccttgtt acaccgtttt   3000
ccatgagcaa actgaaacgt tttcatcgct ctggagtgaa taccacgacg atttccggca   3060
gtttctacac atatattcgc aagatgtggc gtgttacggt gaaaacctgg cctatttccc   3120
taaagggttt attgagaata tgtttttcgt ctcagccaat ccctgggtga gtttcaccag   3180
ttttgattta aacgtggcca atatggacaa cttcttcgcc cccgttttca ccatgggcaa   3240
atattatacg caaggcgaca aggtgctgat gccgctggcg attcaggttc atcatgccgt   3300
ctgtgatggc ttccatgtcg gcagaatgct taatgaatta caacagtact gcgatgagtg   3360
gcagggcggg gcgtaaacgc cgcgtggatc cggcttacta aaagccagat aacagtatgc   3420
gtatttgcgc gctgattttt gcggtataag aatatatact gatatgtata cccgaagtat   3480
gtcaaaaaga ggtatgctat gaagcagcgt attacagtga cagttgacag cgacagctat   3540
cagttgctca aggcatatat gatgtcaata tctccggtct ggtaagcaca accatgcaga   3600
atgaagcccg tcgtctgcgt gccgaacgct ggaaagcgga aaatcaggaa gggatggctg   3660
aggtcgcccg gtttattgaa atgaacggct cttttgctga cgagaacagg ggctggtgaa   3720
atgcagttta aggtttacac ctataaaaga gagagccgtt atcgtctgtt tgtggatgta   3780
cagagtgata ttattgacac gcccgggcga cggatggtga tccccctggc cagtgcacgt   3840
ctgctgtcag ataaagtctc ccgtgaactt tacccggtgg tgcatatcgg ggatgaaagc   3900
tggcgcatga tgaccaccga tatggccagt gtgccggtct ccgttatcgg ggaagaagtg   3960
gctgatctca gccaccgcga aaatgacatc aaaaacgcca ttaacctgat gttctgggga   4020
atataaatgt caggctccct tatacacagc cagtctgcag gtcgaccata gtgactggat   4080
atgttgtgtt ttacagtatt atgtagtctg ttttttatgc aaaatctaat ttaatatatt   4140
gatatttata tcattttacg tttctcgttc agctttcttg tacaaagtgg tgatgggctg   4200
caggaattcg atatcaagct tatcgatacc gtcgacctcg agtcatgtaa ttagttatgt   4260
cacgcttaca ttcacgccct ccccccacat ccgctctaac cgaaaaggaa ggagttagac   4320
aacctgaagt ctaggtccct atttattttt ttatagttat gttagtatta agaacgttat   4380
ttatatttca aatttttctt ttttttctgt acagacgcgt gtacgcatgt aacattatac   4440
tgaaaacctt gcttgagaag gttttgggac gctcgaaggc tttaatttgc ggccggtacc   4500
```

```
cagcttttgt tccctttagt gagggttaat tccgagcttg gcgtaatcat ggtcatagct   4560
gtttcctgtg tgaaattgtt atccgctcac aattccacac aacataggag ccggaagcat   4620
aaagtgtaaa gcctggggtg cctaatgagt gaggtaactc acattaattg cgttgcgctc   4680
actgcccgct ttccagtcgg gaaacctgtc gtgccagctg cattaatgaa tcggccaacg   4740
cgcggggaga ggcggtttgc gtattgggcg ctcttccgct tcctcgctca ctgactcgct   4800
gcgctcggtc gttcggctgc ggcgagcggt atcagctcac tcaaaggcgg taatacggtt   4860
atccacagaa tcaggggata acgcaggaaa gaacatgtga gcaaaaggcc agcaaaaggc   4920
caggaaccgt aaaaaggccg cgttgctggc gtttttccat aggctcggcc cccctgacga   4980
gcatcacaaa aatcgacgct caagtcagag gtggcgaaac ccgacaggac tataaagata   5040
ccaggcgttc ccccctggaa gctccctcgt gcgctctcct gttccgaccc tgccgcttac   5100
cggatacctg tccgcctttc tcccttcggg aagcgtggcg ctttctcaat gctcacgctg   5160
taggtatctc agttcggtgt aggtcgttcg ctccaagctg ggctgtgtgc acgaaccccc   5220
cgttcagccc gaccgctgcg ccttatccgg taactatcgt cttgagtcca acccggtaag   5280
acacgactta tcgccactgg cagcagccac tggtaacagg attagcagag cgaggtatgt   5340
aggcggtgct acagagttct tgaagtggtg gcctaactac ggctacacta gaaggacagt   5400
atttggtatc tgcgctctgc tgaagccagt taccttcgga aaaagagttg gtagctcttg   5460
atccggcaaa caaaccaccg ctggtagcgg tggttttttt gtttgcaagc agcagattac   5520
gcgcagaaaa aaaggatctc aagaagatcc tttgatcttt tctacggggt ctgacgctca   5580
gtggaacgaa aactcacgtt aagggatttt ggtcatgaga ttatcaaaaa ggatcttcac   5640
ctagatcctt ttaaattaaa aatgaagttt taaatcaatc taaagtatat atgagtaaac   5700
ttggtctgac agttaccaat gcttaatcag tgaggcacct atctcagcga tctgtctatt   5760
tcgttcatcc atagttgcct gactgcccgt cgtgtagata actacgatac gggagggctt   5820
accatctggc cccagtgctg caatgatacc gcgagaccca cgctcaccgg ctccagattt   5880
atcagcaata aaccagccag ccggaagggc cgagcgcaga agtggtcctg caactttatc   5940
cgcctccatc cagtctatta attgttgccg ggaagctaga gtaagtagtt cgccagttaa   6000
tagtttgcgc aacgttgttg ccattgctac aggcatcgtg gtgtcacgct cgtcgtttgg   6060
tatggcttca ttcagctccg gttcccaacg atcaaggcga gttacatgat cccccatgtt   6120
gtgaaaaaaa gcggttagct ccttcggtcc tccgatcgtt gtcagaagta agttggccgc   6180
agtgttatca ctcatggtta tggcagcact gcataattct cttactgtca tgccatccgt   6240
aagatgcttt tctgtgactg gtgagtactc aaccaagtca ttctgagaat agtgtatgcg   6300
gcgaccgagt tgctcttgcc cggcgtcaat acgggataat accgcgccac atagcagaac   6360
tttaaaagtg ctcatcattg gaaaacgttc ttcggggcga aaactctcaa ggatcttacc   6420
gctgttgaga tccagttcga tgtaacccac tcgtgcaccc aactgatctt cagcatcttt   6480
tactttcacc agcgtttctg ggtgagcaaa aacaggaagg caaaatgccg caaaaaaggg   6540
aataagggcg acacggaaat gttgaatact catactcttc ctttttcaat attattgaag   6600
catttatcag ggttattgtc tcatgagcgg atacatattt gaatgtattt agaaaaataa   6660
acaaataggg gttccgcgca catttccccg aaaagtgcca cctgacgtct aagaaaccat   6720
tattatcatg acattaacct ataaaaatag gcgtatcacg aggccctttc gtc          6773
```

<210> SEQ ID NO 22

<211> LENGTH: 7690
<212> TYPE: DNA
<213> ORGANISM: Artificial Sequence
<220> FEATURE:
<223> OTHER INFORMATION: Codon optimized

<400> SEQUENCE: 22

```
ttatcatgac attaacctat aaaaataggc gtatcacgag gccctttcgt ctcgcgcgtt     60
tcggtgatga cggtgaaaac ctctgacaca tgcagctccc ggagacggtc acagcttgtc    120
tgtaagcgga tgccgggagc agacaagccc gtcagggcgc gtcagcgggt gttggcgggt    180
gtcggggctg gcttaactat gcggcatcag agcagattgt actgagagtg caccacgctt    240
ttcaattcaa ttcatcattt ttttttattc ttttttttg atttcggttt ctttgaaatt    300
tttttgattc ggtaatctcc gaacagaagg aagaacgaag gaaggagcac agacttagat    360
tggtatatat acgcatatgt agtgttgaag aaacatgaaa ttgcccagta ttcttaaccc    420
aactgcacag aacaaaaacc tgcaggaaac gaagataaat catgtcgaaa gctacatata    480
aggaacgtgc tgctactcat cctagtcctg ttgctgccaa gctatttaat atcatgcacg    540
aaaagcaaac aaacttgtgt gcttcattgg atgttcgtac caccaaggaa ttactggagt    600
tagttgaagc attaggtccc aaaatttgtt tactaaaaac acatgtggat atcttgactg    660
atttttccat ggagggcaca gttaagccgc taaaggcatt atccgccaag tacaattttt    720
tactcttcga agacagaaaa tttgctgaca ttggtaatac agtcaaattg cagtactctg    780
cgggtgtata cagaatagca gaatgggcag acattacgaa tgcacacggt gtggtgggcc    840
caggtattgt tagcggtttg aagcaggcgg cagaagaagt aacaaaggaa cctagaggcc    900
ttttgatgtt agcagaattg tcatgcaagg gctccctatc tactggagaa tatactaagg    960
gtactgttga cattgcgaag agcgacaaag attttgttat cggctttatt gctcaaagag   1020
acatgggtgg aagagatgaa ggttacgatt ggttgattat gacacccggt gtgggtttag   1080
atgacaaggg agacgcattg ggtcaacagt atagaaccgt ggatgatgtg gtctctacag   1140
gatctgacat tattattgtt ggaagaggac tatttgcaaa gggaagggat gctaaggtag   1200
agggtgaacg ttacagaaaa gcaggctggg aagcatattt gagaagatgc ggccagcaaa   1260
actaaaaaac tgtattataa gtaaatgcat gtatactaaa ctcacaaatt agagcttcaa   1320
tttaattata tcagttatta ccctgcggtg tgaaataccg cacagatgcg taaggagaaa   1380
ataccgcatc aggaaattgt aaacgttaat attttgttaa aattcgcgtt aaatttttgt   1440
taaatcagct catttttaa ccaataggcc gaaatcggca aaatccctta taaatcaaaa   1500
gaatagaccg agatagggtt gagtgttgtt ccagtttgga acaagagtcc actattaaag   1560
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gcccccgatt tagagcttga cggggaaagc cggcgaacgt ggcgagaaag   1740
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga aggggggatg tgctgcaagg cgattaagtt gggtaacgcc agggttttcc   1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga aacgcagatg tgcctcgcgc   2160
```

```
cgcactgctc cgaacaataa agattctaca atactagctt ttatggttat gaagaggaaa   2220
aattggcagt aacctggccc cacaaacctt caaattaacg aatcaaatta acaaccatag   2280
gatgataatg cgattagttt tttagcctta tttctggggt aattaatcag cgaagcgatg   2340
atttttgatc tattaacaga tatataaatg gaaaagctgc ataaccactt taactaatac   2400
tttcaacatt ttcagtttgt attacttctt attcaaatgt cataaaagta tcaacaaaaa   2460
attgttaata tacctctata ctttaacgtc aaggagaaaa aaccccggat tctagaacta   2520
gtggatcccc catcatggtt tccaatcact tgtttgacgc aatgagagcc gctgcccctg   2580
gtaacgcccc tttcataaga atagataata ctagaacttg gacatacgat gacgcctttg   2640
ctttatctgg tagaatagca tcagctatgg atgctttggg tatcagacca ggtgacagag   2700
tcgcagttca agtagaaaaa tccgctgaag cattgatctt gtatttggct tgtttgagaa   2760
gtggtgcagt ttatttgcca ttgaatactg cctacacatt agctgaattg gattacttca   2820
taggtgacgc agaacctaga ttggttgtag tcgcctcttc agccagagct ggtgtagaaa   2880
caattgctaa accaagaggt gcaatagtcg aaaccttaga tgctgctggt tctggtagtt   2940
tgttagattt ggccagagac gaacctgctg attttgttga cgcttcaaga tcagccgatg   3000
acttagccgc tattttgtac acctctggta ctacaggtag atcaaagggt gctatgttga   3060
ctcatggtaa tttgttgtca aacgcattaa ccttgagaga tttctggaga gttactgccg   3120
gtgacagatt aatccacgct ttgccaattt ttcatactca cggtttattc gttgctacca   3180
acgtaacttt gttagcaggt gcctccatgt tcttgttgag taagttcgat ccagaagaaa   3240
tattatcttt gatgcctcaa gctactatgt tgatgggtgt cccaacattc tacgttagat   3300
tgttacaatc acctagatta gataagcaag ctgttgcaaa catcagattg tttatatccg   3360
gtagtgctcc attgttagca gaaacccata ctgaatttca agcaagaaca ggtcacgcca   3420
ttttagaaag atacggtatg acagaaacca atatgaacac ttctaaccct tatgaaggta   3480
aaagaatagc tggtacagtt ggttttccat tgcctgatgt cacagttaga gtaaccgacc   3540
cagccactgg tttagctttg ccacctgaac aaactggtat gatcgaaatt aaaggtccaa   3600
acgtttttaa gggttactgg agaatgcctg aaaagactgc tgctgagttt actgctgatg   3660
gtttctttat ctctggtgac ttaggtaaaa ttgatagaga cggttatgtc catattgttg   3720
gtcgtggtaa agatttggtt atatccggtg gttataacat ctaccctaag gaagtagaag   3780
gtgaaataga tcaaatcgaa ggtgttgtag aatcagctgt aataggtgtc ccacatcctg   3840
attttggtga aggtgttaca gcagtcgttg taagaaaacc aggtgctgca ttagatgaaa   3900
aggcaattgt ttctgcctta caagacagat tggctagata caagcaacca aagagaataa   3960
tcttcgcaga agatttgcct agaaatacta tgggtaaagt acaaaagaac atcttgagac   4020
aacaatacgc cgacttatac accagaaccg aaggtagagg ttctttgtta acatgtggtg   4080
acgttgaaga aaatccaggt cctatggctt cagaaaagga aataagaaga gaaagattct   4140
tgaacgtatt cccaaagtta gttgaagaat tgaacgctag tttgttagct tatggtatgc   4200
ctaaagaagc ctgcgattgg tatgctcact ctttaaacta caatactcca ggtggtaaat   4260
tgaatagagg tttgagtgta gttgatactt atgctatctt gtctaacaaa accgttgaac   4320
aattaggtca agaagaatac gaaaaggtcg ctatcttggg ttggtgtatt gaattgttgc   4380
aagcatactt tttggttgcc gatgacatga tggataagtc tataacaaga agaggtcaac   4440
catgctggta caaagttcca gaagttggtg aaatagccat aaatgatgct tttatgttgg   4500
```

```
aagccgctat ctataaattg ttgaagtcac atttcagaaa cgaaaagtac tacatcgata   4560
ttaccgaatt attccacgaa gttactttcc aaacagaatt gggtcaattg atggatttga   4620
taactgcacc tgaagataaa gttgacttgt caaagttttc cttgaagaaa cattcattca   4680
tcgtcacctt tgaaactgct tattactcct tctatttgcc agtcgccttg gctatgtacg   4740
tagctggtat tactgatgaa aaagacttga agcaagcaag agatgttttg atacctttgg   4800
gtgaatactt ccaaatccaa gatgactact tagactgttt cggtactcca gaacaaatag   4860
gtaaaatcgg tacagatatt caagacaata agtgcagttg ggttattaac aaggctttgg   4920
aattagcatc tgccgaacaa agaaagactt tggatgaaaa ctacggtaaa aaggactcag   4980
ttgctgaagc aaagtgtaag aaaattttta atgatttgaa gattgaacaa ttgtaccatg   5040
aatacgaaga atccatcgct aaagacttaa aggcaaagat tagtcaagtt gatgaatcaa   5100
gaggttttaa agccgacgtt ttgacagctt tcttgaataa ggtctacaag agatcaaagt   5160
gatgggctgc aggaattcga tatcaagctt atcgataccg tcgacctcga gtcatgtaat   5220
tagttatgtc acgcttacat tcacgccctc cccccacatc cgctctaacc gaaaaggaag   5280
gagttagaca acctgaagtc taggtcccta tttatttttt tatagttatg ttagtattaa   5340
gaacgttatt tatatttcaa atttttcttt tttttctgta cagacgcgtg tacgcatgta   5400
acattatact gaaaaccttg cttgagaagg ttttgggacg ctcgaaggct ttaatttgcg   5460
gccggtaccc agcttttgtt ccctttagtg agggttaatt ccgagcttgg cgtaatcatg   5520
gtcatagctg tttcctgtgt gaaattgtta tccgctcaca attccacaca acataggagc   5580
cggaagcata aagtgtaaag cctggggtgc ctaatgagtg aggtaactca cattaattgc   5640
gttgcgctca ctgcccgctt tccagtcggg aaacctgtcg tgccagctgc attaatgaat   5700
cggccaacgc gcggggagag gcggtttgcg tattgggcgc tcttccgctt cctcgctcac   5760
tgactcgctg cgctcggtcg ttcggctgcg gcgagcggta tcagctcact caaaggcggt   5820
aatacggtta tccacagaat caggggataa cgcaggaaag aacatgtgag caaaaggcca   5880
gcaaaaggcc aggaaccgta aaaaggccgc gttgctggcg tttttccata ggctcggccc   5940
ccctgacgag catcacaaaa atcgacgctc aagtcagagg tggcgaaacc cgacaggact   6000
ataaagatac caggcgttcc ccccctggaag ctccctcgtg cgctctcctg ttccgaccct   6060
gccgcttacc ggatacctgt ccgcctttct cccttcggga agcgtggcgc tttctcaatg   6120
ctcacgctgt aggtatctca gttcggtgta ggtcgttcgc tccaagctgg gctgtgtgca   6180
cgaacccccc gttcagcccg accgctgcgc cttatccggt aactatcgtc ttgagtccaa   6240
cccggtaaga cacgacttat cgccactggc agcagccact ggtaacagga ttagcagagc   6300
gaggtatgta ggcggtgcta cagagttctt gaagtggtgg cctaactacg gctacactag   6360
aaggacagta tttggtatct gcgctctgct gaagccagtt accttcggaa aaagagttgg   6420
tagctcttga tccggcaaac aaaccaccgc tggtagcggt ggtttttttg tttgcaagca   6480
gcagattacg cgcagaaaaa aaggatctca agaagatcct ttgatctttt ctacggggtc   6540
tgacgctcag tggaacgaaa actcacgtta agggattttg gtcatgagat tatcaaaaag   6600
gatcttcacc tagatccttt taaattaaaa atgaagtttt aaatcaatct aaagtatata   6660
tgagtaaact tggtctgaca gttaccaatg cttaatcagt gaggcaccta tctcagcgat   6720
ctgtctattt cgttcatcca tagttgcctg actgcccgtc gtgtagataa ctacgatacg   6780
ggagggctta ccatctggcc ccagtgctgc aatgataccg cgagacccac gctcaccggc   6840
tccagattta tcagcaataa accagccagc cggaagggcc gagcgcagaa gtggtcctgc   6900
```

```
aactttatcc gcctccatcc agtctattaa ttgttgccgg gaagctagag taagtagttc   6960

gccagttaat agtttgcgca acgttgttgc cattgctaca ggcatcgtgg tgtcacgctc   7020

gtcgtttggt atggcttcat tcagctccgg ttcccaacga tcaaggcgag ttacatgatc   7080

ccccatgttg tgaaaaaaag cggttagctc cttcggtcct ccgatcgttg tcagaagtaa   7140

gttggccgca gtgttatcac tcatggttat ggcagcactg cataattctc ttactgtcat   7200

gccatccgta agatgctttt ctgtgactgg tgagtactca accaagtcat tctgagaata   7260

gtgtatgcgg cgaccgagtt gctcttgccc ggcgtcaata cgggataata ccgcgccaca   7320

tagcagaact ttaaaagtgc tcatcattgg aaaacgttct tcggggcgaa aactctcaag   7380

gatcttaccg ctgttgagat ccagttcgat gtaacccact cgtgcaccca actgatcttc   7440

agcatctttt actttcacca gcgtttctgg gtgagcaaaa acaggaaggc aaaatgccgc   7500

aaaaaaggga ataagggcga cacggaaatg ttgaatactc atactcttcc tttttcaata   7560

ttattgaagc atttatcagg gttattgtct catgagcgga tacatatttg aatgtattta   7620

gaaaaataaa caaatagggg ttccgcgcac atttccccga aaagtgccac ctgacgtcta   7680

agaaaccatt                                                          7690
```

```
<210> SEQ ID NO 23
<211> LENGTH: 2163
<212> TYPE: DNA
<213> ORGANISM: Artificial Sequence
<220> FEATURE:
<223> OTHER INFORMATION: Codon optimized

<400> SEQUENCE: 23

atgggtaaaa actataagtc cttggattca gtcgttgcct cagatttcat cgcattgggt     60

atcacctcag aagtagcaga aacattacat ggtagattgg cagaaatcgt ttgtaattat    120

ggtgctgcaa cccctcaaac ttggatcaac atcgctaacc atatcttgtc accagatttg    180

cctttctcct tacaccaaat gttgttttat ggttgctaca aggatttcgg tccagcccca    240

cctgcttgga ttccagaccc tgaaaaagtc aagtcaacta atttgggtgc tttgttggaa    300

aagagaggta aagaattttt gggtgtaaag tacaaagatc caatttcttc tttttctcac    360

ttccaagaat tttctgttag aaaccctgaa gtctattgga gaacagtatt gatggatgaa    420

atgaaaatta gtttctctaa ggacccagaa tgtatcttga gaagagatga catcaacaac    480

ccaggtggtt ctgaatggtt acctggtggt tacttgaact cagctaaaaa ttgcttgaac    540

gtaaactcca ataagaaatt gaacgatact atgatcgttt ggagagacga gggtaacgat    600

gacttgcctt tgaataagtt gacattagat caattgagaa agagagtttg gttggttggt    660

tatgcattgg aagaaatggg tttagaaaaa ggttgtgcaa tagccatcga tatgccaatg    720

catgttgatg ctgttgttat atatttggcc atagtattgg ctggttacgt agttgtctct    780

atagcagatt cattttccgc ccctgaaatc tcaactagat tgagattatc caaagctaag    840

gcaattttca cacaagatca catcatcaga ggtaaaaaga gaataccatt gtattcaaga    900

gtagttgaag ctaaatcccc aatggcaata gttatccctt gtagtggttc taacattggt    960

gcagaattga gagatggtga catatcttgg gattactttt tagaaagagc caaggagttt   1020

aaaaactgcg agtttactgc cagagaacaa cctgttgatg cttatactaa catcttattc   1080

tccagtggta ctacaggtga accaaaagca attccttgga cacaagccac cccattgaag   1140

gctgctgctg atggttggtc tcatttggat attagaaaag gtgacgttat agtatggcca   1200
```

```
actaatttgg gttggatgat gggtccttgg ttggtttatg ctagtttgtt aaatggtgca   1260
tctattgcct tgtacaacgg tagtccttta gtctctggtt tcgctaaatt tgttcaagat   1320
gcaaaggtca caatgttggg tgtcgtacca tctattgtaa gatcatggaa atccacaaat   1380
tgtgtttcag gttacgattg gtccaccata agatgctttt cttcatccgg tgaagcctct   1440
aatgtagacg aatatttgtg gttaatgggt agagctaact acaagccagt tatagaaatg   1500
tgtggtggta cagaaatcgg tggtgctttt tctgctggtt catttttgca agctcaatct   1560
ttaagttctt tttcatccca atgtatgggt tgcaccttgt acatattaga taagaacggt   1620
tacccaatgc ctaaaaataa gccaggtatc ggtgaattgg cattaggtcc tgttatgttt   1680
ggtgcctcaa aacattgtt aaacggtaat catcacgatg tctatttcaa gggtatgcca   1740
accttgaatg gtgaagtatt gagaagacat ggtgacattt tcgaattgac ctctaacggt   1800
tactaccatg cacacggtag agccgatgac actatgaaca tcggtggtat caaaattagt   1860
tctatcgaaa tcgaaagagt ctgtaatgaa gtagatgaca gagtttttga aaccactgct   1920
attggtgttc cacctttggg tggtggtcca gaacaattgg tcatattttt cgtattgaag   1980
gattcaaacg acacaaccat tgatttgaac caattgagat tatcctttaa cttgggtttg   2040
caaaagaaat tgaacccatt attcaaagtt actagagttg tcccattgtc atccttacct   2100
agaactgcaa caaacaagat catgagaaga gttttgagac aacaattcag tcatttcgaa   2160
tga                                                                  2163
```

<210> SEQ ID NO 24
<211> LENGTH: 1059
<212> TYPE: DNA
<213> ORGANISM: Artificial Sequence
<220> FEATURE:
<223> OTHER INFORMATION: Codon optimized

<400> SEQUENCE: 24

```
atggcttcag aaaaggaaat aagaagagaa agattcttga acgtattccc aaagttagtt     60
gaagaattga acgctagttt gttagcttat ggtatgccta aagaagcctg cgattggtat    120
gctcactctt taaactacaa tactccaggt ggtaaattga atagaggttt gagtgtagtt    180
gatacttatg ctatcttgtc taacaaaacc gttgaacaat taggtcaaga agaatacgaa    240
aaggtcgcta tcttgggttg gtgtattgaa ttgttgcaag catacttttt ggttgccgat    300
gacatgatgg ataagtctat aacaagaaga ggtcaaccat gctggtacaa agttccagaa    360
gttggtgaaa tagccataaa tgatgctttt atgttggaag ccgctatcta taaattgttg    420
aagtcacatt tcagaaacga aaagtactac atcgatatta ccgaattatt ccacgaagtt    480
actttccaaa cagaattggg tcaattgatg gatttgataa ctgcacctga agataaagtt    540
gacttgtcaa agttttcctt gaagaaacat tcattcatcg tcacctttga aactgcttat    600
tactccttct atttgccagt cgccttggct atgtacgtag ctggtattac tgatgaaaaa    660
gacttgaagc aagcaagaga tgttttgata cctttgggtg aatacttcca aatccaagat    720
gactacttag actgtttcgg tactccagaa caaataggta aaatcggtac agatattcaa    780
gacaataagt gcagttgggt tattaacaag gctttggaat tagcatctgc cgaacaaaga    840
aagactttgg atgaaaacta cggtaaaaag gactcagttg ctgaagcaaa gtgtaagaaa    900
atttttaatg atttgaagat tgaacaattg taccatgaat acgaagaatc catcgctaaa    960
gacttaaagg caaagattag tcaagttgat gaatcaagag gttttaaagc cgacgttttg   1020
acagctttct tgaataaggt ctacaagaga tcaaagtag                         1059
```

<210> SEQ ID NO 25
<211> LENGTH: 1158
<212> TYPE: DNA
<213> ORGANISM: Artificial Sequence
<220> FEATURE:
<223> OTHER INFORMATION: Codon optimized

<400> SEQUENCE: 25
atgaaccatt tgagagccga aggtcctgcc tccgtattag ccataggtac agccaaccca 60
gaaaacatat tgatccaaga tgaatttcct gattattact tcagagttac caagagtgaa 120
cacatgactc aattgaagga aaagtttaga aaaatatgtg ataagtctat gatcagaaag 180
agaaactgct tcttgaacga agaacatttg aagcaaaatc caagattggt agaacacgaa 240
atgcaaacat tggatgccag acaagacatg ttagttgtcg aagttcctaa attgggtaaa 300
gatgcttgtg caaaagccat taaggaatgg ggtcaaccaa agtcaaagat cactcatttg 360
atttttacaa gtgcatctac tacagatatg cctggtgcag actaccactg tgccaaattg 420
ttaggtttgt caccatccgt taagagagtc atgatgtatc aattaggttg ctacggtggt 480
ggtactgttt tgagaatcgc taaggatatt gcagaaaaca acaagggtgc cagagtatta 540
gctgtttgtt gcgacattat ggcttgcttg tttagaggtc caagtgattc tgacttggaa 600
ttgttagttg gtcaagctat cttcggtgac ggtgctgctg ctgttattgt tggtgcagaa 660
cctgacgaat ctgttggtga aagaccaata tttgaattag tcagtacagg tcaaaccatc 720
ttgcctaatt ctgaaggtac aattggtggt catataagag aagcaggttt gatcttcgat 780
ttgcacaaag acgttccaat gttaatctct aacaacatag aaaagtgttt gatagaagca 840
ttcactccta taggtatctc agattggaac tctattttct ggataacaca tccaggtggt 900
aaagccattt tggataaggt tgaagaaaaa ttggatttga agaaagaaaa gtttgtagat 960
agtagacatg ttttatctga acacggtaac atgtcttcat ccactgtctt gttcgtaatg 1020
gatgaattga gaaagagatc attagaagag ggtaaatcta ctactggtga cggttttgaa 1080
tggggtgtct tatttggttt cggtcctggt ttgaccgtcg aaagagtagt tgtcagatca 1140
gtaccaatta aatattag 1158

<210> SEQ ID NO 26
<211> LENGTH: 315
<212> TYPE: DNA
<213> ORGANISM: Artificial Sequence
<220> FEATURE:
<223> OTHER INFORMATION: Codon optimized

<400> SEQUENCE: 26
atggccgtca agcatttgat agtattgaag tttaaagatg aaatcacaga agctcaaaag 60
gaagaatttt tcaagaccta cgttaatttg gtcaacatta tacctgctat gaaagatgta 120
tactggggta aagacgttac acaaaagaaa gaagaaggtt atacacacat tgtcgaagta 180
accttcgaat cagttgaaac tatccaagat tacatcattc atccagctca cgttggtttt 240
ggtgacgttt acagatcctt ctgggaaaaa ttgttgatct tcgattacac cccaagaaag 300
ttaaagccaa aataa 315

<210> SEQ ID NO 27
<211> LENGTH: 1188
<212> TYPE: DNA
<213> ORGANISM: Artificial Sequence
<220> FEATURE:

<223> OTHER INFORMATION: Codon optimized

<400> SEQUENCE: 27

```
atgggtttat catccgtctg tactttctcc ttccaaacta actatcatac cttattgaat     60
cctcacaaca acaatccaaa aacatcattg ttgtgttaca gacatccaaa gacacctatt    120
aagtactctt acaacaactt tccatcaaaa cattgttcaa ccaagtcctt ccacttacaa    180
aataagtgct ccgaaagttt gtctatagct aagaactcta tcagagctgc aactacaaat    240
caaactgaac cacctgaaag tgataatcac tctgttgcca caaaaatttt gaacttcggt    300
aaagcatgtt ggaagttgca aagaccatac accataatcg cttttacttc ttgtgcatgc    360
ggtttattcg gtaaagaatt gttgcataac actaacttaa tttcatggtc cttgatgttc    420
aaggcatttt tctttttagt tgccatcttg tgcatcgctt cattcaccac tacaattaat    480
caaatatacg atttgcacat cgacagaatt aacaaaccag atttgccttt ggcttcaggt    540
gaaatatccg tcaatactgc atggatcatg tctatcatag tagccttgtt cggtttgatc    600
atcacaatta aaatgaaggg tggtccattg tacatcttcg gttactgttt cggtatcttc    660
ggtggtattg tctattccgt accacctttt agatggaaac aaaaccctag tactgccttt    720
ttgttgaatt tcttagctca tatcatcaca aacttcacct tctactacgc ttcaagagct    780
gctttaggtt tgccattcga attgagacct tcattcacat tttgttggc attcatgaaa    840
agtatgggtt ctgcattagc cttgatcaag gatgcctctg acgttgaagg tgacacaaag    900
ttcggtatta gtaccttggc ttctaagtac ggttcaagaa atttgacttt gttctgctcc    960
ggtatcgttt tgttaagtta cgtcgcagcc attttggcag gtatcatttg gccacaagcc   1020
tttaattcta acgttatgtt gttgtcacat gccatcttgg ctttctggtt gatcttgcaa   1080
actagagatt tcgctttgac aaattatgac cctgaagcag gtagaagatt ctacgagttt   1140
atgtggaaat tgtactacgc tgaatatttg gtatacgttt ttatttag                1188
```

<210> SEQ ID NO 28
<211> LENGTH: 1635
<212> TYPE: DNA
<213> ORGANISM: Artificial Sequence
<220> FEATURE:
<223> OTHER INFORMATION: Codon optimized

<400> SEQUENCE: 28

```
atgaaatgtt caactttctc cttttggttc gtatgcaaga tcatcttctt tttcttttcc     60
tttaacatcc aaacaagtat cgcaaaccca agagaaaact tttgaagtg cttctcacaa    120
tacataccta ataacgccac caatttgaag ttggtttaca ctcaaaacaa cccattgtac    180
atgtccgtct tgaacagtac aatccataat ttgagattca cttctgatac cactccaaaa    240
cctttggtca ttgtaacccc tagtcatgta tctcacatcc aaggtactat cttatgttct    300
aaaaaggttg gtttgcaaat tagaactaga tccggtggtc atgatagtga aggcatgtca    360
tacatctccc aagttccatt cgttatcgtt gatttgagaa acatgagatc aattaaaata    420
gacgtacact cacaaactgc ttgggttgaa gctggtgcaa cattgggtga agtatactac    480
tgggttaacg aaaagaatga aaacttatca ttggctgctg gttactgtcc aacagtttgc    540
gcaggtggtc attttggtgg tggtggttat ggtcctttaa tgagaaacta cggtttggcc    600
gctgataaca taatcgacgc tcatttggta aatgttcacg gtaaagtttt ggatagaaag    660
tctatgggtg aagacttatt ttgggctttg agaggtggtg gtgcagaatc attcggtatc    720
atagttgctt ggaagataag attagtcgca gtaccaaagt ctactatgtt ctcagtcaaa    780
```

```
aagataatgg aaatccatga attagttaaa ttggtcaata agtggcaaaa catcgcatac    840
aagtacgata aggacttgtt gttgatgact catttcatca caagaaacat caccgataac    900
caaggtaaaa ataagactgc tatccacaca tacttttctt cagttttctt gggtggtgtc    960
gattccttag tagacttgat gaataagtct tttccagaat taggtattaa gaaaactgat   1020
tgtagacaat tgtcttggat cgacaccatc atcttttatt caggtgttgt caactacgat   1080
acagacaact tcaacaaaga aatattattg gatagatccg caggtcaaaa cggtgccttt   1140
aaaattaagt tagactacgt taaaaagcca atacctgaat cagttttcgt ccaaatctta   1200
gaaaaattgt acgaagaaga tattggtgca ggcatgtacg ccttgtatcc atacggtggt   1260
ataatggacg aaatcagtga atctgccatt ccatttcctc atagagctgg tatcttatac   1320
gaattgtggt acatttgttc atgggaaaag caagaagata acgaaaagca cttaaactgg   1380
attagaaaca tctataactt catgactcca tacgtttcta aaaaccctag attggcatat   1440
ttgaactaca gagatttgga catcggtatt aacgatccaa agaatcctaa caactatacc   1500
caagctagaa tttggggtga aaaatacttc ggtaaaaatt tcgatagatt agtaaaggtt   1560
aagacattgg ttgacccaaa caacttcttt agaaacgaac aatccattcc acctttacct   1620
agacatagac actga                                                    1635
```

<210> SEQ ID NO 29
<211> LENGTH: 1638
<212> TYPE: DNA
<213> ORGANISM: Artificial Sequence
<220> FEATURE:
<223> OTHER INFORMATION: Codon optimized

<400> SEQUENCE: 29

```
atgaactgct ccgcattctc tttctggttc gtctgtaaaa taatcttctt cttcttgtcc     60
ttcaacatcc aaatctccat cgcaaatcca caagaaaact tttgaagtg tttctccgaa    120
tacatcccaa acaaccctgc taacccaaag tttatatata ctcaacatga tcaattgtac    180
atgtccgttt tgaacagtac catccaaaat ttgagattca cttctgacac tacaccaaaa    240
cctttagtca ttgttacacc ttccaatgtt agtcacattc aagcttctat attgtgctct    300
aagaaagtag gtttgcaaat cagaactaga tcaggtggtc atgatgcaga aggcatgtct    360
tacatctcac aagttccatt cgttgtagtc gatttgagaa atatgcattc cataaagatc    420
gacgttcaca gtcaaacagc atgggtagaa gcaggtgcca ccttgggtga agtttactac    480
tggatcaacg aaaagaatga aaacttttct ttccctggtg gttactgtcc aacagtaggt    540
gtcggtggtc acttttctgg tggtggttat ggtgcattga tgagaaacta cggtttagct    600
gcagataata ttatagacgc ccatttggtt aacgtagatg gtaaagtttt ggacagaaag    660
tctatgggtg aagatttgtt ttgggccata agaggtggtg gtggtgaaaa tttcggtatc    720
attgccgctt ggaaaattaa gttagtcgct gttccttcca aagtactatt tttctctgtc    780
aaaaagaaca tggaaatcca cggtttggtt aagttgttta ataagtggca aaacatcgct    840
tacaagtacg ataaggactt ggttttgatg acccatttca tcactaaaaa tattacagat    900
aaccatggta aaaataagac cactgttcac ggttattttt cttcaatttt ccatggtggt    960
gtagattctt tggttgattt gatgaataag tcattcccag aattgggtat taaaaagaca   1020
gattgcaagg aattttcttg gatagacaca accatcttct attcaggtgt tgtaaacttc   1080
aacaccgcta acttcaaaaa ggaaatcttg ttggatagat ccgctggtaa aaagaccgct   1140
```

```
ttttctatta aattggacta cgttaagaaa ccaatccctg aaactgcaat ggtcaagata   1200

ttggaaaagt tgtacgaaga agatgtaggt gtcggcatgt acgttttgta tccatacggt   1260

ggtattatgg aagaaatatc tgaatcagcc ataccatttc ctcacagagc tggtatcatg   1320

tatgaattat ggtacacagc ctcatgggaa aagcaagaag ataacgaaaa gcatatcaac   1380

tgggtcagat ccgtttacaa cttcactaca ccttacgtta gtcaaaaccc aagattggca   1440

tatttgaact acagagattt ggacttaggt aaaactaacc ctgaatctcc aaataactat   1500

acacaagcaa gaatttgggg tgaaaagtac tttggtaaaa atttcaacag attagttaaa   1560

gtaaagacta aagccgaccc taacaacttt ttcagaaacg aacaatccat cccacctttg   1620

ccacctcacc accactaa                                                 1638
```

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
aggaaacgaa gataaatctc gagtttatca ttatcaatac tg 42

<210> SEQ ID NO 31
<211> LENGTH: 37
<212> TYPE: DNA
<213> ORGANISM: Artificial Sequence
<220> FEATURE:
<223> OTHER INFORMATION: Primer

<400> SEQUENCE: 31
ggaaaaatca gtcaaggcaa attaaagcct tcgagcg 37

<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32
gatgggggat ccactagttc tagaatc 27

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
tgatgggctg caggaattcg atatc 25

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34
gaactagtgg atcccccatc atgaaccatt tgagagcc 38

<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
tattttggct ttaactttct tggggtgtaa tc 32

<210> SEQ ID NO 36
<211> LENGTH: 43
<212> TYPE: DNA
<213> ORGANISM: Artificial Sequence
<220> FEATURE:
<223> OTHER INFORMATION: Primer

<400> SEQUENCE: 36
agaaagttaa agccaaaata atgataacga gaataatatc aag 43

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
ataaacccat ggcgcagacc tgtgagag 28

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
ggtctgcgcc atgggtttat catccgtc 28

<210> SEQ ID NO 39
<211> LENGTH: 41
<212> TYPE: DNA
<213> ORGANISM: Artificial Sequence
<220> FEATURE:
<223> OTHER INFORMATION: Primer

<400> SEQUENCE: 39
cgaattcctg cagcccatca gtgtctatgt ctaggtaaag g 41

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
tgatgggctg caggaattcg atatc 25

<210> SEQ ID NO 41
<211> LENGTH: 27
<212> TYPE: DNA
<213> ORGANISM: Artificial Sequence
<220> FEATURE:
<223> OTHER INFORMATION: Primer

```
<400> SEQUENCE: 41

gatgggggat ccactagttc tagaatc                                   27


<210> SEQ ID NO 42
<211> LENGTH: 33
<212> TYPE: DNA
<213> ORGANISM: Artificial Sequence
<220> FEATURE:
<223> OTHER INFORMATION: Primer

<400> SEQUENCE: 42

caccagaacc gaaggtagag gttctttgtt aac                            33


<210> SEQ ID NO 43
<211> LENGTH: 45
<212> TYPE: DNA
<213> ORGANISM: Artificial Sequence
<220> FEATURE:
<223> OTHER INFORMATION: Primer

<400> SEQUENCE: 43

cgaattcctg cagcccatca ctttgatctc ttgtagacct tattc               45


<210> SEQ ID NO 44
<211> LENGTH: 42
<212> TYPE: DNA
<213> ORGANISM: Artificial Sequence
<220> FEATURE:
<223> OTHER INFORMATION: Primer

<400> SEQUENCE: 44

gaactagtgg atcccccatc atggtttcca atcacttgtt tg                  42


<210> SEQ ID NO 45
<211> LENGTH: 29
<212> TYPE: DNA
<213> ORGANISM: Artificial Sequence
<220> FEATURE:
<223> OTHER INFORMATION: Primer

<400> SEQUENCE: 45

ctctaccttc ggttctggtg tataagtcg                                 29


<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46

gatccactag ttctagaatc cg                                        22


<210> SEQ ID NO 47
<211> LENGTH: 35
<212> TYPE: DNA
<213> ORGANISM: Artificial Sequence
<220> FEATURE:
<223> OTHER INFORMATION: Primer

<400> SEQUENCE: 47

tctagaacta gtggatcatg aaccatttga gagcc                          35


<210> SEQ ID NO 48
<211> LENGTH: 28
```

```
<212> TYPE: DNA
<213> ORGANISM: Artificial Sequence
<220> FEATURE:
<223> OTHER INFORMATION: Primer

<400> SEQUENCE: 48

tcgttatcac tttcttgggg tgtaatcg                                          28


<210> SEQ ID NO 49
<211> LENGTH: 36
<212> TYPE: DNA
<213> ORGANISM: Artificial Sequence
<220> FEATURE:
<223> OTHER INFORMATION: Primer

<400> SEQUENCE: 49

ccaagaaagt gataacgaga ataatatcaa gaatac                                36


<210> SEQ ID NO 50
<211> LENGTH: 44
<212> TYPE: DNA
<213> ORGANISM: Artificial Sequence
<220> FEATURE:
<223> OTHER INFORMATION: Primer

<400> SEQUENCE: 50

aggtcgacgg tatcgttaaa taaaaacgta taccaaatat tcag                      44


<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51

cgataccgtc gacctcga                                                     18


<210> SEQ ID NO 52
<211> LENGTH: 32
<212> TYPE: DNA
<213> ORGANISM: Artificial Sequence
<220> FEATURE:
<223> OTHER INFORMATION: Primer

<400> SEQUENCE: 52

ggttaaacta gtatgggtaa aaactataag tc                                    32


<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53

gtgcccgtcg actcattcga aatgactgaa ttg                                   33
```

PRODUCTION OF CANNABINOIDS IN YEAST

CROSS-REFERENCE TO RELATED APPLICATIONS

This application claims the benefit and priority of U.S. Provisional Patent Application Ser. No. 62/024,099 filed Jul. 14, 2014, titled "Terpenophenolic Production in Microorganisms," which is incorporated by reference herein.

REFERENCE TO SEQUENCE LISTINGS

The present application is filed with sequence listing(s) attached hereto and incorporated by reference, including Appendix 1B titled "Sequence IDs".

FIELD OF THE INVENTION

This invention relates to molecular biology, and more specifically to the transformation of yeast cells and the production of cannabinoids.

SUMMARY OF THE INVENTION

Exemplary embodiments provided herein include genetically engineering microorganisms, such as yeast or bacteria, to produce cannabinoids by inserting genes that produce the appropriate enzymes for the metabolic production of a desired compound.

DETAILED DESCRIPTION OF EXEMPLARY EMBODIMENTS

Figure 1:
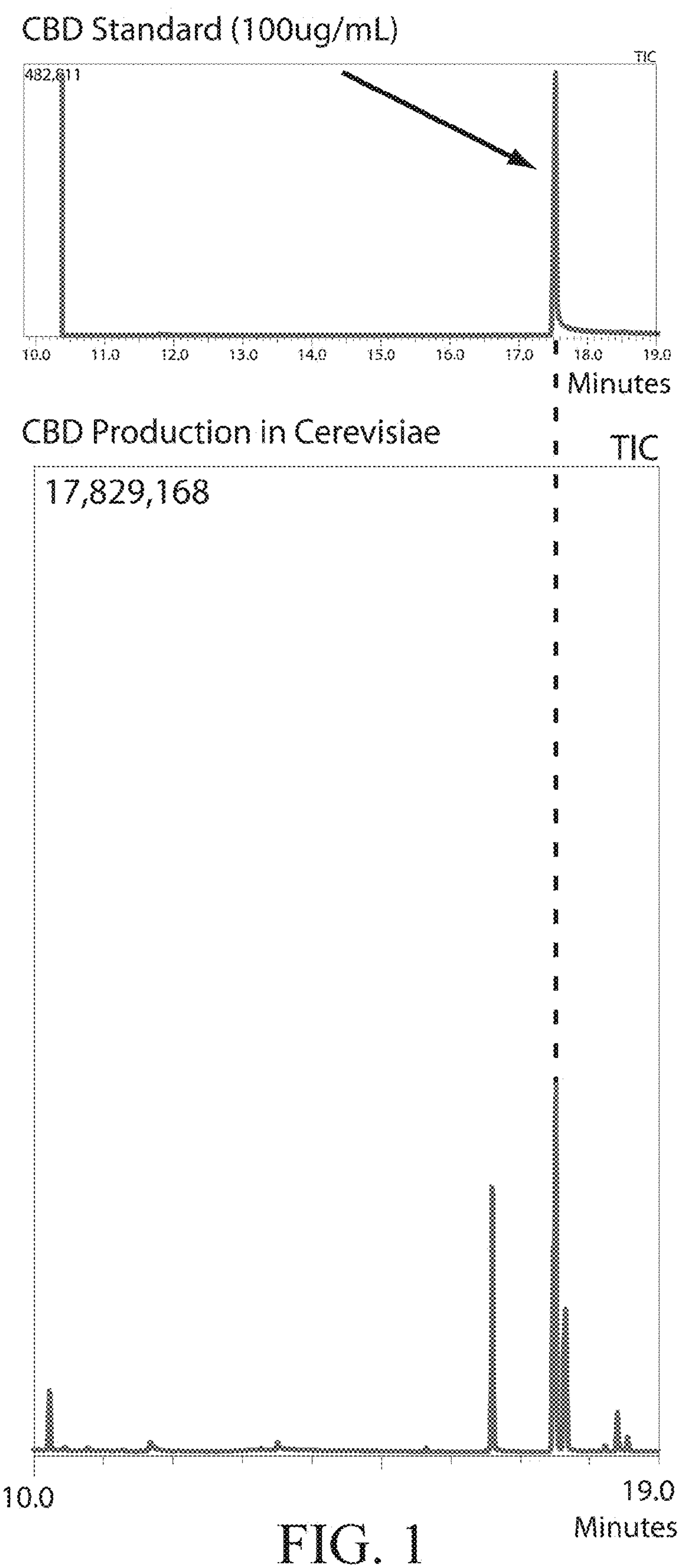
FIG. 1 shows exemplary experimental data achieved in connection with Example 1 of Appendix 1A titled "Additional Examples" for cannabidiol ("CBD")/cannabidiolic acid ("CBDA") production in *S. cerevisiae.*

The present application relates to the field of cannabinoid production in yeasts. Cannabinoids are a general class of chemicals that act on cannabinoid receptors and other target molecules to modulate a wide range of physiological behavior such as neurotransmitter release. Cannabinoids are produced naturally in humans (called endocannabinoids) and by several plant species (called phytocannabinoids) including *Cannabis sativa*. Cannabinoids have been shown to have several beneficial medical/therapeutic effects and therefore they are an active area of investigation by the pharmaceutical industry for use as pharmaceutical products for various diseases.

Currently the production of cannabinoids for pharmaceutical or other use is done by chemical synthesis or through the extraction of cannabinoids from plants that are producing these cannabinoids, for example *Cannabis sativa*. There are several drawbacks to the current methods of cannabinoid production. The chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*. Although there are drawbacks to chemically synthesized cannabinoids, the benefit of this production method is that the end product is a highly pure single cannabinoid. This level of purity is preferred for pharmaceutical use. The level of purity required by the pharmaceutical industry is reflected by the fact that no plant extract based cannabinoid production has received FDA approval yet and only synthetic compounds have been approved.

In contrast to the synthetic chemical production of cannabinoids, the other method that is currently used to produce cannabinoids is production of cannabinoids in plants that naturally produce these chemicals; the most used plant for this is *Cannabis sativa*. In this method, the plant *Cannabis sativa* is cultivated and during the flowering cycle various cannabinoids are produced naturally by the plant. The plant can be harvested and the cannabinoids can be ingested for pharmaceutical purposes in various methods directly from the plant itself or the cannabinoids can be extracted from the plant. There are multiple methods to extract the cannabinoids from the plant *Cannabis sativa*. All of these methods typically involve placing the plant, *Cannabis sativa* that contains the cannabinoids, into a chemical solution that selectively solubilizes the cannabinoids into this solution. There are various chemical solutions used to do this such as hexane, cold water extraction methods, CO2 extraction methods, and others. This chemical solution, now containing all the different cannabinoids, can then be removed, leaving behind the excess plant material. The cannabinoid containing solution can then be further processed for use.

There are several drawbacks of the natural production and extraction of cannabinoids in plants such as *Cannabis sativa*. Since there are numerous cannabinoids produced by *Cannabis sativa* it is often difficult to reproduce identical cannabinoid profiles in plants using an extraction process. Furthermore, variations in plant growth will lead to different levels of cannabinoids in the plant itself making reproducible extraction difficult. Different cannabinoid profiles will have different pharmaceutical effects which are not desired for a pharmaceutical product. Furthermore, the extraction of cannabinoids from *Cannabis sativa* extracts produces a mixture of cannabinoids and not a highly pure single pharmaceutical compound. Since many cannabinoids are similar in structure it is difficult to purify these mixtures to a high level resulting in cannabinoid contamination of the end product.

Disclosed herein are strategies for creating cannabinoids in microorganisms such as yeast and methods to produce various cannabinoids in yeast from a simple sugar source. The general methods involve genetically engineering yeast to produce various cannabinoids, where the main carbon source available to the yeast is a sugar (glucose, galactose, fructose, sucrose, honey, molasses, raw sugar, etc.). Genetic engineering of the microorganism involves inserting various genes that produce the appropriate enzymes and/or altering the natural metabolic pathway in the microorganism to achieve the production of a desired compound. Through genetic engineering of microorganisms these metabolic pathways can be introduced into these microorganisms and the same metabolic products that are produced in the plant *Cannabis sativa* can be produced by the microorganisms. The benefit of this method is that once the microorganism is produced, the production of the cannabinoid is low cost and reliable, only a specific cannabinoid is produced or a subset is produced, depending on the organism. The purification of the cannabinoid is straight forward since there is only a single cannabinoid or a selected few cannabinoids present in the microorganism. The process is a sustainable process which is more environmentally friendly than synthetic production.

FIG. 1 shows exemplary experimental data achieved in connection with Example 1 of Appendix 1A titled "Additional Examples" for cannabidiol ("CBD")/cannabidiolic acid ("CBDA") production in *S. cerevisiae.*

FIG. 1 shows gas chromatography-mass spectrometry of cannabidiol (CBD) produced in *S. cervisiae*. After processing the yeast cells, as described in Example 1 of Appendix 1A, the whole cell ethyl acetate extract is analyzed for the presences of CBD. The samples were prepared in a way similar to that shown in Appendix A1 except that no MSTFA derivatization was used in this sample (therefore CBDA turns into CBD upon heating), the oven protocol was also slightly different than that shown in Appendix 1A. Initially, a standard CBD solution is run (100 ug/mL; TOP). After running the standard the inventors determined the run time of 17.5 minutes. After running the standard the inventors repeated the GC-MS experiment with their whole cell extract (BOTTOM). At a run time of 17.5 minutes, the inventors saw the same peak as in the standard. Mass spectrometry analysis of the peaks showed identical mass for the two samples (standard and extract) indicating the presence of CBD in their whole cell extract.

Figure 2:
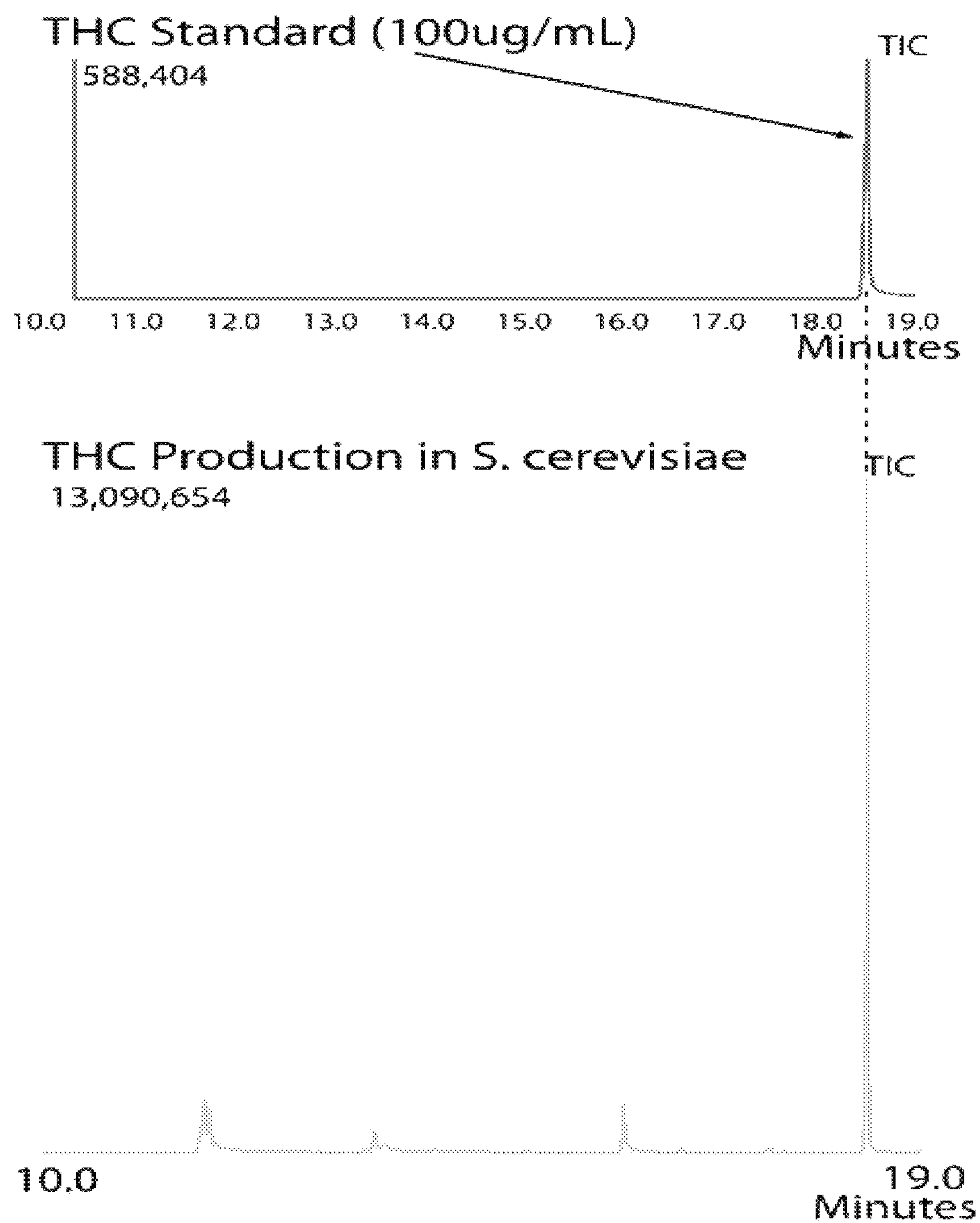
FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae.*

FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae.*

FIG. 2 shows gas chromatography-mass spectrometry of tetrahydrocannabinol (THC) produced in *S. cervisiae*. After processing the yeast cells, as described in Example 2 of Appendix 1A, the whole cell ethyl acetate extract was analyzed for the presences of THC. The samples were prepared in a way similar to that shown in Appendix 1A except that no MSTFA derivatization was used in this sample (therefore THCA turns into THC upon heating), the oven protocol was also slightly different than that shown in Appendix 1A. Initially, a standard CBD solution was run (100 ug/mL; TOP). After running the standard the inventors determined the run time of 18.5 minutes. After running the standard the inventors repeated the GC-MS experiment with their whole cell extract (BOTTOM). At a run time of 18.5 minutes, the inventors saw the same peak as in the standard. Mass spectrometry analysis of the peaks showed identical mass for the two samples (standard and extract) indicating the presence of THC in their whole cell extract.

Figure 3:
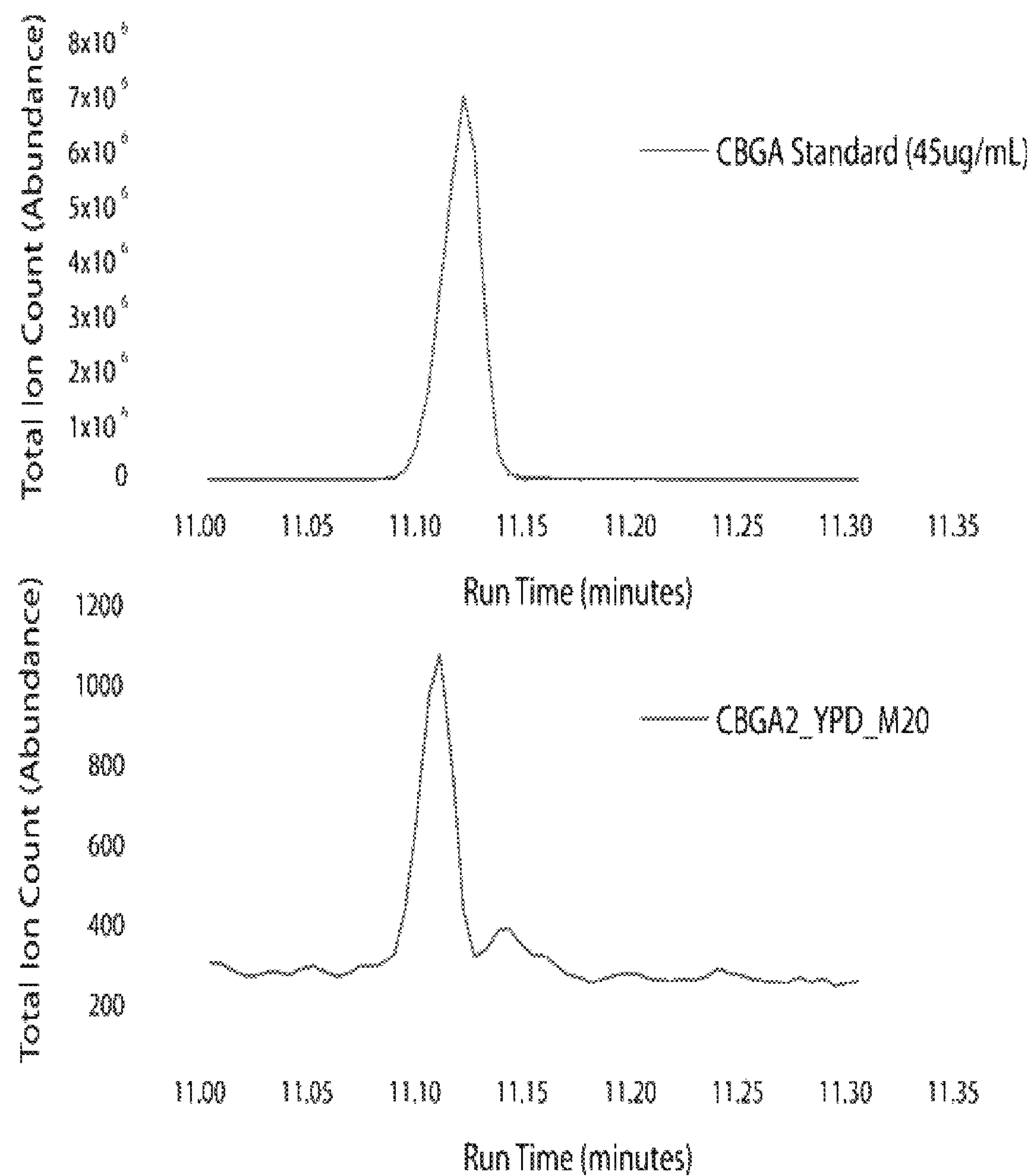
FIG. 3 shows exemplary experimental data achieved in connection with Example 3 of Appendix 1A titled "Additional Examples" for cannabigerol ("CBG")/cannabigerolic acid ("CBGA") production in *S. cerevisiae.*

FIG. 3 shows exemplary experimental data achieved in connection with Example 3 of Appendix 1A titled "Additional Examples" for cannabigerol ("CBG")/cannabigerolic acid ("CBGA") production in *S. cerevisiae.*

FIG. 3 shows gas chromatography-mass spectrometry of cannabigerolic acid (CBGA) produced in *S. cervisiae*. After processing the yeast cells, as described in Example 3 of Appendix 1A, the whole cell ethyl acetate extract was analyzed for the presences of CBGA. The samples were prepared in a way as described in Appendix 1A, but the oven protocol was also slightly different than that shown in Appendix 1A. Initially, a standard CBGA solution was run (45 ug/mL; TOP). After running the standard, the inventors determined the run time of 11.1 minutes. After running the standard, the inventors repeated the GC-MS experiment with their whole cell extract (BOTTOM). At a run time of 11.1 minutes, the inventors saw the same peak as in the standard. Mass spectrometry analysis of the peaks showed identical mass for the two samples (standard and extract) indicating the presence of CBGA in their whole cell extract.

Figure 4:
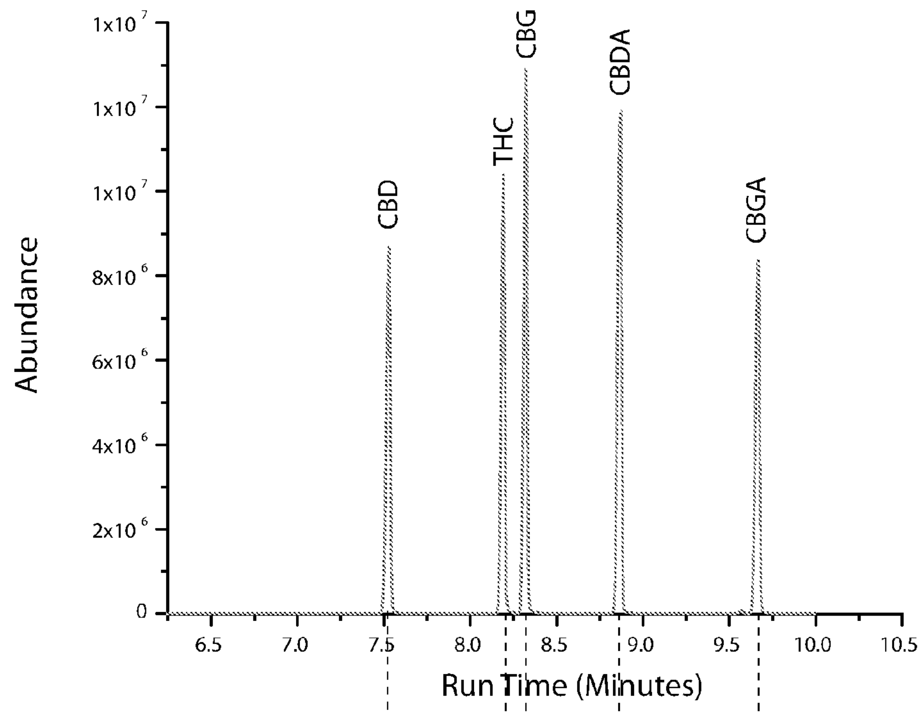
FIG. 4 shows exemplary experimental data achieved in connection with Example 4 of Appendix 1A titled "Additional Examples" for CBGA, CBDA, CBD, CBG and THC production in *K. marxianus.*
Figure 4:
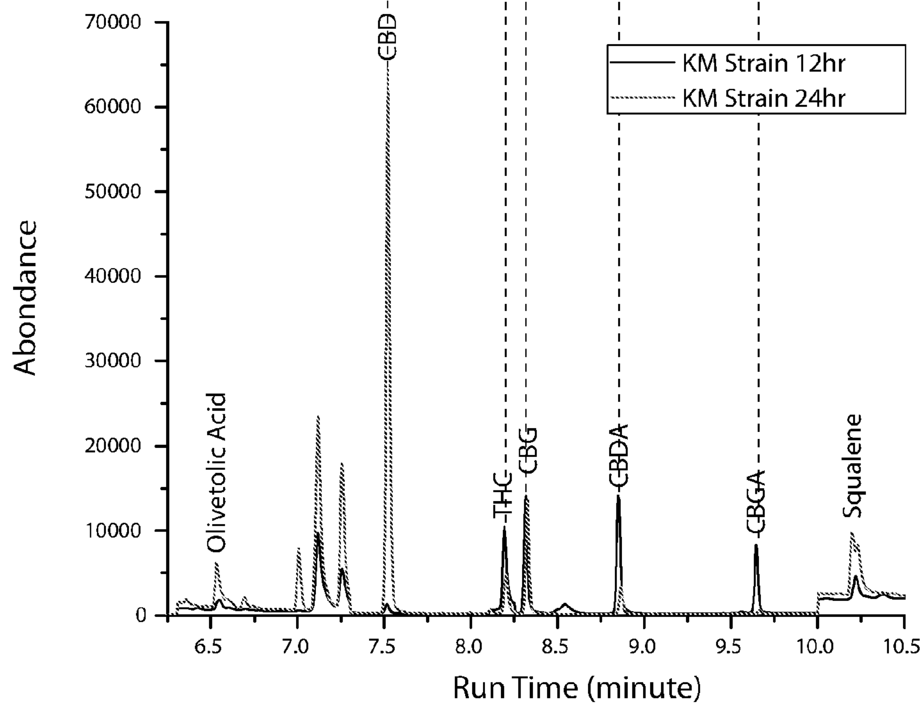

FIG. 4 shows exemplary experimental data achieved in connection with Example 4 of Appendix 1A titled "Additional Examples" for CBGA, CBDA, CBD, CBG and THC production in *K. marxianus.*

FIG. 4 shows gas chromatography-mass spectrometry of cannabinoid production (CBGA, CBDA, CBD, CBG, THC) produced in *K. marxianus*. After processing the yeast cells, as described in Example 4 of Appendix 1A, the whole cell ethyl acetate extract was analyzed for the presence of cannabinoids. The samples were prepared in a way as described in Appendix 1A, but the oven protocol was also slightly different than that shown in Appendix 1A. Initially, a standard solution containing CBD, CBG, THC, CBDA, and CBGA was run (70 ug/mL each; TOP). After running the standard, the inventors determined the run time for each compounds. After running the standard, the inventors repeated the GC-MS experiment with their whole cell extract (BOTTOM). At each run time the inventors saw the same peaks as in the standard. Mass spectrometry analysis of the peaks showed identical mass for the two samples (standard and extract) indicating the presence of cannabinoids in their whole cell extract.

Figure 5:
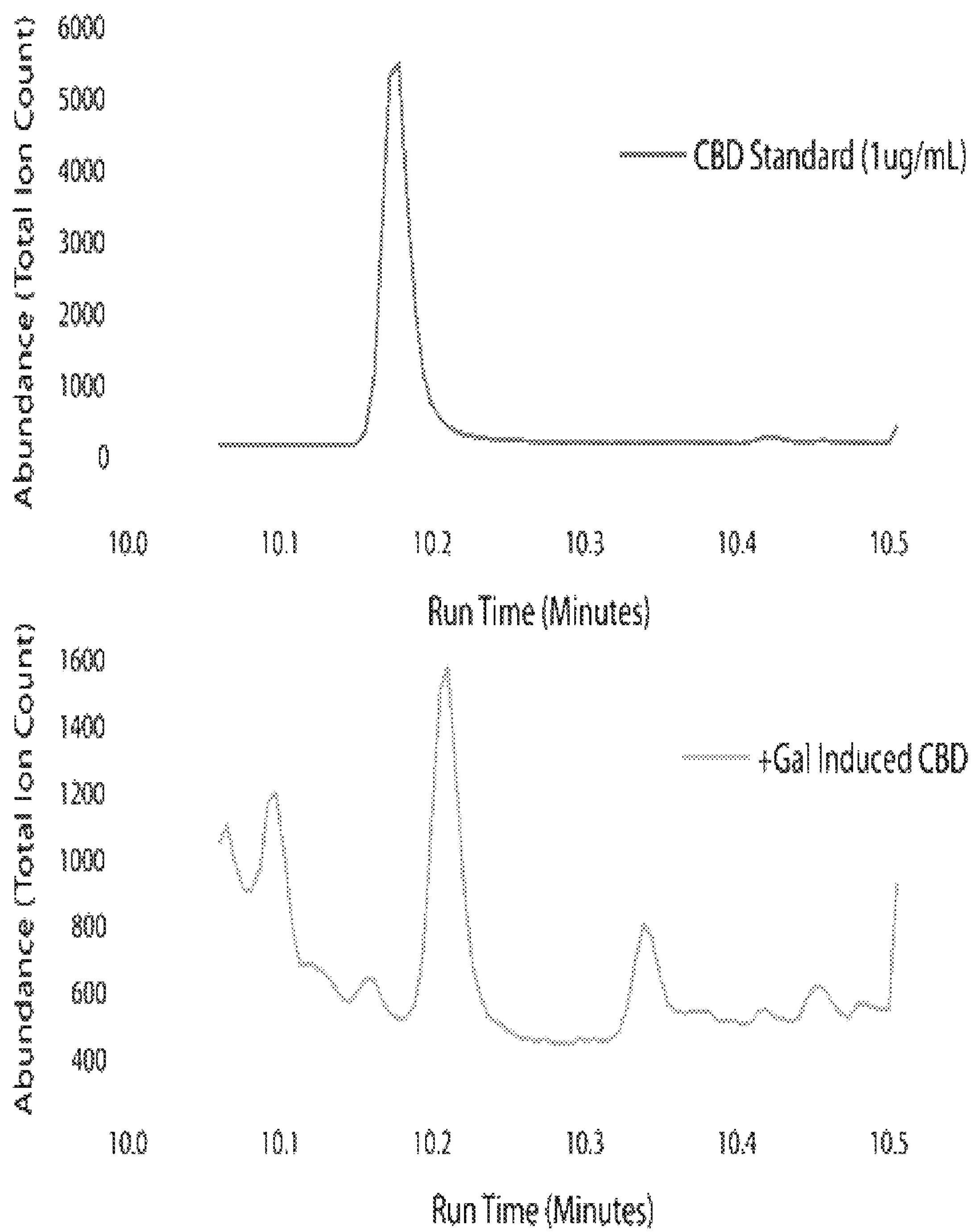
FIG. 5 show exemplary experimental data achieved in connection with Example 5 of Appendix 1A titled "Additional Examples" for galactose induced CBD production in *S. cerevisiae.*

FIG. 5 show exemplary experimental data achieved in connection with Example 5 of Appendix 1A titled "Additional Examples" for galactose induced CBD production in *S. cerevisiae.*

FIG. 5 shows gas chromatography-mass spectrometry of induced cannabidiol (CBD) production in *S. cervisiae*. After processing yeast cells, as described in Example 5 of Appendix 1A, the whole cell ethyl acetate extract was analyzed for the presences of CBD. The samples were prepared in a way as described in Appendix 1A. Initially, a standard solution containing CBD was run (1 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Figure 6:
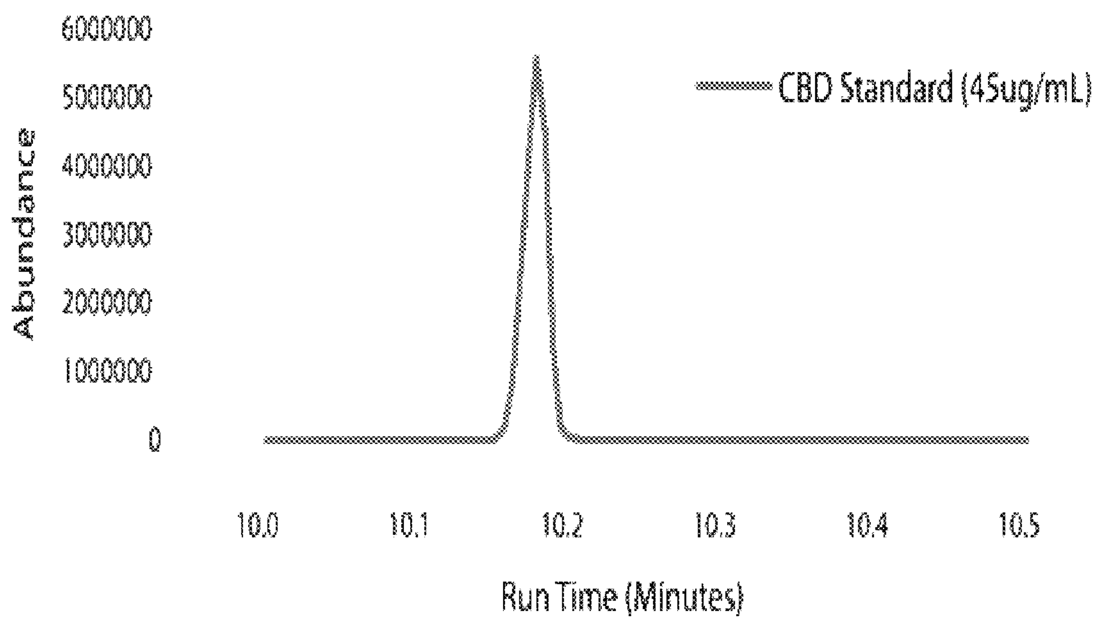
FIG. 6 shows exemplary experimental data achieved in connection with Example 6 of Appendix 1A titled "Additional Examples" for secretion of CBD into media by *S. cerevisiae.*
Figure 6:
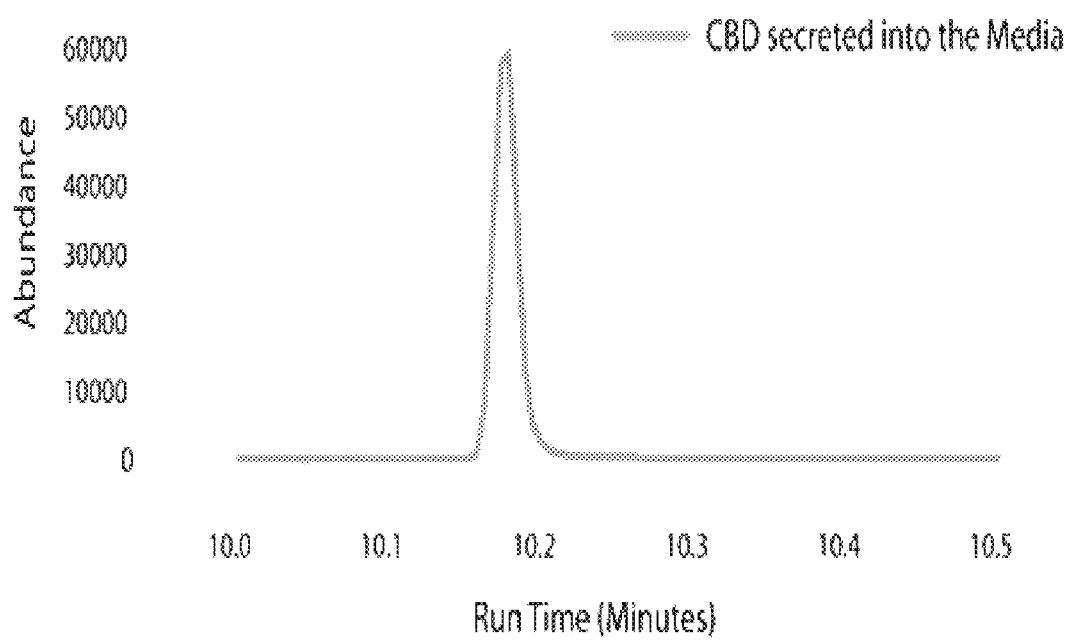

FIG. 6 shows exemplary experimental data achieved in connection with Example 6 of Appendix 1A titled "Additional Examples" for secretion of CBD into media by *S. cerevisiae*.

FIG. 6 shows gas chromatography-mass spectrometry of induced cannabidiol production (CBD) produced in *S. cervisiae* and secreted into the media. After processing the growth media, as described in Example 6 of Appendix 1A, the media ethyl acetate extract was analyzed for the presence of CBD. The samples were prepared in a way as described in Appendix 1A. Initially, a standard solution containing CBD was run (45 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Biosynthetic Production of Cannabidiolic Acid (CBDA) in *S. cerevisiae*.

Through genetic engineering the inventors have reconstituted the cannabidiolic acid (CBDA) metabolic pathway found in *Cannabis sativa* into *S. cerevisiae* (a species of yeast).

Producing CBGA is an initial step in producing many cannabinoids from *Cannabis sativa* in *S. cerevisiae*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Figure 7:
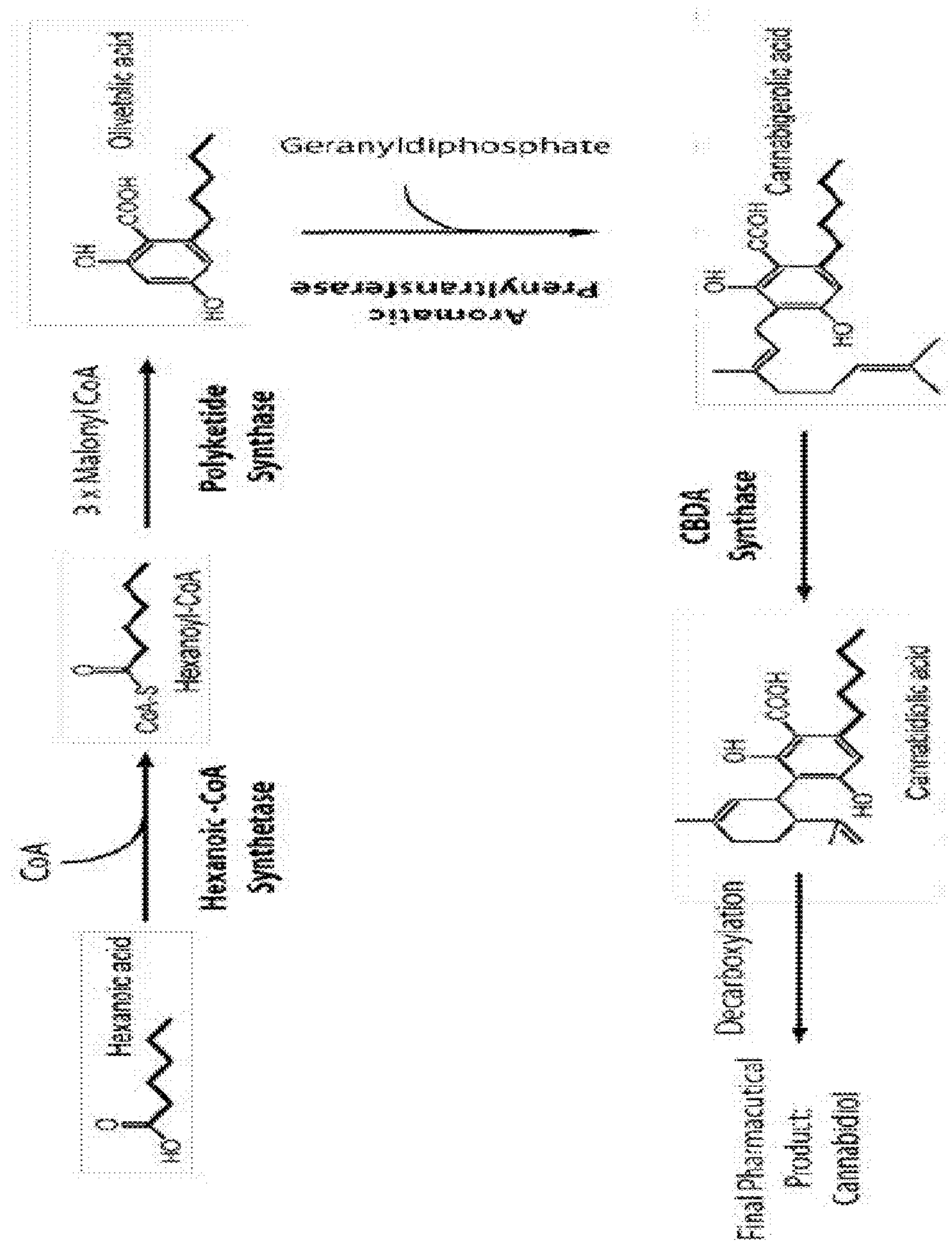
FIG. 7 shows an exemplary metabolic pathway for the production of cannabinoids by *Cannabis sativa.*

FIG. 7 shows an exemplary metabolic pathway for the production of cannabinoids by *Cannabis sativa*.

The biosynthetic route for the production of cannabidiolic acid in *Cannabis sativa* is shown in FIG. 7. The pathway begins with the conversion of Hexanoic acid (a simple fatty acid) to Hexanoyl-CoA by Hexanoyl-CoA Synthetase. Hexanoyl-CoA is converted to Oleviolic acid (OA), a polyketide, by a Polyketide synthase. OA is then prenylated with the monoterpene geranyl diphosphate to cannabigerolic acid by an Aromatic prenyltransferase. Finally, cannabidiolic acid (CBDA) is produced by cyclizing cannabigerolic acid via CBDA synthase (CBDAs). In summary, it takes four enzymatic steps to produce CBDA from Hexanoic acid. The inventors have engineered this metabolic pathway into *S. cerevisiae* (a species of yeast) for the production of CBDA.

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, through genetic engineering many of the required enzymes can be added and the production of GPP can be increased. In order to add the required enzymes for CBDA production in yeast the inventors created plasmids that contain the essential genes in the CBDA biosynthetic pathway. The inventors have transformed these genes into *S. cerevisiae*.

Synthesis of Fusion Genes Required for CBDA Production in *S. cerevisiae*.

The genome of *Cannabis sativa* has been investigated and the acyl-activating enzymes CsAAE1 was determined to convert hexanoic acid to hexanoyl-CoA (Step 1 in FIG. 7). The inventors have overexpressed CsAAE1 in yeast while simultaneously supplementing the growth media with Hexanoic acid. By supplementing the media with hexanoic acid, the inventors ensured that the yeast have the required starting materials for the production of hexanoyl-CoA.

The next enzymatic step that was engineered into the yeast strain was for the production of Olivetolic acid (OA) from hexanoyl-CoA. This step requires the substrates hexanoyl-CoA and 3 malonyl-CoA molecules, with the malonyl-CoA molecule produced by yeast naturally. Olivetolic acid production requires two enzymes for the condensation and subsequent cyclization of malonyl-CoA with hexanoyl-CoA. This process requires the tetraketide synthase, olivetolic synthase (OS), and the polyketide cyclase, olivetolic acid cyclase (OAC). In some embodiments, stoichiometric amounts of both of these enzymes are preferred; as it has been experimentally determined that OAC binds a chemical intermediate made by OS. In various embodiments, in order to ensure the proper amounts of OS and OAC the inventors have created a single gene that is a fusion of OS, a self cleaving T2A peptide, and the OAC gene (OS-T2A-OAC) and in certain cases an HA tag was inserted at the C-terminus of OAC to verify protein expression. This entire fusion protein was produced in yeast and the self cleaving peptide is spliced in vivo to produce OS and OAC.

The next enzymatic step requires the production of geranyl pyrophosphate (GPP). In yeast the prenyltransferace Erg20 condenses isopentenyl diphosphate (IPP) and dimethylallyl diphosphate (DMAP) to geranyl pyrophosphate (GPP) and feranyl pyrophosphate (FPP) naturally. While only these two products are produced in yeast, a greater quantity of FPP when compared to GPP is produced. More GPP is required for the production of CBDA. In order to increase the production of GPP compared to FPP the inventors inserted a mutant prenyltransferase, Erg20(K179E) in the yeast strain. This mutant has been shown to shift the ratio of GPP:FPP to 70:30. This Erg20(K179E) mutant was placed on a fusion gene with CsAAE1, the enzyme for hexanoyl-CoA, and a self-cleaving peptide, T2A (CsAAE1-T2A-Erg20(K179E). We also added a FLAG tag to the C-terminus of the Erg20p (K197E) enzyme (CsAAE1-T2A-Erg20(K179E)-FLAG) to verify expression of this fusion protein in yeast in certain yeast strains. After production in yeast the self-cleaving peptide was cut producing CsAAE1 and Erg20(K179E).

Once the inventors verified that they had enough GPP to prenylate Olivetolic acid to cannabigerolic acid the inventors inserted the aromatic prenyltransferase (CsPt1) gene into the yeast. In this final enzymatic step the inventors placed the cannabidiolic acid synthase (CBDAs) gene into yeast for the conversion of cannabigerolic acid to CBDA. Similar to the inventors' previous approach, they introduced a single gene containing CsPt1, a self-cleaving peptide T2A, CBDs, and in certain cases a MYC tag was inserted at the C-terminus of CBDs in order to verify production of each enzyme (CsPt1-T2A-CBDs-MYC).

Creation of a Stable Yeast Strain Producing the Metabolic Pathway for CBDA.

Three stable transformations of *S. cerevesaie* where created utilizing selection for leucine, uracil and tryptophan. The inventors first transformed an auxotrophic yeast strain (his3D1/leu2/trp1-289/ura3-52) with the CsAAE1-T2A-

Erg20(K197E)-FLAG gene in an integrating vector. 5 μg of CsAAE1-T2A-Erg20(K197E)-FLAG in a vector containing a gene for tryptophan depletion resistance was linearized with the restriction enzyme EcoRV, transformed into chemically competent InVSc1, and grown on Yeast Nitrogen Base without amino acids and 0.5% ammonium sulfate (YNBA) agar plates supplemented with histidine, leucine, tryptophan, 1% glucose and 2% lactic acid are grown at 30° C. until colonies are formed. Any yeast colonies that did not incorporate the plasmid, that contains the CsAAE1-T2A-Erg20 (K197E)-FLAG gene died since the starting yeast strain is a tryptophan auxotroph. All colonies, with successful plasmid incorporation, where picked and grown in YNBA supplemented with histidine, leucine and uracil, 1% glucose and 2% lactic acid. All colonies were screened for protein production by taking whole cell extracts of each induced clone and the total protein was subjected to SDS-PAGE followed by western blotting against the c-terminal tag of Erg20(K197E). Positive clones where stored at −80° C. in glycerol stocks. The highest expressing clone was taken for the second transformation and was be designated as VscGPHA.

Using the VscGPHA strains the inventors added 5 μg of OS-T2A-OAC-HA in the a vector containing a gene for leucine depletion resistance. This plasmid was linearized with the restriction enzyme AseI and transformed into chemically competent VscGPHA and grown on YNBA agar plates supplemented with histidine and uracil, 1% glucose and 2% lactic acid and grown at 30° C. until colonies were formed. Any yeast colonies that did not incorporate the plasmid that contains the OS-T2A-OAC-HA gene died since the VscGPHA is a leucine auxotroph. All colonies, with successful plasmid incorporation, were picked and grown in YNBA supplemented with histidine, and leucine. All colonies were screened for protein production by taking whole cell extracts of each induced clone and subjected the total protein to SDS-PAGE followed by western blotting against the c-terminal HA tag of OAC. Positive clones were stored at −80° C. in glycerol stocks. The highest expressing clone was taken for the second stable transformation and was designated VscGPHOA.

The final stable transformation was done in a similar way as the previous transformation. The CsPT-T2A-CBDAs-MYC gene was placed in the vector containing a gene for uracil depletion resistance 5μg of this plasmid was linearized with EcorV and transformed into chemically competent VscGPHOA. Transformed VscGPHOA was grown in YNBA supplemented with histidine, 1% glucose and 2% lactic acid. Any yeast colonies that did not incorporate the plasmid that contains the CsPT-T2A-CBDAs-MYC gene died since they lacked leucine. All colonies were picked and grown in YNBA supplemented with histidine, 1% glucose and 2% lactic acid. All colonies were screened for protein production by taking whole cell extracts of each induced clone and subjecting the total protein to SDS-PAGE followed by western blotting against the c-terminal Myc tag of CBDAs. Positive clones are stored at −80° C. in glycerol stocks. The highest expressing CBDAs was taken for the final strain and designated VscCBDA.

Production of CBDA in Yeast.

To initiate the reconstituted metabolic pathway of CBDA a colony of VscCBDA was freshly streaked on a plate of a frozen glycerol stock of VscCBDA. A small culture of VscCBDA was grown in YNBA supplemented with 0.05% histidine, 1% glucose, 2% lactic acid, and 0.03% hexanoic acid overnight at 30° C. The overnight culture was transferred to 1 L of YNBA supplemented with 0.05% histidine, 1% glucose, 2% lactic acid, and 0.03% hexanoic acid and was grown at 30° C. until mid log phase. Cells were pelleted by centrifugation then washed with 200 ml of phosphate buffered saline (PBS) and repelleted. Pelleted cells were resuspended with 1 L of YNBA supplemented with 0.05% histidine, 2% galactose, and 0.03% hexanoic acid and grown at 30° C. overnight.

Overnight 1 L cultures were pelleted by centrifugation, resuspended, washed one time in PBS and pelleted. Cell pellets were resuspended in 40% (wt/vol) KOH and 50% (vol/vol) ethanol solution and boiled for 10 minutes. Metabolite extraction was done by extracting from the boiled extracts 3 times with hexane, then 3 times with ethyl acetate. The spent supernatant broth was extracted in a similar fashion as described above. Organic phases of extracts of each sample were pooled then dried by a rotary evaporator and stored for liquid chromatography mass spectrometry (LC-MS) and gas chromatography mass spectrometry (GC-MS) analysis to confirm and quantitate how much CBDA is produced from strain VscCBDA.

Biosynthetic Production of Cannabidiolic Acid (CBDA) in *K. marxianus*

Through genetic engineering the inventors have reconstituted the cannabidiolic acid (CBDA) metabolic pathway found in *Cannabis sativa* into *K. marxianus* (a species of yeast). Producing CBGA is an initial step in producing many cannabinoids from *Cannabis sativa* in *K. marxianus*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Synthesis of Fusion Genes Required for CBDA Production in *k. Marxianus.*

Figure 8:
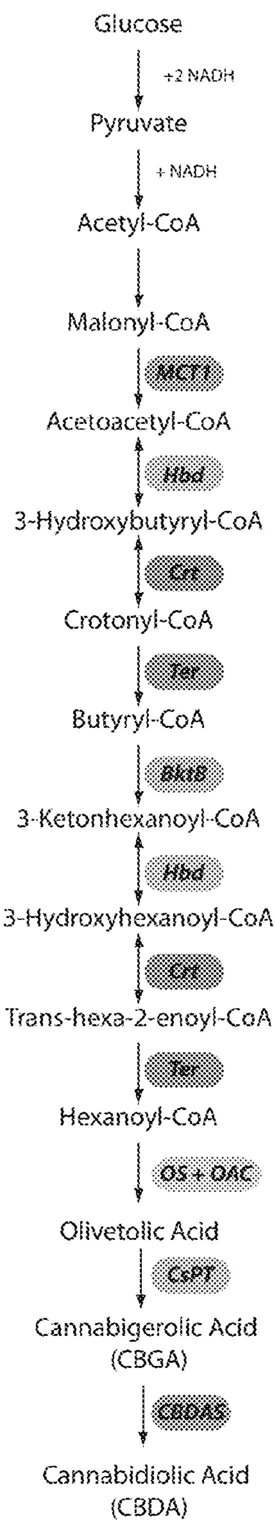
FIG. 8 shows an exemplary biosynthetic route for the production of CBDA from glucose.

FIG. 8 shows an exemplary biosynthetic route for the production of CBDA from glucose.

The biosynthetic route for the production of cannabidiolic acid in *Cannabis sativa*, from glucose to CBDA is shown in FIG. 8. The pathway begins with the conversion of glucose to malonyl-CoA through a series of steps that are common to many strains of yeast. The conversion of malonyl-CoA to Acetoacetyl-CoA is conducted by the enzyme MCT1, an acyl-carrier-protein. Acetoacetyl-CoA is converted to 3-Hydroxybutyryl-CoA by the enzyme 3-hydroxybutyryl-CoA dehydrogenase (Hbd) from *Clostridium acetobutylicum*. Next, 3-Hydroxybutyryl-CoA is converted into Crotonyl-CoA by the enzyme crotonase (Crt) from *Clostridium acetobutylicum* and the conversion of Crotonyl-CoA to Butyryl-CoA is controlled by the enzyme trans-enoyl-CoA reducatase (Ter) from *Treponema denticola*. The Butyryl-CoA is converted to 3-Ketonhexanoyl-CoA by the enzyme β-ketothiolase (Bktb) from *Ralstonia Eutropha.* 3-Ketonhexanoyl-CoA is converted to 3-Hydroxyhexanoyl-CoA by the enzyme Hbd. Hydroxyhexanoyl-CoA is converted to Trans-hexa-2-enoyl-CoA by the enzyme Crt. Trans-hexa-2-enoyl-CoA is converted to Hexanoyl-CoA by the enzyme Ter. Hexanoyl-CoA, with 3 malonyl-CoAs, is converted to Oleviolic acid (OA) by a Polyketide synthase and cyclase, OA and OAC respectively. OA is then prenylated with the monoterpene geranyl diphosphate to cannabigerolic acid by an Aromatic prenyltransferase, CsPT. Finally, cannabidiolic acid (CBDA) is produced by cyclizing cannabigerolic acid via CBDA synthase (CBDAS). We have engineered this metabolic pathway into *K. marxianus* (a species of yeast) for the production of CBDA (FIG. 8).

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, the inventors through genetic engineering created many of the required enzymes that can be added so the production of GPP was increased. In order to add the required enzymes for CBDA production in yeast the inventors created plasmids that contain the essential genes in the CBDA biosynthetic pathway. The inventors have transformed these genes into *K. marxianus*.

Creation of a Stable *K. marxianus* Strain Producing the Metabolic Pathways for Hexonyl-coA and CBDA.

Two stable transformations of *K. marxianus* were created utilizing selection for uracil and G418 (Genenticin). The inventors first transformed an auxotrophic *K. marxianus* strain (ATCC 17555 KM5) with 5 different genes needed to produce high levels of hexanoyl-CoA. After functional conformation of the genes required for hexanoyl-CoA the inventors did a second transformation with the genes responsible for CBDA production. The molecular biology methods required for biosynthetic production of CBDA in *K. marxianus* are outlined below.

Gene names Crt, Bktb, MCT1, TeR, Hbd, Erg20p(K179E) were codon optimized, synthesized and subclonned into puc57 and p426 ATCC with the restriction enzymes SpeI and SalI.

Genes Crt, Bktb, MCT1, TeR, Hbd, and Erg20p(K179E) were amplified via PCR using the primers GPD_F and URA_R and all 6 amplicons were electroporated into *K. Marxianus* ATCC 17555 KM5 at a concentration of 200 nM and selected onto yeast nitrogen base (YNB) supplemented with amino acid dropout mix (DO supplement-Ura Clonetech 630416) 2% glucose, and 2% Agar plates.

Gene integration and functional gene expression of Crt, Bktb, MCT1, TeR, Hbd, and Erg20p(K179E) was validated by genomic PCR and RT-PCR methods respectively. The final strain produced containing the functional expression of Crt, Bktb, MCT1, TeR, Hbd, and Erg20p(K179E) was labeled kMarxHex1.

Gene names CBDAs, CsPt, OS, and OAC were codon optimized and synthesized by Genscript. The codon optimized gene sequences of CBDAs and CsPt were cloned in frame with a nucleotide sequence containing a self cleaving T2A peptide and designated as CstTCbds. The codon optimized gene sequences of OS and OAC were cloned in frame with a nucleotide sequence containing a self cleaving T2A peptide and designated as OSTOc. CsTCbds and OSTOc were cloned in frame with an *S. cerevisiae* internal ribosomal entry site (IRES), Ure2, into a galactose inducible vector and the final gene sequence pcen/arsGal-OSTOc-IRES-CsTCbds plasmid can be seen below. The plasmid pcen/arsGal-OSTOc-IRES-CstTCbds was used to synthesize a functional gene fragment that expresses the enzymes CBDAs, CsPt, OS, and OAC by using the primers GalIRES_F, GalIRES_R.

The Gibson Assembly method was used to subclone the PCR fragment from [0057] into the plasmid HO-poly-KanMx4-HO (ATCC 87804) using the primers KmXIRES_F and KmXIRES_R to create the plasmid pHOOSCstKnMxHO.

The plasmid pHOOSCstKnMxHO was digested with NotI and transformed into kMarxHex1 using standard electroporation methods. The selection of stable integrants was done with yeast nitrogen base (YNB) supplemented with amino acid dropout mix (DO supplement-Ura Clonetech 630416) 2% glucose, lmg/ml G418 (Gibco) and 2% Agar plates.

Gene integration and functional gene expression of pHOOSCstKnMxHO validated by genomic PCR and RT-PCR methods respectively. The final strain produced containing the functional expression of Crt, Bktb, MCT1, TeR, Hbd, Erg20p(K179E) CBDAs, CsPt, OS, and OAC was labeled k.MarxCBDA.

Production of CBDA in *K. marxianus.*

To initiate the reconstituted metabolic pathway of CBDA, a colony from *K. marx* CBDA was freshly streaked onto an agar plate from a frozen glycerol stock of k.MarxCBDA. A small culture of VscCBDA was grown in YNBA base (YNB) supplemented with amino acid dropout mix (DO supplement-Ura Clonetech 630416) 2% glucose, 1 mg/ml G418 (Gibco) and 2% Agar plates was grown overnight at 30° C. The overnight culture was transferred to 1 L of YNBA supplemented with base (YNB) supplemented with amino acid dropout mix (DO supplement-Ura Clonetech 630416) 2% glucose, and 1 mg/ml G418 (Gibco) and was grown at 30° C. until mid log phase. Cells were pelleted by centrifugation then washed with 200 ml of phosphate buffered saline (PBS) and repelleted. Pelleted cells were resuspended with 1 L of YNBA supplemented with base (YNB) supplemented with amino acid dropout mix (DO supplement-Ura Clonetech 630416) 2% galactose, and 1 mg/ml G418 (Gibco) and grown at 30° C. overnight.

Processing CBDA for Analysis of Cannabinoid Production.

Overnight 1 L cultures were pelleted by centrifugation, resuspended, washed one time in PBS and pelleted. The process for extracting cannabinoids from the yeast generally follows the following basic steps:

1. Remove the yeast cells from the media by centrifugation or filtration.
2. Lysis the cells using either chemical or mechanical methods or a combination of methods. Mechanical methods can include a French Press or glass bead milling or other standard methods. Chemical methods can include enzymatic cell lysis, solvent cell lysis, or detergent based cell lysis.
3. Perform a liquid-liquid extraction of the cannabinoids form the cell lysate using the appropriate chemical solvent. An appropriate solvent is any solvent where the cannabinoids are highly soluble in this solvent and the solvent is not miscible in water. Examples of this are hexane, ethyl acetate, and cyclohexane. Preferred solvents can be straight or branched alkane chains (C5-C8) work well; mixtures of these solvents can also be use.

Protocol Used for Cannabinoid Extraction from Yeast Cell Lysate

1. After lysising the cells using any mechanical technique, add 1 mL of 4M KCl, pH2.0 to each 1 mL of cell lysate.
2. Add 1-2 mLs of ethyl acetate for each 1 mL of cell lysate.
3. Rigorously mix for 1 min.
4. Centrifuge the mixture for 5 min at 1000×g.
5. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for Cannabinoid Extraction from Growth Media (for Secreted Cannabinoid Samples)

1. Add 1 mL of ethyl acetate for every 1 mL of growth media.
2. Rigorously mix for 1 min.
3. Centrifuge the mixture for 5 min at 1000×g.
4. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for GC-MS Analysis of Cannabinoid Extracts for k.Marx CBDA

1. Remove solvent from samples under vacuum.
2. Re-suspend dry samples in either 100 uL of dry hexane or dry ethyl acetate
3. Add 20 uL of N-Methyl-N-(trimethylsilyl)trifluoroacetamide (MSTFA)
4. Briefly mix
5. Heat solution to 60° C. for 10-15 minutes
6. GC-MS Method
   a. Instrument Agilent 6890-5975 GC-MS (Model Number: Agilent 19091S-433)
   b. Column HP-5MS 5% Phenyl Methyl Siloxane
   c. OVEN:
      i. Initial temp: 100 'C (On) Maximum temp: 300 'C
      ii. Initial time: 3.00 min Equilibration time: 0.50 min
      iii. Ramps:
         # Rate Final temp Final time
         1—30.00 280 1.00
         2—70.00 300 5.00
         3—0.0 (Off)
      iv. Post temp: 0 'C
      v. Post time: 0.00 min
      vi. Run time: 15.29 min

What is claimed is:

1. A method for making cannabigerolic acid, the method comprising:

transforming *S. cervisiae* with a first nucleotide sequence comprising the nucleotide sequence of SEQ. ID. NO.2 expressing an acyl-activating enzyme and expressing a mutant prenyltransferase; and transforming the *S. cervisiae* with a second nucleotide sequence comprising the nucleotide sequence of SEQ. ID. NO.13 expressing olivetolic synthase, expressing olivetolic acid cyclase and expressing aromatic prenyltransferase.

2. A method for making cannabigerolic acid, the method comprising:

transforming a *S. cervisiae* with a first nucleotide sequence comprising the nucleotide sequence of SEQ. ID. NO.1 expressing an acyl-activating enzyme;

transforming the *S. cervisiae* with a second nucleotide sequence comprising the nucleotide sequence of SEQ. ID. NO.22 expressing a mutant prenyltransferase;

transforming the *S. cervisiae* with a third nucleotide sequence comprising the nucleotide sequence of SEQ. ID. NO.10 expressing olivetolic synthase;

transforming the *S. cervisiae* with a fourth nucleotide sequence comprising the nucleotide sequence of SEQ. ID. NO.5 expressing olivetolic acid cyclase; and transforming the *S. cervisiae* with a fifth nucleotide sequence comprising the nucleotide sequence of SEQ. ID. NO.13 expressing aromatic prenyltransferase.

3. A method for making cannabigerolic acid, the method comprising:

transforming *S. cervisiae* with a first nucleotide sequence comprising the nucleotide sequence of SEQ. ID. NO.23 expressing an acyl-activating enzyme;

transforming the *S. cervisiae* with a second nucleotide sequence comprising the nucleotide sequence of SEQ. ID. NO.24 expressing a mutant prenyltransferase;

transforming the *S. cervisiae* with a third nucleotide sequence comprising the nucleotide sequence of SEQ. ID. NO.25 expressing olivetolic synthase;

transforming the *S. cervisiae* with a fourth nucleotide sequence comprising the nucleotide sequence of SEQ. ID. NO.26 expressing olivetolic acid cyclase; and transforming the *S. cervisiae* with a fifth nucleotide sequence comprising the nucleotide sequence of SEQ. ID. NO.27 expressing aromatic prenyltransferase.

* * * * *

UNITED STATES PATENT AND TRADEMARK OFFICE
CERTIFICATE OF CORRECTION

PATENT NO. : 9,822,384 B2
APPLICATION NO. : 14/795816
DATED : November 21, 2017
INVENTOR(S) : Jason L. Poulos and Anthony N. Farina It is certified that error appears in the above-identified patent and that said Letters Patent is hereby corrected as shown below:

On the Title Page

Item (72) To correct inventor's name from "Anthony N. Farnia" to "Anthony N. Farina".

Signed and Sealed this
Twenty-eighth Day of March, 2023

Katherine Kelly Vidal

Katherine Kelly Vidal
*Director of the United States Patent and Trademark Office*